United States Patent
Wang

(10) Patent No.: US 12,024,560 B2
(45) Date of Patent: *Jul. 2, 2024

(54) THERAPEUTIC AGENTS AND METHODS FOR ENHANCING IMMUNE RESPONSES IN TUMOR MICROENVIRONMENT

(71) Applicant: LYVGEN BIOPHARMA HOLDINGS LIMITED, Grand Cayman (KY)

(72) Inventor: Jieyi Wang, Belmont, CA (US)

(73) Assignee: LYVGEN BIOPHARMA HOLDINGS LIMITED, Grand Cayman (KY)

(*) Notice: Subject to any disclaimer, the term of this patent is extended or adjusted under 35 U.S.C. 154(b) by 1143 days.

This patent is subject to a terminal disclaimer.

(21) Appl. No.: 16/498,784

(22) PCT Filed: Mar. 28, 2018

(86) PCT No.: PCT/US2018/024872
§ 371 (c)(1),
(2) Date: Sep. 27, 2019

(87) PCT Pub. No.: WO2018/183520
PCT Pub. Date: Oct. 4, 2018

(65) Prior Publication Data
US 2020/0392227 A1    Dec. 17, 2020

Related U.S. Application Data

(60) Provisional application No. 62/477,661, filed on Mar. 28, 2017.

(51) Int. Cl.
| | | |
|---|---|---|
| *C07K 16/28* | (2006.01) | |
| *A61K 38/18* | (2006.01) | |
| *A61K 39/00* | (2006.01) | |
| *A61P 37/04* | (2006.01) | |
| *C07K 14/705* | (2006.01) | |
| *C07K 16/00* | (2006.01) | |

(52) U.S. Cl.
CPC ........ *C07K 16/283* (2013.01); *A61K 38/1825* (2013.01); *A61P 37/04* (2018.01); *A61K 2039/505* (2013.01); *C07K 14/70503* (2013.01); *C07K 16/00* (2013.01); *C07K 2317/50* (2013.01); *C07K 2317/52* (2013.01)

(58) Field of Classification Search
CPC .............. C07K 14/70503; C07K 16/00; C07K 2317/50; C07K 2317/52
See application file for complete search history.

(56) References Cited

U.S. PATENT DOCUMENTS

| | | | | |
|---|---|---|---|---|
| 8,063,187 B2* | 11/2011 | Chu et al. | ............. | C07K 16/00 424/152.1 |
| 8,101,720 B2* | 1/2012 | Lazar et al. | ............. | A61P 31/00 530/387.3 |
| 11,186,648 B2* | 11/2021 | Wang | ................. | C07K 16/2878 |
| 11,203,643 B2* | 12/2021 | Wang | ................. | C07K 16/2878 |
| 2007/0231329 A1 | 10/2007 | Lazar et al. | | |
| 2013/0144041 A1 | 6/2013 | Dillon et al. | | |
| 2015/0274833 A1 | 10/2015 | Herrmann et al. | | |
| 2016/0207980 A1* | 7/2016 | Du et al. | ................ | C07K 16/00 |
| 2017/0081406 A1 | 3/2017 | Fallah-Arani et al. | | |
| 2017/0088603 A1 | 3/2017 | Fallah-Arani et al. | | |

FOREIGN PATENT DOCUMENTS

| | | |
|---|---|---|
| CN | 101098890 A | 1/2008 |
| CN | 103703129 A | 4/2014 |
| CN | 104788565 A | 7/2015 |
| CN | 105164157 A | 12/2015 |
| WO | WO 2004/063351 A2 | 7/2004 |
| WO | WO 2006/085967 A2 | 8/2006 |
| WO | WO 2006/088494 A2 | 8/2006 |
| WO | WO 2006/105338 A2 | 10/2006 |
| WO | WO 2008/092117 A2 | 7/2008 |
| WO | WO 2009/011941 A2 | 1/2009 |
| WO | WO 2009/041613 A1 | 4/2009 |
| WO | 2012/087928 A2 | 6/2012 |
| WO | WO 2013/092001 A1 | 6/2013 |
| WO | 2014/148895 A1 | 9/2014 |
| WO | WO 2014/144960 A2 | 9/2014 |
| WO | WO 2014/145000 A2 | 9/2014 |
| WO | WO 2014/184545 A2 | 11/2014 |
| WO | WO 2016/030414 A1 | 3/2016 |

(Continued)

OTHER PUBLICATIONS

Chen et al., TNFRSF6B neutralization antibody inhibits proliferation and induces apoptosis in hepatocellular carcinoma cell. Pathol Res Pract. Sep. 15, 2010;206(9):631-41. Epub Jun. 29, 2010.
Li et al., Tumor necrosis factor stimulates matrix metalloproteinase 9 secretion from cultured human chorionic trophoblast cells through TNF receptor 1 signaling to IKBKB-NFKB and MAPK1/3 pathway. Biol Reprod. Sep. 2010;83(3):481-7. Epub May 12, 2010.
Sibilano et al., A TNFRSF14-FcεRI-mast cell pathway contributes to development of multiple features of asthma pathology in mice. Nat Commun. Dec. 16, 2016;7:13696(1-11).

(Continued)

*Primary Examiner* — Vanessa L. Ford
*Assistant Examiner* — Danaya L Middleton
(74) *Attorney, Agent, or Firm* — Mintz, Levin, Cohn, Ferris, Glovsky and Popeo, P.C.

(57) ABSTRACT

Human IgG1, IgG2, and IgG4 mutants having mutations in the hinge domain and exhibiting altered binding activity to Fcγ receptors such as FcγRIIB (CD32B). Also provided herein are methods for selectively activating immune responses in a subject using a therapeutic agent capable of targeting both an immune cell surface receptor and FcγRIIB.

5 Claims, 23 Drawing Sheets
Specification includes a Sequence Listing.

(56) References Cited

FOREIGN PATENT DOCUMENTS

| WO | WO-2016081748 A2 * | 5/2016 | ........... A61K 39/395 |
|---|---|---|---|
| WO | WO 2016/201388 A2 | 12/2016 | |
| WO | WO 2017/040301 A1 | 3/2017 | |
| WO | WO 2017/205738 A1 | 11/2017 | |

OTHER PUBLICATIONS

Dall'Acqua et al., Modulation of the effector functions of a human IgGI through engineering of its hinge region. J Immunol. Jul. 15, 2006;177(2):1129-38.

Saini et al., Structural evidence for a new IgGI antibody sequence allele of cattle. Scand J Immunol. Jan. 2007;65(1):32-8.

Silva et al., The S228P mutation prevents in vivo and in vitro IgG4 Fab-arm exchange as demonstrated using a combination of novel quantitative immunoassays and physiological matrix preparation. J Biol Chem. Feb. 27, 2015;290(9):5462-9. Epub Jan. 7, 2015.

Brezski et al. "Immunoglobulin isotype knowledge and application to Fc engineering" Science Direct, Current Opinion in Immunology 2016, 40:62-69.

Mimoto et al. "Engineered antibody Fc variant with selectively enhanced FcgRIIb binding over both FcgRIIaR131 and FcgRIIaH131" Protein Engineering, Design & Selection vol. 26 No. 10 pp. 589-598, 2013.

PCT/US18/024872, Sep. 20, 2018, International Search Report.

Chu, Seung Y., et al. "Inhibition of B cell receptor-mediated activation of primary human B cells by coengagement of CD19 and FcγRIIb with Fc-engineered antibodies." Molecular Immunology, vol. 45, No. 15, pp. 3926-3933, Sep. 2008.

* cited by examiner

```
                       SEQUENCE LISTING

<160> NUMBER OF SEQ ID NOS: 128

<210> SEQ ID NO 1
<211> LENGTH: 237
<212> TYPE: PRT
<213> ORGANISM: Homo sapiens

<400> SEQUENCE: 1

Val Asp Lys Lys Val Glu Pro Lys Ser Cys Asp Lys Thr His Thr Cys
1               5                   10                  15

Pro Pro Cys Pro Ala Pro Glu Leu Leu Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 2
<211> LENGTH: 233
<212> TYPE: PRT
<213> ORGANISM: Homo sapiens

<400> SEQUENCE: 2

Val Asp Lys Thr Val Glu Arg Lys Cys Cys Val Glu Cys Pro Pro Cys
1               5                   10                  15

Pro Ala Pro Pro Val Ala Gly Pro Ser Val Phe Leu Phe Pro Pro Lys
```

```
            20                  25                  30
Pro Lys Asp Thr Leu Met Ile Ser Arg Thr Pro Glu Val Thr Cys Val
            35                  40                  45

Val Val Asp Val Ser His Glu Asp Pro Glu Val Gln Phe Asn Trp Tyr
50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Leu Pro Ala Pro Ile Glu Lys Thr Ile Ser Lys Thr Lys Gly Gln
            115                 120                 125

Pro Arg Glu Pro Gln Val Tyr Thr Leu Pro Pro Ser Arg Glu Glu Met
            130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
            210                 215                 220

Lys Ser Leu Ser Leu Ser Pro Gly Lys
225                 230

<210> SEQ ID NO 3
<211> LENGTH: 234
<212> TYPE: PRT
<213> ORGANISM: Homo sapiens

<400> SEQUENCE: 3

Val Asp Lys Arg Val Glu Ser Lys Tyr Gly Pro Pro Cys Pro Ser Cys
1               5                   10                  15

Pro Ala Pro Glu Phe Leu Gly Gly Pro Ser Val Phe Leu Phe Pro Pro
            20                  25                  30

Lys Pro Lys Asp Thr Leu Met Ile Ser Arg Thr Pro Glu Val Thr Cys
            35                  40                  45

Val Val Val Asp Val Ser Gln Glu Asp Pro Glu Val Gln Phe Asn Trp
50                  55                  60

Tyr Val Asp Gly Val Glu Val His Asn Ala Lys Thr Lys Pro Arg Glu
65                  70                  75                  80

Glu Gln Phe Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Gly Leu Pro Ser Ser Ile Glu Lys Thr Ile Ser Lys Ala Lys Gly
            115                 120                 125

Gln Pro Arg Glu Pro Gln Val Tyr Thr Leu Pro Pro Ser Gln Glu Glu
            130                 135                 140

Met Thr Lys Asn Gln Val Ser Leu Thr Cys Leu Val Lys Gly Phe Tyr
145                 150                 155                 160
```

```
Pro Ser Asp Ile Ala Val Glu Trp Glu Ser Asn Gly Gln Pro Glu Asn
            165                 170                 175

Asn Tyr Lys Thr Thr Pro Pro Val Leu Asp Ser Asp Gly Ser Phe Phe
        180                 185                 190

Leu Tyr Ser Arg Leu Thr Val Asp Lys Ser Arg Trp Gln Glu Gly Asn
    195                 200                 205

Val Phe Ser Cys Ser Val Met His Glu Ala Leu His Asn His Tyr Thr
210                 215                 220

Gln Lys Ser Leu Ser Leu Ser Leu Gly Lys
225                 230
```

<210> SEQ ID NO 4
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 4

```
Val Asp Lys Arg Val Glu Ser Lys Tyr Gly Pro Pro Cys Pro Pro Cys
1               5                   10                  15

Pro Ala Pro Glu Phe Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser Gln Glu Asp Pro Glu Val Gln Phe Asn Trp
    50                  55                  60

Tyr Val Asp Gly Val Glu Val His Asn Ala Lys Thr Lys Pro Arg Glu
65                  70                  75                  80

Glu Gln Phe Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Gly Leu Pro Ser Ser Ile Glu Lys Thr Ile Ser Lys Ala Lys Gly
        115                 120                 125

Gln Pro Arg Glu Pro Gln Val Tyr Thr Leu Pro Pro Ser Gln Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Arg Leu Thr Val Asp Lys Ser Arg Trp Gln Glu Gly Asn
        195                 200                 205

Val Phe Ser Cys Ser Val Met His Glu Ala Leu His Asn His Tyr Thr
    210                 215                 220

Gln Lys Ser Leu Ser Leu Ser Leu Gly Lys
225                 230
```

<210> SEQ ID NO 5
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 5

```
Val Asp Lys Lys Val Glu Pro Lys Ser Cys Asp Lys Thr His Thr Cys
1               5                   10                  15

Pro Pro Cys Pro Ala Pro Glu Leu Leu Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
210                 215                 220

Gln Lys Ser Leu Ser Leu Ser Pro Gly Lys
225                 230

<210> SEQ ID NO 6
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 6

Val Asp Lys Lys Val Glu Pro Lys Ser Cys Asp Lys Thr His Thr Cys
1               5                   10                  15

Pro Pro Cys Pro Ala Pro Glu Leu Leu Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125
```

```
Lys Gly Gln Pro Arg Glu Pro Gln Val Tyr Thr Leu Pro Ser Arg
    130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235

<210> SEQ ID NO 7
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 7

Val Asp Lys Lys Val Glu Pro Lys Cys Cys Val Glu Cys Pro Pro Cys
1               5                   10                  15

Pro Ala Pro Glu Leu Leu Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 8
```

```
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 8

Val Asp Lys Lys Val Glu Pro Lys Tyr Gly Pro Cys Pro Pro Cys
1               5                   10                  15

Pro Ala Pro Glu Leu Leu Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 9
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 9

Val Asp Lys Lys Val Glu Pro Lys Ser Cys Asp Lys Thr His Thr Cys
1               5                   10                  15

Pro Pro Cys Pro Ala Pro Glu Leu Leu Gly Gly Pro Ser Val Phe Leu
                20                  25                  30

Phe Pro Pro Lys Pro Lys Asp Thr Leu Met Ile Ser Arg Thr Pro Glu
            35                  40                  45

Val Thr Cys Val Val Val Asp Val Ser His Glu Asp Pro Glu Glu Lys
        50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
```

```
                        85                  90                  95
Thr Val Leu His Gln Asp Trp Leu Asn Gly Lys Glu Tyr Lys Cys Lys
                100                 105                 110

Val Ser Asn Lys Ala Leu Pro Ala Pro Ile Glu Lys Thr Ile Ser Lys
            115                 120                 125

Ala Lys Gly Gln Pro Arg Glu Pro Gln Val Tyr Thr Leu Pro Pro Ser
        130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235

<210> SEQ ID NO 10
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 10

Val Asp Lys Lys Val Glu Pro Lys Ser Cys Asp Lys Thr His Thr Cys
1               5                   10                  15

Pro Pro Cys Pro Ala Pro Glu Leu Leu Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Glu His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
                100                 105                 110

Val Ser Asn Lys Ala Leu Pro Ala Pro Ile Glu Lys Thr Ile Ser Lys
            115                 120                 125

Ala Lys Gly Gln Pro Arg Glu Pro Gln Val Tyr Thr Leu Pro Pro Ser
        130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
```

-continued

```
           210                 215                 220
    His Tyr Thr Gln Lys Ser Leu Ser Leu Ser Pro Gly Lys
    225                 230                 235

<210> SEQ ID NO 11
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 11

Val Asp Lys Lys Val Glu Pro Lys Ser Cys Asp Lys Thr His Thr Cys
    1               5                   10                  15

Pro Pro Cys Pro Ala Pro Glu Leu Leu Gly Gly Pro Ser Val Phe Leu
                    20                  25                  30

Phe Pro Pro Lys Pro Lys Asp Thr Leu Met Ile Ser Arg Thr Pro Glu
                35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
    65                  70                  75                  80

Pro Arg Glu Glu Gln Tyr Asn Ser Thr Tyr Arg Val Val Ser Val Leu
                    85                  90                  95

Thr Val Leu His Gln Asp Trp Leu Asn Gly Lys Glu Tyr Lys Cys Lys
                    100                 105                 110

Val Ser Asn Lys Ala Phe Pro Ala Pro Ile Glu Lys Thr Ile Ser Lys
                115                 120                 125

Ala Lys Gly Gln Pro Arg Glu Pro Gln Val Tyr Thr Leu Pro Pro Ser
            130                 135                 140

Arg Glu Glu Met Thr Lys Asn Gln Val Ser Leu Thr Cys Leu Val Lys
    145                 150                 155                 160

Gly Phe Tyr Pro Ser Asp Ile Ala Val Glu Trp Glu Ser Asn Gly Gln
                    165                 170                 175

Pro Glu Asn Asn Tyr Lys Thr Thr Pro Pro Val Leu Asp Ser Asp Gly
                180                 185                 190

Ser Phe Phe Leu Tyr Ser Lys Leu Thr Val Asp Lys Ser Arg Trp Gln
                195                 200                 205

Gln Gly Asn Val Phe Ser Cys Ser Val Met His Glu Ala Leu His Asn
            210                 215                 220

His Tyr Thr Gln Lys Ser Leu Ser Leu Ser Pro Gly Lys
    225                 230                 235

<210> SEQ ID NO 12
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 12

Val Asp Lys Lys Val Glu Pro Lys Ser Cys Asp Lys Thr His Thr Cys
    1               5                   10                  15

Pro Pro Cys Pro Ala Pro Glu Leu Leu Gly Gly Pro Ser Val Phe Leu
                    20                  25                  30

Phe Pro Pro Lys Pro Lys Asp Thr Leu Met Ile Ser Arg Thr Pro Glu
                35                  40                  45
```

```
Val Thr Cys Val Val Val Asp Val Glu His Glu Asp Pro Glu Val Lys
    50                  55                  60
Phe Asn Trp Tyr Val Asp Gly Val Glu Val His Asn Ala Lys Thr Lys
65                  70                  75                  80
Pro Arg Glu Glu Gln Tyr Asn Ser Thr Tyr Arg Val Val Ser Val Leu
                85                  90                  95
Thr Val Leu His Gln Asp Trp Leu Asn Gly Lys Glu Tyr Lys Cys Lys
            100                 105                 110
Val Ser Asn Lys Ala Phe Pro Ala Pro Ile Glu Lys Thr Ile Ser Lys
        115                 120                 125
Ala Lys Gly Gln Pro Arg Glu Pro Gln Val Tyr Thr Leu Pro Pro Ser
130                 135                 140
Arg Glu Glu Met Thr Lys Asn Gln Val Ser Leu Thr Cys Leu Val Lys
145                 150                 155                 160
Gly Phe Tyr Pro Ser Asp Ile Ala Val Glu Trp Glu Ser Asn Gly Gln
                165                 170                 175
Pro Glu Asn Asn Tyr Lys Thr Thr Pro Pro Val Leu Asp Ser Asp Gly
            180                 185                 190
Ser Phe Phe Leu Tyr Ser Lys Leu Thr Val Asp Lys Ser Arg Trp Gln
        195                 200                 205
Gln Gly Asn Val Phe Ser Cys Ser Val Met His Glu Ala Leu His Asn
210                 215                 220
His Tyr Thr Gln Lys Ser Leu Ser Leu Ser Pro Gly Lys
225                 230                 235

<210> SEQ ID NO 13
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 13

Val Asp Lys Lys Val Glu Pro Lys Ser Cys Asp Lys Thr His Thr Cys
1               5                   10                  15
Pro Pro Cys Pro Ala Pro Glu Leu Leu Ser Val Phe Leu Phe Pro Pro
            20                  25                  30
Lys Pro Lys Asp Thr Leu Met Ile Ser Arg Thr Pro Glu Val Thr Cys
        35                  40                  45
Val Val Val Asp Val Ser His Glu Asp Pro Glu Glu Lys Phe Asn Trp
    50                  55                  60
Tyr Val Asp Gly Val Glu Val His Asn Ala Lys Thr Lys Pro Arg Glu
65                  70                  75                  80
Glu Gln Tyr Asn Ser Thr Tyr Arg Val Val Ser Val Leu Thr Val Leu
                85                  90                  95
His Gln Asp Trp Leu Asn Gly Lys Glu Tyr Lys Cys Lys Val Ser Asn
            100                 105                 110
Lys Ala Leu Pro Ala Pro Ile Glu Lys Thr Ile Ser Lys Ala Lys Gly
        115                 120                 125
Gln Pro Arg Glu Pro Gln Val Tyr Thr Leu Pro Pro Ser Arg Glu Glu
130                 135                 140
Met Thr Lys Asn Gln Val Ser Leu Thr Cys Leu Val Lys Gly Phe Tyr
145                 150                 155                 160
Pro Ser Asp Ile Ala Val Glu Trp Glu Ser Asn Gly Gln Pro Glu Asn
                165                 170                 175
```

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Lys
225                 230

<210> SEQ ID NO 14
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 14

Val Asp Lys Lys Val Glu Pro Lys Ser Cys Asp Lys Thr His Thr Cys
1               5                   10                  15

Pro Pro Cys Pro Ala Pro Glu Leu Leu Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Glu His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Lys
225                 230

<210> SEQ ID NO 15
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 15

Val Asp Lys Lys Val Glu Pro Lys Ser Cys Asp Lys Thr His Thr Cys
1               5                   10                  15

```
Pro Pro Cys Pro Ala Pro Glu Leu Leu Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Phe Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
210                 215                 220

Gln Lys Ser Leu Ser Leu Ser Pro Gly Lys
225                 230

<210> SEQ ID NO 16
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 16

Val Asp Lys Lys Val Glu Pro Lys Ser Cys Asp Lys Thr His Thr Cys
1               5                   10                  15

Pro Pro Cys Pro Ala Pro Glu Leu Leu Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Glu His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Phe Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Glu Glu
130                 135                 140
```

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
210                 215                 220

Gln Lys Ser Leu Ser Leu Ser Pro Gly Lys
225                 230

<210> SEQ ID NO 17
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 17

Val Asp Lys Lys Val Glu Pro Lys Ser Cys Asp Lys Thr His Thr Cys
1               5                   10                  15

Pro Pro Cys Pro Ala Pro Glu Leu Leu Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Glu Lys Phe
50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
210                 215                 220

Tyr Thr Gln Lys Ser Leu Ser Leu Ser Pro Gly Lys
225                 230                 235

<210> SEQ ID NO 18
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 18

```
Val Asp Lys Lys Val Glu Pro Lys Ser Cys Asp Lys Thr His Thr Cys
1               5                   10                  15

Pro Pro Cys Pro Ala Pro Glu Leu Leu Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Glu His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Leu Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235
```

<210> SEQ ID NO 19
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 19

```
Val Asp Lys Lys Val Glu Pro Lys Ser Cys Asp Lys Thr His Thr Cys
1               5                   10                  15

Pro Pro Cys Pro Ala Pro Glu Leu Leu Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser His Glu Asp Pro Glu Val Lys Phe
    50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
```

```
            100                 105                 110
Ser Asn Lys Ala Phe Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235

<210> SEQ ID NO 20
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 20

Val Asp Lys Lys Val Glu Pro Lys Ser Cys Asp Lys Thr His Thr Cys
1               5                   10                  15

Pro Pro Cys Pro Ala Pro Glu Leu Leu Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Glu His Glu Asp Pro Glu Val Lys Phe
50                  55                  60

Asn Trp Tyr Val Asp Gly Val Glu Val His Asn Ala Lys Thr Lys Pro
65                  70                  75                  80

Arg Glu Glu Gln Tyr Asn Ser Thr Tyr Arg Val Val Ser Val Leu Thr
                85                  90                  95

Val Leu His Gln Asp Trp Leu Asn Gly Lys Glu Tyr Lys Cys Lys Val
            100                 105                 110

Ser Asn Lys Ala Phe Pro Ala Pro Ile Glu Lys Thr Ile Ser Lys Ala
        115                 120                 125

Lys Gly Gln Pro Arg Glu Pro Gln Val Tyr Thr Leu Pro Pro Ser Arg
    130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
```

```
225                 230                 235
```

<210> SEQ ID NO 21
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 21

```
Val Asp Lys Lys Val Glu Pro Lys Ser Cys Asp Lys Thr His Thr Cys
1               5                   10                  15

Pro Pro Cys Pro Ala Pro Glu Ala Ala Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60

Phe Asn Trp Tyr Val Asp Gly Val Glu Val His Asn Ala Lys Thr Lys
65                  70                  75                  80

Pro Arg Glu Glu Gln Tyr Asn Ser Thr Tyr Arg Val Val Ser Val Leu
                85                  90                  95

Thr Val Leu His Gln Asp Trp Leu Asn Gly Lys Glu Tyr Lys Cys Lys
            100                 105                 110

Val Ser Asn Lys Ala Leu Pro Ala Pro Ile Glu Lys Thr Ile Ser Lys
        115                 120                 125

Ala Lys Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235
```

<210> SEQ ID NO 22
<211> LENGTH: 237
<212> TYPE: PRT
<213> ORGANISM: Artificial Sequence
<220> FEATURE:
<223> OTHER INFORMATION: Synthetic polypeptide

<400> SEQUENCE: 22

```
Val Asp Lys Lys Val Glu Pro Lys Ser Cys Asp Lys Thr His Thr Cys
1               5                   10                  15

Pro Pro Cys Pro Ala Pro Glu Ala Ala Gly Gly Pro Ser Val Phe Leu
            20                  25                  30

Phe Pro Pro Lys Pro Lys Asp Thr Leu Met Ile Ser Arg Thr Pro Glu
        35                  40                  45

Val Thr Cys Val Val Val Asp Val Ser His Glu Asp Pro Glu Val Lys
    50                  55                  60
```

```
Phe Asn Trp Tyr Val Asp Gly Val Glu Val His Asn Ala Lys Thr Lys
 65                  70                  75                  80

Pro Arg Glu Glu Gln Tyr Asn Ser Thr Tyr Arg Val Val Ser Val Leu
                 85                  90                  95

Thr Val Leu His Gln Asp Trp Leu Asn Gly Lys Glu Tyr Lys Cys Lys
            100                 105                 110

Val Ser Asn Lys Ala Leu Gly Ala Pro Ile Glu Lys Thr Ile Ser Lys
        115                 120                 125

Ala Lys Gly Gln Pro Arg Glu Pro Gln Val Tyr Thr Leu Pro Pro Ser
130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Asn Gly Gln
                165                 170                 175

Pro Glu Asn Asn Tyr Lys Thr Thr Pro Pro Val Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Val Phe Ser Cys Ser Val Met His Glu Ala Leu His Asn
210                 215                 220

His Tyr Thr Gln Lys Ser Leu Ser Leu Ser Pro Gly Lys
225                 230                 235

<210> SEQ ID NO 23
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 23

Val Asp Lys Thr Val Glu Arg Lys Cys Cys Val Glu Cys Pro Pro Cys
  1               5                  10                  15

Pro Ala Pro Pro Val Ala Ser Val Phe Leu Phe Pro Pro Lys Pro Lys
                 20                  25                  30

Asp Thr Leu Met Ile Ser Arg Thr Pro Glu Val Thr Cys Val Val Val
             35                  40                  45

Asp Val Ser His Glu Asp Pro Glu Val Gln Phe Asn Trp Tyr Val Asp
         50                  55                  60

Gly Val Glu Val His Asn Ala Lys Thr Lys Pro Arg Glu Glu Gln Phe
 65                  70                  75                  80

Asn Ser Thr Phe Arg Val Val Ser Val Leu Thr Val Val His Gln Asp
                 85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190
```

```
Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225             230

<210> SEQ ID NO 24
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 24

Val Asp Lys Thr Val Glu Arg Lys Ser Cys Asp Lys Thr His Thr Cys
1               5                   10                  15

Pro Pro Cys Pro Ala Pro Val Ala Gly Pro Ser Val Phe Leu Phe
            20                  25                  30

Pro Pro Lys Pro Lys Asp Thr Leu Met Ile Ser Arg Thr Pro Glu Val
            35                  40                  45

Thr Cys Val Val Val Asp Val Ser His Glu Asp Pro Glu Val Gln Phe
        50                  55                  60

Asn Trp Tyr Val Asp Gly Val Glu Val His Asn Ala Lys Thr Lys Pro
65                  70                  75                  80

Arg Glu Glu Gln Phe Asn Ser Thr Phe Arg Val Val Ser Val Leu Thr
                85                  90                  95

Val Val His Gln Asp Trp Leu Asn Gly Lys Glu Tyr Lys Cys Lys Val
            100                 105                 110

Ser Asn Lys Gly Leu Pro Ala Pro Ile Glu Lys Thr Ile Ser Lys Thr
        115                 120                 125

Lys Gly Gln Pro Arg Glu Pro Gln Val Tyr Thr Leu Pro Pro Ser Arg
130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Met Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235

<210> SEQ ID NO 25
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 25

Val Asp Lys Thr Val Glu Arg Lys Cys Cys Val Glu Cys Pro Pro Cys
1               5                   10                  15

Pro Ala Pro Pro Phe Leu Gly Gly Pro Ser Val Phe Leu Phe Pro Pro
            20                  25                  30
```

```
Lys Pro Lys Asp Thr Leu Met Ile Ser Arg Thr Pro Glu Val Thr Cys
            35                  40                  45

Val Val Val Asp Val Ser His Glu Asp Pro Glu Val Gln Phe Asn Trp
 50                  55                  60

Tyr Val Asp Gly Val Glu Val His Asn Ala Lys Thr Lys Pro Arg Glu
 65                  70                  75                  80

Glu Gln Phe Asn Ser Thr Phe Arg Val Val Ser Val Leu Thr Val Val
                 85                  90                  95

His Gln Asp Trp Leu Asn Gly Lys Glu Tyr Lys Cys Lys Val Ser Asn
                100                 105                 110

Lys Gly Leu Pro Ala Pro Ile Glu Lys Thr Ile Ser Lys Thr Lys Gly
            115                 120                 125

Gln Pro Arg Glu Pro Gln Val Tyr Thr Leu Pro Pro Ser Arg Glu Glu
130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Met Leu Asp Ser Asp Gly Ser Phe Phe
                180                 185                 190

Leu Tyr Ser Lys Leu Thr Val Asp Lys Ser Arg Trp Gln Gln Gly Asn
            195                 200                 205

Val Phe Ser Cys Ser Val Met His Glu Ala Leu His Asn His Tyr Thr
210                 215                 220

Gln Lys Ser Leu Ser Leu Ser Pro Gly Lys
225                 230

<210> SEQ ID NO 26
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 26

Val Asp Lys Thr Val Glu Arg Lys Tyr Gly Pro Pro Cys Pro Pro Cys
1               5                   10                  15

Pro Ala Pro Pro Val Ala Gly Pro Ser Val Phe Leu Phe Pro Pro Lys
                20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Gln Phe Asn Trp Tyr
 50                  55                  60

Val Asp Gly Val Glu Val His Asn Ala Lys Thr Lys Pro Arg Glu Glu
 65                  70                  75                  80

Gln Phe Asn Ser Thr Phe Arg Val Val Ser Val Leu Thr Val Val His
                 85                  90                  95

Gln Asp Trp Leu Asn Gly Lys Glu Tyr Lys Cys Lys Val Ser Asn Lys
                100                 105                 110

Gly Leu Pro Ala Pro Ile Glu Lys Thr Ile Ser Lys Thr Lys Gly Gln
            115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160
```

Ser Asp Ile Ala Val Glu Trp Glu Ser Asn Gly Gln Pro Glu Asn Asn
            165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
            210                 215                 220

Lys Ser Leu Ser Leu Ser Pro Gly Lys
225                 230

<210> SEQ ID NO 27
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 27

Val Asp Lys Thr Val Glu Arg Lys Cys Cys Val Glu Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Glu Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Leu Pro Ala Pro Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
            165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
            210                 215                 220

Lys Ser Leu Ser Leu Ser Pro Gly Lys
225                 230

<210> SEQ ID NO 28
<211> LENGTH: 233
<212> TYPE: PRT
<213> ORGANISM: Artificial Sequence
<220> FEATURE:
<223> OTHER INFORMATION: Synthetic polypeptide

```
<400> SEQUENCE: 28

Val Asp Lys Thr Val Glu Arg Lys Cys Cys Val Glu Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Glu His Glu Asp Pro Glu Val Gln Phe Asn Trp Tyr
50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Leu Pro Ala Pro Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 29
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 29

Val Asp Lys Thr Val Glu Arg Lys Cys Cys Val Glu Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Gln Phe Asn Trp Tyr
50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Phe Pro Ala Pro Ile Glu Lys Thr Ile Ser Lys Thr Lys Gly Gln
```

```
            115                 120                 125
Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 30
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 30

Val Asp Lys Thr Val Glu Arg Lys Cys Cys Val Glu Cys Pro Pro Cys
1               5                   10                  15

Pro Ala Pro Pro Val Ala Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Glu His Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Phe Arg Val Val Ser Val Leu Thr Val Val His
                85                  90                  95

Gln Asp Trp Leu Asn Gly Lys Glu Tyr Lys Cys Lys Val Ser Asn Lys
            100                 105                 110

Gly Phe Pro Ala Pro Ile Glu Lys Thr Ile Ser Lys Thr Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Met Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230
```

<210> SEQ ID NO 31
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 31

```
Val Asp Lys Thr Val Glu Arg Lys Cys Cys Val Glu Cys Pro Pro Cys
1               5                   10                  15

Pro Ala Pro Glu Val Ser Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Phe
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 32
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 32

```
Val Asp Lys Thr Val Glu Arg Lys Cys Cys Val Glu Cys Pro Pro Cys
1               5                   10                  15

Pro Ala Pro Pro Val Ala Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Glu Gln Phe Asn Trp Tyr Val Asp
    50                  55                  60

Gly Val Glu Val His Asn Ala Lys Thr Lys Pro Arg Glu Glu Gln Phe
65                  70                  75                  80
```

```
Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 33
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 33

Val Asp Lys Thr Val Glu Arg Lys Cys Cys Val Glu Cys Pro Pro Cys
1               5                   10                  15

Pro Ala Pro Pro Val Ala Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Glu His Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205
```

Cys Ser Val Met His Glu Ala Leu His Asn His Tyr Thr Gln Lys Ser
        210                 215                 220

Leu Ser Leu Ser Pro Gly Lys
225                 230

<210> SEQ ID NO 34
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 34

Val Asp Lys Thr Val Glu Arg Lys Cys Cys Val Glu Cys Pro Pro Cys
1               5                   10                  15

Pro Ala Pro Pro Val Ala Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser His Glu Asp Pro Glu Val Gln Phe Asn Trp Tyr Val Asp
        50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Phe
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 35
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 35

Val Asp Lys Thr Val Glu Arg Lys Cys Cys Val Glu Cys Pro Pro Cys
1               5                   10                  15

Pro Ala Pro Pro Val Ala Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

```
Asp Val Glu His Glu Asp Pro Glu Val Gln Phe Asn Trp Tyr Val Asp
         50                  55                  60

Gly Val Glu Val His Asn Ala Lys Thr Lys Pro Arg Glu Glu Gln Phe
 65                  70                  75                  80

Asn Ser Thr Phe Arg Val Val Ser Val Leu Thr Val Val His Gln Asp
             85                  90                  95

Trp Leu Asn Gly Lys Glu Tyr Lys Cys Lys Val Ser Asn Lys Gly Phe
            100                 105                 110

Pro Ala Pro Ile Glu Lys Thr Ile Ser Lys Thr Lys Gly Gln Pro Arg
            115                 120                 125

Glu Pro Gln Val Tyr Thr Leu Pro Pro Ser Arg Glu Glu Met Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 36
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 36

Val Asp Lys Thr Val Glu Arg Lys Cys Cys Val Glu Cys Pro Pro Cys
1               5                   10                  15

Pro Ala Pro Pro Val Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Phe Asn Ser Thr Phe Arg Val Val Ser Val Leu Thr Val Val His Gln
                85                  90                  95

Asp Trp Leu Asn Gly Lys Glu Tyr Lys Cys Lys Val Ser Asn Lys Gly
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 37
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 37

Val Asp Lys Thr Val Glu Arg Lys Cys Cys Val Glu Cys Pro Pro Cys
1               5                   10                  15

Pro Ala Pro Pro Val Ala Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Phe Asn Ser Thr Phe Arg Val Val Ser Val Leu Thr Val Val His Gln
                85                  90                  95

Asp Trp Leu Asn Gly Lys Glu Tyr Lys Cys Lys Val Ser Asn Lys Gly
            100                 105                 110

Leu Pro Ala Pro Ile Glu Lys Thr Ile Ser Lys Thr Lys Gly Gln Pro
            115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 38
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 38

Val Asp Lys Thr Val Glu Arg Lys Cys Cys Val Glu Cys Pro Pro Cys
```

```
             1               5                  10                 15
           Pro Ala Pro Pro Val Ala Pro Ser Val Phe Leu Phe Pro Pro Lys Pro
                          20                 25                 30

Lys Asp Thr Leu Met Ile Ser Arg Thr Pro Glu Val Thr Cys Val Val
                          35                 40                 45

Val Asp Val Glu His Glu Asp Pro Glu Val Gln Phe Asn Trp Tyr Val
               50                 55                 60

Asp Gly Val Glu Val His Asn Ala Lys Thr Lys Pro Arg Glu Glu Gln
           65                 70                 75                 80

Phe Asn Ser Thr Phe Arg Val Val Ser Val Leu Thr Val Val His Gln
                              85                 90                 95

Asp Trp Leu Asn Gly Lys Glu Tyr Lys Cys Lys Val Ser Asn Lys Gly
                          100                125                110

Leu Pro Ala Pro Ile Glu Lys Thr Ile Ser Lys Thr Lys Gly Gln Pro
                          115                120                125

Arg Glu Pro Gln Val Tyr Thr Leu Pro Pro Ser Arg Glu Glu Met Thr
           130                135                140

Lys Asn Gln Val Ser Leu Thr Cys Leu Val Lys Gly Phe Tyr Pro Ser
           145                150                155                160

Asp Ile Ala Val Glu Trp Glu Ser Asn Gly Gln Pro Glu Asn Asn Tyr
                              165                170                175

Lys Thr Thr Pro Pro Met Leu Asp Ser Asp Gly Ser Phe Phe Leu Tyr
                          180                185                190

Ser Lys Leu Thr Val Asp Lys Ser Arg Trp Gln Gln Gly Asn Val Phe
                          195                200                205

Ser Cys Ser Val Met His Glu Ala Leu His Asn His Tyr Thr Gln Lys
                          210                215                220

Ser Leu Ser Leu Ser Pro Gly Lys
           225                230

<210> SEQ ID NO 39
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 39

Val Asp Lys Arg Val Glu Ser Lys Tyr Gly Pro Pro Cys Pro Pro Cys
1               5                   10                  15

Pro Ala Pro Glu Phe Leu Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser Gln Glu Asp Pro Glu Val Gln Phe Asn Trp Tyr Val Asp
        50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Gln Glu Glu Met Thr Lys
```

```
                130             135             140
Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Glu Gly Asn Val Phe Ser
        195                 200                 205

Cys Ser Val Met His Glu Ala Leu His Asn His Tyr Thr Gln Lys Ser
        210                 215                 220

Leu Ser Leu Ser Leu Gly Lys
225                 230

<210> SEQ ID NO 40
<211> LENGTH: 239
<212> TYPE: PRT
<213> ORGANISM: Artificial Sequence
<220> FEATURE:
<223> OTHER INFORMATION: Synthetic polypeptide

<400> SEQUENCE: 40

Val Asp Lys Arg Val Glu Ser Lys Ser Cys Asp Lys Thr His Thr Pro
1               5                   10                  15

Pro Cys Pro Pro Cys Pro Ala Pro Glu Phe Leu Gly Gly Pro Ser Val
                20                  25                  30

Phe Leu Phe Pro Pro Lys Pro Lys Asp Thr Leu Met Ile Ser Arg Thr
            35                  40                  45

Pro Glu Val Thr Cys Val Val Val Asp Val Ser Gln Glu Asp Pro Glu
    50                  55                  60

Val Gln Phe Asn Trp Tyr Val Asp Gly Val Glu Val His Asn Ala Lys
65                  70                  75                  80

Thr Lys Pro Arg Glu Glu Gln Phe Asn Ser Thr Tyr Arg Val Val Ser
                85                  90                  95

Val Leu Thr Val Leu His Gln Asp Trp Leu Asn Gly Lys Glu Tyr Lys
            100                 105                 110

Cys Lys Val Ser Asn Lys Gly Leu Pro Ser Ser Ile Glu Lys Thr Ile
        115                 120                 125

Ser Lys Ala Lys Gly Gln Pro Arg Glu Pro Gln Val Tyr Thr Leu Pro
    130                 135                 140

Pro Ser Gln Glu Glu Met Thr Lys Asn Gln Val Ser Leu Thr Cys Leu
145                 150                 155                 160

Val Lys Gly Phe Tyr Pro Ser Asp Ile Ala Val Glu Trp Glu Ser Asn
                165                 170                 175

Gly Gln Pro Glu Asn Asn Tyr Lys Thr Thr Pro Pro Val Leu Asp Ser
            180                 185                 190

Asp Gly Ser Phe Phe Leu Tyr Ser Arg Leu Thr Val Asp Lys Ser Arg
        195                 200                 205

Trp Gln Glu Gly Asn Val Phe Ser Cys Ser Val Met His Glu Ala Leu
    210                 215                 220

His Asn His Tyr Thr Gln Lys Ser Leu Ser Leu Ser Leu Gly Lys
225                 230                 235

<210> SEQ ID NO 41
<211> LENGTH: 233
<212> TYPE: PRT
```

<213> ORGANISM: Artificial Sequence
<220> FEATURE:
<223> OTHER INFORMATION: Synthetic polypeptide

<400> SEQUENCE: 41

```
Val Asp Lys Arg Val Glu Ser Lys Tyr Gly Pro Pro Cys Pro Pro Cys
1               5                   10                  15

Pro Ala Pro Glu Phe Leu Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230
```

<210> SEQ ID NO 42
<211> LENGTH: 236
<212> TYPE: PRT
<213> ORGANISM: Artificial Sequence
<220> FEATURE:
<223> OTHER INFORMATION: Synthetic polypeptide

<400> SEQUENCE: 42

```
Val Asp Lys Arg Val Glu Ser Lys Cys Cys Val Glu Pro Pro Cys Pro
1               5                   10                  15

Pro Cys Pro Ala Pro Glu Phe Leu Gly Gly Pro Ser Val Phe Leu Phe
            20                  25                  30

Pro Pro Lys Pro Lys Asp Thr Leu Met Ile Ser Arg Thr Pro Glu Val
        35                  40                  45

Thr Cys Val Val Val Asp Val Ser Gln Glu Asp Pro Glu Val Gln Phe
    50                  55                  60

Asn Trp Tyr Val Asp Gly Val Glu Val His Asn Ala Lys Thr Lys Pro
65                  70                  75                  80

Arg Glu Glu Gln Phe Asn Ser Thr Tyr Arg Val Val Ser Val Leu Thr
                85                  90                  95
```

Val Leu His Gln Asp Trp Leu Asn Gly Lys Glu Tyr Lys Cys Lys Val
                100                 105                 110

Ser Asn Lys Gly Leu Pro Ser Ser Ile Glu Lys Thr Ile Ser Lys Ala
            115                 120                 125

Lys Gly Gln Pro Arg Glu Pro Gln Val Tyr Thr Leu Pro Pro Ser Gln
        130                 135                 140

Glu Glu Met Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Arg Leu Thr Val Asp Lys Ser Arg Trp Gln Glu
        195                 200                 205

Gly Asn Val Phe Ser Cys Ser Val Met His Glu Ala Leu His Asn His
210                 215                 220

Tyr Thr Gln Lys Ser Leu Ser Leu Ser Leu Gly Lys
225                 230                 235

<210> SEQ ID NO 43
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 43

Val Asp Lys Arg Val Glu Ser Lys Tyr Gly Pro Pro Cys Pro Pro Cys
1               5                   10                  15

Pro Ala Pro Glu Phe Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser Gln Glu Asp Pro Glu Val Gln Phe Asn Trp
    50                  55                  60

Tyr Val Asp Gly Val Glu Val His Asn Ala Lys Thr Lys Pro Arg Glu
65                  70                  75                  80

Glu Gln Phe Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Gly Leu Pro Ser Ser Ile Glu Lys Thr Ile Ser Lys Ala Lys Gly
        115                 120                 125

Gln Pro Arg Glu Pro Gln Val Tyr Thr Leu Pro Pro Ser Gln Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Arg Leu Thr Val Asp Lys Ser Arg Trp Gln Glu Gly Asn
        195                 200                 205

Val Phe Ser Cys Ser Val Met His Glu Ala Leu His Asn His Tyr Thr
    210                 215                 220

```
Gln Lys Ser Leu Ser Leu Ser Leu Gly Lys
225                 230

<210> SEQ ID NO 44
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 44

Val Asp Lys Arg Val Glu Ser Lys Tyr Gly Pro Pro Cys Pro Pro Cys
1               5                   10                  15

Pro Ala Pro Glu Phe Leu Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser Gln Glu Asp Pro Glu Glu Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Gln Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Glu Gly Asn Val Phe Ser
        195                 200                 205

Cys Ser Val Met His Glu Ala Leu His Asn His Tyr Thr Gln Lys Ser
    210                 215                 220

Leu Ser Leu Ser Leu Gly Lys
225                 230

<210> SEQ ID NO 45
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 45

Val Asp Lys Arg Val Glu Ser Lys Tyr Gly Pro Pro Cys Pro Pro Cys
1               5                   10                  15

Pro Ala Pro Glu Phe Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser Gln Glu Asp Pro Glu Glu Gln Phe Asn Trp
    50                  55                  60
```

Tyr Val Asp Gly Val Glu Val His Asn Ala Lys Thr Lys Pro Arg Glu
65                  70                  75                  80

Glu Gln Phe Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Gly Leu Pro Ser Ser Ile Glu Lys Thr Ile Ser Lys Ala Lys Gly
        115                 120                 125

Gln Pro Arg Glu Pro Gln Val Tyr Thr Leu Pro Pro Ser Gln Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Arg Leu Thr Val Asp Lys Ser Arg Trp Gln Glu Gly Asn
        195                 200                 205

Val Phe Ser Cys Ser Val Met His Glu Ala Leu His Asn His Tyr Thr
    210                 215                 220

Gln Lys Ser Leu Ser Leu Ser Leu Gly Lys
225                 230

<210> SEQ ID NO 46
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 46

Val Asp Lys Arg Val Glu Ser Lys Tyr Gly Pro Pro Cys Pro Pro Cys
1               5                   10                  15

Pro Ala Pro Glu Phe Leu Gly Gly Pro Ser Val Phe Leu Phe Pro Pro
                20                  25                  30

Lys Pro Lys Asp Thr Leu Met Ile Ser Arg Thr Pro Glu Val Thr Cys
            35                  40                  45

Val Val Val Asp Val Ser Gln Glu Asp Pro Glu Val Gln Phe Asn Trp
        50                  55                  60

Tyr Val Asp Gly Val Glu Val His Asn Ala Lys Thr Lys Pro Arg Glu
65                  70                  75                  80

Glu Gln Phe Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Gly Leu Pro Ser Ser Ile Glu Lys Thr Ile Ser Lys Ala Lys Gly
        115                 120                 125

Gln Pro Arg Glu Pro Gln Val Tyr Thr Leu Pro Pro Ser Gln Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

```
Leu Tyr Ser Arg Leu Thr Val Asp Lys Ser Arg Trp Gln Glu Gly Asn
            195                 200                 205

Val Phe Ser Cys Ser Val Met His Glu Ala Leu His Asn His Tyr Thr
    210                 215                 220

Gln Lys Ser Leu Ser Leu Ser Leu Gly Lys
225                 230

<210> SEQ ID NO 47
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 47

Val Asp Lys Arg Val Glu Ser Lys Tyr Gly Pro Pro Cys Pro Pro Cys
1               5                   10                  15

Pro Ala Pro Glu Phe Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser Gln Glu Asp Pro Glu Val Gln Phe Asn Trp
 50                  55                  60

Tyr Val Asp Gly Val Glu Val His Asn Ala Lys Thr Lys Pro Arg Glu
65                  70                  75                  80

Glu Gln Phe Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Gly Phe Pro Ser Ser Ile Glu Lys Thr Ile Ser Lys Ala Lys Gly
        115                 120                 125

Gln Pro Arg Glu Pro Gln Val Tyr Thr Leu Pro Pro Ser Gln Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Arg Leu Thr Val Asp Lys Ser Arg Trp Gln Glu Gly Asn
        195                 200                 205

Val Phe Ser Cys Ser Val Met His Glu Ala Leu His Asn His Tyr Thr
    210                 215                 220

Gln Lys Ser Leu Ser Leu Ser Leu Gly Lys
225                 230

<210> SEQ ID NO 48
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 48

Val Asp Lys Arg Val Glu Ser Lys Tyr Gly Pro Pro Cys Pro Pro Cys
1               5                   10                  15

Pro Ala Pro Glu Phe Leu Gly Gly Pro Ser Val Phe Leu Phe Pro Pro
```

```
                 20                  25                  30
Lys Pro Lys Asp Thr Leu Met Ile Ser Arg Thr Pro Glu Val Thr Cys
             35                  40                  45

Val Val Val Asp Val Glu Gln Glu Asp Pro Glu Val Gln Phe Asn Trp
         50                  55                  60

Tyr Val Asp Gly Val Glu Val His Asn Ala Lys Thr Lys Pro Arg Glu
 65                  70                  75                  80

Glu Gln Phe Asn Ser Thr Tyr Arg Val Val Ser Val Leu Thr Val Leu
                 85                  90                  95

His Gln Asp Trp Leu Asn Gly Lys Glu Tyr Lys Cys Lys Val Ser Asn
            100                 105                 110

Lys Gly Phe Pro Ser Ser Ile Glu Lys Thr Ile Ser Lys Ala Lys Gly
        115                 120                 125

Gln Pro Arg Glu Pro Gln Val Tyr Thr Leu Pro Pro Ser Gln Glu Glu
    130                 135                 140

Met Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Arg Leu Thr Val Asp Lys Ser Arg Trp Gln Glu Gly Asn
        195                 200                 205

Val Phe Ser Cys Ser Val Met His Glu Ala Leu His Asn His Tyr Thr
    210                 215                 220

Gln Lys Ser Leu Ser Leu Ser Leu Gly Lys
225                 230

<210> SEQ ID NO 49
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 49

Val Asp Lys Arg Val Glu Ser Lys Tyr Gly Pro Pro Cys Pro Pro Cys
  1               5                  10                  15

Pro Ala Pro Glu Val Ser Ser Val Phe Leu Phe Pro Pro Lys Pro Lys
             20                  25                  30

Asp Thr Leu Met Ile Ser Arg Thr Pro Glu Val Thr Cys Val Val Val
         35                  40                  45

Asp Val Ser Gln Glu Asp Pro Glu Val Gln Phe Asn Trp Tyr Val Asp
     50                  55                  60

Gly Val Glu Val His Asn Ala Lys Thr Lys Pro Arg Glu Glu Gln Phe
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Gly Phe
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Gln Glu Glu Met Thr Lys
    130                 135                 140

Asn Gln Val Ser Leu Thr Cys Leu Val Lys Gly Phe Tyr Pro Ser Asp
```

```
                145                 150                 155                 160
Ile Ala Val Glu Trp Glu Ser Asn Gly Gln Pro Glu Asn Asn Tyr Lys
                    165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
            210                 215                 220

Leu Ser Leu Ser Leu Gly Lys
225                 230

<210> SEQ ID NO 50
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 50

Val Asp Lys Arg Val Glu Ser Lys Tyr Gly Pro Pro Cys Pro Pro Cys
1               5                   10                  15

Pro Ala Pro Glu Phe Leu Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Glu Gln Glu Asp Pro Glu Val Gln Phe Asn Trp Tyr Val Asp
        50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Gln Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Glu Gly Asn Val Phe Ser
        195                 200                 205

Cys Ser Val Met His Glu Ala Leu His Asn His Tyr Thr Gln Lys Ser
    210                 215                 220

Leu Ser Leu Ser Leu Gly Lys
225                 230

<210> SEQ ID NO 51
<211> LENGTH: 231
<212> TYPE: PRT
<213> ORGANISM: Artificial Sequence
<220> FEATURE:
<223> OTHER INFORMATION: Synthetic polypeptide
```

<400> SEQUENCE: 51

Val Asp Lys Arg Val Glu Ser Lys Tyr Gly Pro Pro Cys Pro Pro Cys
1               5                   10                  15

Pro Ala Pro Glu Phe Leu Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser Gln Glu Asp Pro Glu Val Gln Phe Asn Trp Tyr Val Asp
        50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Phe
                100                 105                 110

Pro Ser Ser Ile Glu Lys Thr Ile Ser Lys Ala Lys Gly Gln Pro Arg
            115                 120                 125

Glu Pro Gln Val Tyr Thr Leu Pro Pro Ser Gln Glu Glu Met Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Glu Gly Asn Val Phe Ser
            195                 200                 205

Cys Ser Val Met His Glu Ala Leu His Asn His Tyr Thr Gln Lys Ser
210                 215                 220

Leu Ser Leu Ser Leu Gly Lys
225                 230

<210> SEQ ID NO 52
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 52

Val Asp Lys Arg Val Glu Ser Lys Tyr Gly Pro Pro Cys Pro Pro Cys
1               5                   10                  15

Pro Ala Pro Glu Phe Leu Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Glu Gln Glu Asp Pro Glu Val Gln Phe Asn Trp Tyr Val Asp
        50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Phe
                100                 105                 110

```
Pro Ser Ser Ile Glu Lys Thr Ile Ser Lys Ala Lys Gly Gln Pro Arg
            115                 120                 125

Glu Pro Gln Val Tyr Thr Leu Pro Pro Ser Gln Glu Glu Met Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Glu Gly Asn Val Phe Ser
        195                 200                 205

Cys Ser Val Met His Glu Ala Leu His Asn His Tyr Thr Gln Lys Ser
210                 215                 220

Leu Ser Leu Ser Leu Gly Lys
225                 230

<210> SEQ ID NO 53
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 53

Val Asp Lys Arg Val Glu Ser Lys Tyr Gly Pro Pro Cys Pro Pro Cys
1               5                   10                  15

Pro Ala Pro Glu Phe Leu Gly Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser Gln Glu Asp Pro Glu Val Gln Phe Asn Trp Tyr Val
50                  55                  60

Asp Gly Val Glu Val His Asn Ala Lys Thr Lys Pro Arg Glu Glu Gln
65                  70                  75                  80

Phe Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Arg Leu Thr Val Asp Lys Ser Arg Trp Gln Glu Gly Asn Val Phe
        195                 200                 205

Ser Cys Ser Val Met His Glu Ala Leu His Asn His Tyr Thr Gln Lys
210                 215                 220

Ser Leu Ser Leu Ser Leu Gly Lys
225                 230
```

```
<210> SEQ ID NO 54
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 54

Val Asp Lys Arg Val Glu Ser Lys Tyr Gly Pro Pro Cys Pro Pro Cys
1               5                   10                  15

Pro Ala Pro Glu Phe Leu Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Glu Gln Phe Asn Trp Tyr
50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 55
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 55

Val Asp Lys Arg Val Glu Ser Lys Tyr Gly Pro Pro Cys Pro Pro Cys
1               5                   10                  15

Pro Ala Pro Glu Phe Leu Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Glu Gln Glu Asp Pro Glu Val Gln Phe Asn Trp Tyr
50                  55                  60

Val Asp Gly Val Glu Val His Asn Ala Lys Thr Lys Pro Arg Glu Glu
65                  70                  75                  80
```

```
Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Leu Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 56
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 56

Val Asp Lys Arg Val Glu Ser Lys Tyr Gly Pro Pro Cys Pro Pro Cys
1               5                   10                  15

Pro Ala Pro Glu Phe Leu Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Phe Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205
```

```
Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 57
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 57

Val Asp Lys Arg Val Glu Ser Lys Tyr Gly Pro Pro Cys Pro Pro Cys
1               5                   10                  15

Pro Ala Pro Glu Phe Leu Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Glu Gln Glu Asp Pro Glu Val Gln Phe Asn Trp Tyr
    50                  55                  60

Val Asp Gly Val Glu Val His Asn Ala Lys Thr Lys Pro Arg Glu Glu
65                  70                  75                  80

Gln Phe Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Gly Phe Pro Ser Ser Ile Glu Lys Thr Ile Ser Lys Ala Lys Gly Gln
        115                 120                 125

Pro Arg Glu Pro Gln Val Tyr Thr Leu Pro Pro Ser Gln Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Arg Leu Thr Val Asp Lys Ser Arg Trp Gln Glu Gly Asn Val
        195                 200                 205

Phe Ser Cys Ser Val Met His Glu Ala Leu His Asn His Tyr Thr Gln
    210                 215                 220

Lys Ser Leu Ser Leu Ser Leu Gly Lys
225                 230

<210> SEQ ID NO 58
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 58

Val Asp Lys Arg Val Glu Ser Lys Tyr Gly Pro Pro Cys Pro Pro Cys
1               5                   10                  15

Pro Ala Pro Glu Phe Leu Pro Ser Val Phe Leu Phe Pro Pro Lys Pro
            20                  25                  30

Lys Asp Thr Leu Met Ile Ser Arg Thr Pro Glu Val Thr Cys Val Val
```

-continued

```
                35                  40                  45
Val Asp Val Ser Gln Glu Asp Pro Glu Val Gln Phe Asn Trp Tyr Val
 50                  55                  60
Asp Gly Val Glu Val His Asn Ala Lys Thr Lys Pro Arg Glu Glu Gln
 65                  70                  75                  80
Phe Asn Ser Thr Tyr Arg Val Val Ser Val Leu Thr Val Leu His Gln
                 85                  90                  95
Asp Trp Leu Asn Gly Lys Glu Tyr Lys Cys Lys Val Ser Asn Lys Gly
                100                 105                 110
Leu Pro Ser Ser Ile Glu Lys Thr Ile Ser Lys Ala Lys Gly Gln Pro
            115                 120                 125
Arg Glu Pro Gln Val Tyr Thr Leu Pro Pro Ser Gln Glu Glu Met Thr
130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
                180                 185                 190
Ser Arg Leu Thr Val Asp Lys Ser Arg Trp Gln Glu Gly Asn Val Phe
            195                 200                 205
Ser Cys Ser Val Met His Glu Ala Leu His Asn His Tyr Thr Gln Lys
210                 215                 220
Ser Leu Ser Leu Ser Leu Gly Lys
225                 230

<210> SEQ ID NO 59
<211> LENGTH: 234
<212> TYPE: PRT
<213> ORGANISM: Artificial Sequence
<220> FEATURE:
<223> OTHER INFORMATION: Synthetic polypeptide

<400> SEQUENCE: 59

Val Asp Lys Arg Val Glu Ser Lys Tyr Gly Pro Pro Cys Pro Pro Cys
  1               5                  10                  15
Pro Ala Pro Glu Phe Glu Gly Gly Pro Ser Val Phe Leu Phe Pro Pro
                 20                  25                  30
Lys Pro Lys Asp Thr Leu Met Ile Ser Arg Thr Pro Glu Val Thr Cys
             35                  40                  45
Val Val Val Asp Val Ser Gln Glu Asp Pro Glu Val Gln Phe Asn Trp
 50                  55                  60
Tyr Val Asp Gly Val Glu Val His Asn Ala Lys Thr Lys Pro Arg Glu
 65                  70                  75                  80
Glu Gln Phe Asn Ser Thr Tyr Arg Val Val Ser Val Leu Thr Val Leu
                 85                  90                  95
His Gln Asp Trp Leu Asn Gly Lys Glu Tyr Lys Cys Lys Val Ser Asn
                100                 105                 110
Lys Gly Leu Pro Ser Ser Ile Glu Lys Thr Ile Ser Lys Ala Lys Gly
            115                 120                 125
Gln Pro Arg Glu Pro Gln Val Tyr Thr Leu Pro Pro Ser Gln Glu Glu
        130                 135                 140
Met Thr Lys Asn Gln Val Ser Leu Thr Cys Leu Val Lys Gly Phe Tyr
145                 150                 155                 160
Pro Ser Asp Ile Ala Val Glu Trp Glu Ser Asn Gly Gln Pro Glu Asn
```

```
                        165                 170                 175
Asn Tyr Lys Thr Thr Pro Pro Val Leu Asp Ser Asp Gly Ser Phe Phe
                180                 185                 190

Leu Tyr Ser Arg Leu Thr Val Asp Lys Ser Arg Trp Gln Glu Gly Asn
            195                 200                 205

Val Phe Ser Cys Ser Val Met His Glu Ala Leu His Asn His Tyr Thr
        210                 215                 220

Gln Lys Ser Leu Ser Leu Ser Leu Gly Lys
225                 230

<210> SEQ ID NO 60
<211> LENGTH: 209
<212> TYPE: PRT
<213> ORGANISM: Artificial Sequence
<220> FEATURE:
<223> OTHER INFORMATION: Synthetic polypeptide

<400> SEQUENCE: 60

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys

<210> SEQ ID NO 61
<211> LENGTH: 209
<212> TYPE: PRT
<213> ORGANISM: Artificial Sequence
<220> FEATURE:
<223> OTHER INFORMATION: Synthetic polypeptide

<400> SEQUENCE: 61

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
```

```
                    20                  25                  30
Trp Ile Ser Trp Val Arg Gln Met Pro Gly Lys Gly Leu Glu Trp Met
                35                  40                  45
Gly Lys Ile Tyr Pro Gly Asp Ser Tyr Thr Asn Tyr Ser Pro Ser Phe
             50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Gly Tyr Gly Ile Phe Asp Tyr Trp Gly Gln Gly Thr Leu Val
                100                 105                 110
Thr Val Ser Ser Ala Ser Thr Lys Gly Pro Ser Val Phe Pro Leu Ala
            115                 120                 125
Pro Cys Ser Arg Ser Thr Ser Glu Ser Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Asn Phe
            180                 185                 190
Gly Thr Gln Thr Tyr Thr Cys Asn Val Asp His Lys Pro Ser Asn Thr
            195                 200                 205
Lys

<210> SEQ ID NO 62
<211> LENGTH: 209
<212> TYPE: PRT
<213> ORGANISM: Artificial Sequence
<220> FEATURE:
<223> OTHER INFORMATION: Synthetic polypeptide

<400> SEQUENCE: 62

Glu Val Gln Leu Val Gln Ser Gly Ala Glu Val Lys Lys Pro Gly Glu
 1                   5                  10                  15
Ser Leu Arg Ile Ser Cys Lys Gly Ser Gly Tyr Ser Phe Ser Thr Tyr
                20                  25                  30
Trp Ile Ser Trp Val Arg Gln Met Pro Gly Lys Gly Leu Glu Trp Met
                35                  40                  45
Gly Lys Ile Tyr Pro Gly Asp Ser Tyr Thr Asn Tyr Ser Pro Ser Phe
             50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Gly Tyr Gly Ile Phe Asp Tyr Trp Gly Gln Gly Thr Leu Val
                100                 105                 110
Thr Val Ser Ser Ala Ser Thr Lys Gly Pro Ser Val Phe Pro Leu Ala
            115                 120                 125
Pro Cys Ser Arg Ser Thr Ser Glu Ser Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
                180                 185                 190

Gly Thr Lys Thr Tyr Thr Cys Asn Val Asp His Lys Pro Ser Asn Thr
            195                 200                 205

Lys

<210> SEQ ID NO 63
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 63

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 64
<211> LENGTH: 62
<212> TYPE: PRT
<213> ORGANISM: Mus musculus

<400> SEQUENCE: 64

Val Asp Lys Lys Ile Val Pro Arg Asp Cys Gly Cys Lys Pro Cys Ile
1               5                   10                  15

Cys Thr Val Pro Glu Val Ser Ser Val Phe Ile Phe Pro Pro Thr Cys
            20                  25                  30

Val Val Val Asp Ile Ser Lys Asp Asp Pro Glu Val Gln Phe Ser Trp
        35                  40                  45

Phe Lys Cys Arg Val Asn Ser Ala Ala Phe Pro Ala Pro Ile
```

<210> SEQ ID NO 65
<211> LENGTH: 68
<212> TYPE: PRT
<213> ORGANISM: Mus musculus

<400> SEQUENCE: 65

Val Asp Lys Lys Ile Glu Pro Arg Gly Pro Thr Ile Lys Pro Cys Pro
1               5                   10                  15

Pro Cys Lys Cys Pro Ala Pro Asn Leu Leu Gly Gly Pro Ser Val Phe
            20                  25                  30

Ile Phe Pro Pro Thr Cys Val Val Val Asp Val Ser Glu Asp Asp Pro
        35                  40                  45

Asp Val Gln Ile Ser Trp Phe Lys Cys Lys Val Asn Asn Lys Asp Leu
    50                  55                  60

Pro Ala Pro Ile
65

<210> SEQ ID NO 66
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 66

Lys Arg Val Glu Ser Lys Tyr Gly Pro Pro Cys Pro Pro Cys Pro Ala
1               5                   10                  15

Pro Glu Phe Leu Ser Val Phe Leu Phe Pro Pro Thr Cys Val Val Val
            20                  25                  30

Asp Val Ser Gln Glu Asp Pro Glu Gln Phe Asn Trp Tyr Lys Cys
    35                  40                  45

Lys Val Ser Asn Lys Gly Leu Pro Ser Ser Ile
    50                  55

<210> SEQ ID NO 67
<211> LENGTH: 67
<212> TYPE: PRT
<213> ORGANISM: Homo sapiens

<400> SEQUENCE: 67

Val Asp Lys Lys Val Glu Pro Lys Ser Cys Asp Lys Thr His Thr Cys
1               5                   10                  15

Pro Pro Cys Pro Ala Pro Glu Leu Leu Gly Gly Pro Ser Val Phe Leu
            20                  25                  30

Phe Pro Pro Thr Cys Val Val Val Asp Val Ser His Glu Asp Pro Glu
        35                  40                  45

Val Lys Phe Asn Trp Tyr Lys Cys Lys Val Ser Asn Lys Ala Leu Pro
    50                  55                  60

Ala Pro Ile
65

<210> SEQ ID NO 68
<211> LENGTH: 63
<212> TYPE: PRT
<213> ORGANISM: Homo sapiens

<400> SEQUENCE: 68

Val Asp Lys Thr Val Glu Arg Lys Cys Cys Val Glu Cys Pro Pro Cys

```
                1               5                   10                  15
            Pro Ala Pro Pro Val Ala Gly Pro Ser Val Phe Leu Phe Pro Pro Thr
                            20                  25                  30

Cys Val Val Asp Val Ser His Glu Asp Pro Glu Val Gln Phe Asn
                        35                  40                  45

Trp Tyr Lys Cys Lys Val Ser Asn Lys Gly Leu Pro Ala Pro Ile
                50                  55                  60
```

<210> SEQ ID NO 69
<211> LENGTH: 64
<212> TYPE: PRT
<213> ORGANISM: Homo sapiens

<400> SEQUENCE: 69

```
            Val Asp Lys Arg Val Glu Ser Lys Tyr Gly Pro Pro Cys Pro Ser Cys
            1               5                   10                  15

Pro Ala Pro Glu Phe Leu Gly Gly Pro Ser Val Phe Leu Phe Pro Pro
                            20                  25                  30

Thr Cys Val Val Val Asp Val Ser Gln Glu Asp Pro Glu Val Gln Phe
                        35                  40                  45

Asn Trp Tyr Lys Cys Lys Val Ser Asn Lys Gly Leu Pro Ser Ser Ile
                50                  55                  60
```

<210> SEQ ID NO 70
<211> LENGTH: 67
<212> TYPE: PRT
<213> ORGANISM: Homo sapiens

<400> SEQUENCE: 70

```
            Val Asp Lys Lys Val Glu Pro Lys Ser Cys Asp Lys Thr His Thr Cys
            1               5                   10                  15

Pro Pro Cys Pro Ala Pro Glu Leu Leu Gly Gly Pro Ser Val Phe Leu
                            20                  25                  30

Phe Pro Pro Thr Cys Val Val Val Asp Val Ser His Glu Asp Pro Glu
                        35                  40                  45

Val Lys Phe Asn Trp Tyr Lys Cys Lys Val Ser Asn Lys Ala Leu Pro
                50                  55                  60

Ala Pro Ile
            65
```

<210> SEQ ID NO 71
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 71

```
            Lys Val Glu Pro Lys Ser Cys Asp Lys Thr His Thr Cys Pro Pro Cys
            1               5                   10                  15

Pro Ala Pro Glu Leu Leu Ser Val Phe Leu Phe Pro Pro Thr Cys Val
                            20                  25                  30

Val Val Asp Val Ser His Glu Asp Pro Glu Val Lys Phe Asn Trp Tyr
                        35                  40                  45

Lys Cys Lys Val Ser Asn Lys Ala Leu Pro Ala Pro Ile
                50                  55                  60
```

<210> SEQ ID NO 72
<211> LENGTH: 63

```
<212> TYPE: PRT
<213> ORGANISM: Artificial Sequence
<220> FEATURE:
<223> OTHER INFORMATION: Synthetic polypeptide

<400> SEQUENCE: 72

Lys Val Glu Pro Lys Ser Cys Asp Lys Thr His Thr Cys Pro Pro Cys
1               5                   10                  15

Pro Ala Pro Glu Leu Leu Gly Pro Ser Val Phe Leu Phe Pro Pro Thr
            20                  25                  30

Cys Val Val Val Asp Val Ser His Glu Asp Pro Glu Val Lys Phe Asn
        35                  40                  45

Trp Tyr Lys Cys Lys Val Ser Asn Lys Ala Leu Pro Ala Pro Ile
    50                  55                  60

<210> SEQ ID NO 73
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 73

Lys Lys Val Glu Pro Lys Cys Cys Val Glu Cys Pro Pro Cys Pro Ala
1               5                   10                  15

Pro Glu Leu Leu Gly Gly Pro Ser Val Phe Leu Phe Pro Pro Thr Cys
            20                  25                  30

Val Val Val Asp Val Ser His Glu Asp Pro Glu Val Lys Phe Asn Trp
        35                  40                  45

Tyr Lys Cys Lys Val Ser Asn Lys Ala Leu Pro Ala Pro Ile
    50                  55                  60

<210> SEQ ID NO 74
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 74

Lys Lys Val Glu Pro Lys Tyr Gly Pro Pro Cys Pro Pro Cys Pro Ala
1               5                   10                  15

Pro Glu Leu Leu Gly Gly Pro Ser Val Phe Leu Phe Pro Pro Thr Cys
            20                  25                  30

Val Val Val Asp Val Ser His Glu Asp Pro Glu Val Lys Phe Asn Trp
        35                  40                  45

Tyr Lys Cys Lys Val Ser Asn Lys Ala Leu Pro Ala Pro Ile
    50                  55                  60

<210> SEQ ID NO 75
<211> LENGTH: 64
<212> TYPE: PRT
<213> ORGANISM: Artificial Sequence
<220> FEATURE:
<223> OTHER INFORMATION: Synthetic polypeptide

<400> SEQUENCE: 75

Lys Val Glu Pro Lys Ser Cys Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30
```

Thr Cys Val Val Asp Val Ser His Glu Asp Pro Glu Lys Phe
            35                  40                  45

Asn Trp Tyr Lys Cys Lys Val Ser Asn Lys Ala Leu Pro Ala Pro Ile
 50                  55                  60

<210> SEQ ID NO 76
<211> LENGTH: 64
<212> TYPE: PRT
<213> ORGANISM: Artificial Sequence
<220> FEATURE:
<223> OTHER INFORMATION: Synthetic polypeptide

<400> SEQUENCE: 76

Lys Val Glu Pro Lys Ser Cys Asp Lys Thr His Thr Cys Pro Pro Cys
 1               5                  10                  15

Pro Ala Pro Glu Leu Leu Gly Gly Pro Ser Val Phe Leu Phe Pro Pro
            20                  25                  30

Thr Cys Val Val Asp Val Glu His Glu Asp Pro Glu Val Lys Phe
            35                  40                  45

Asn Trp Tyr Lys Cys Lys Val Ser Asn Lys Ala Leu Pro Ala Pro Ile
 50                  55                  60

<210> SEQ ID NO 77
<211> LENGTH: 64
<212> TYPE: PRT
<213> ORGANISM: Artificial Sequence
<220> FEATURE:
<223> OTHER INFORMATION: Synthetic polypeptide

<400> SEQUENCE: 77

Lys Val Glu Pro Lys Ser Cys Asp Lys Thr His Thr Cys Pro Pro Cys
 1               5                  10                  15

Pro Ala Pro Glu Leu Leu Gly Gly Pro Ser Val Phe Leu Phe Pro Pro
            20                  25                  30

Thr Cys Val Val Asp Val Ser His Glu Asp Pro Glu Val Lys Phe
            35                  40                  45

Asn Trp Tyr Lys Cys Lys Val Ser Asn Lys Ala Phe Pro Ala Pro Ile
 50                  55                  60

<210> SEQ ID NO 78
<211> LENGTH: 64
<212> TYPE: PRT
<213> ORGANISM: Artificial Sequence
<220> FEATURE:
<223> OTHER INFORMATION: Synthetic polypeptide

<400> SEQUENCE: 78

Lys Val Glu Pro Lys Ser Cys Asp Lys Thr His Thr Cys Pro Pro Cys
 1               5                  10                  15

Pro Ala Pro Glu Leu Leu Gly Gly Pro Ser Val Phe Leu Phe Pro Pro
            20                  25                  30

Thr Cys Val Val Asp Val Glu His Glu Asp Pro Glu Val Lys Phe
            35                  40                  45

Asn Trp Tyr Lys Cys Lys Val Ser Asn Lys Ala Phe Pro Ala Pro Ile
 50                  55                  60

<210> SEQ ID NO 79
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 79

Lys Val Glu Pro Lys Ser Cys Asp Lys Thr His Thr Cys Pro Pro Cys
1               5                   10                  15

Pro Ala Pro Glu Leu Leu Ser Val Phe Leu Phe Pro Pro Thr Cys Val
            20                  25                  30

Val Val Asp Val Ser His Glu Asp Pro Glu Glu Lys Phe Asn Trp Tyr
        35                  40                  45

Lys Cys Lys Val Ser Asn Lys Ala Leu Pro Ala Pro Ile
    50                  55                  60

<210> SEQ ID NO 80
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 80

Lys Val Glu Pro Lys Ser Cys Asp Lys Thr His Thr Cys Pro Pro Cys
1               5                   10                  15

Pro Ala Pro Glu Leu Leu Ser Val Phe Leu Phe Pro Pro Thr Cys Val
            20                  25                  30

Val Val Asp Val Glu His Glu Asp Pro Glu Val Lys Phe Asn Trp Tyr
        35                  40                  45

Lys Cys Lys Val Ser Asn Lys Ala Leu Pro Ala Pro Ile
    50                  55                  60

<210> SEQ ID NO 81
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 81

Lys Val Glu Pro Lys Ser Cys Asp Lys Thr His Thr Cys Pro Pro Cys
1               5                   10                  15

Pro Ala Pro Glu Leu Leu Ser Val Phe Leu Phe Pro Pro Thr Cys Val
            20                  25                  30

Val Val Asp Val Ser His Glu Asp Pro Glu Val Lys Phe Asn Trp Tyr
        35                  40                  45

Lys Cys Lys Val Ser Asn Lys Ala Phe Pro Ala Pro Ile
    50                  55                  60

<210> SEQ ID NO 82
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 82

Lys Val Glu Pro Lys Ser Cys Asp Lys Thr His Thr Cys Pro Pro Cys
1               5                   10                  15

Pro Ala Pro Glu Leu Leu Ser Val Phe Leu Phe Pro Pro Thr Cys Val
            20                  25                  30

Val Val Asp Val Glu His Glu Asp Pro Glu Val Lys Phe Asn Trp Tyr
        35                  40                  45

Lys Cys Lys Val Ser Asn Lys Ala Phe Pro Ala Pro Ile

<210> SEQ ID NO 83
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 83

Lys Val Glu Pro Lys Ser Cys Asp Lys Thr His Thr Cys Pro Pro Cys
1               5                   10                  15

Pro Ala Pro Glu Leu Leu Gly Pro Ser Val Phe Leu Phe Pro Pro Thr
            20                  25                  30

Cys Val Val Val Asp Val Ser His Glu Asp Pro Glu Glu Lys Phe Asn
        35                  40                  45

Trp Tyr Lys Cys Lys Val Ser Asn Lys Ala Leu Pro Ala Pro Ile
    50                  55                  60

<210> SEQ ID NO 84
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 84

Lys Val Glu Pro Lys Ser Cys Asp Lys Thr His Thr Cys Pro Pro Cys
1               5                   10                  15

Pro Ala Pro Glu Leu Leu Gly Pro Ser Val Phe Leu Phe Pro Pro Thr
            20                  25                  30

Cys Val Val Val Asp Val Glu His Glu Asp Pro Glu Val Lys Phe Asn
        35                  40                  45

Trp Tyr Lys Cys Lys Val Ser Asn Lys Ala Leu Pro Ala Pro Ile
    50                  55                  60

<210> SEQ ID NO 85
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 85

Lys Val Glu Pro Lys Ser Cys Asp Lys Thr His Thr Cys Pro Pro Cys
1               5                   10                  15

Pro Ala Pro Glu Leu Leu Gly Pro Ser Val Phe Leu Phe Pro Pro Thr
            20                  25                  30

Cys Val Val Val Asp Val Ser His Glu Asp Pro Glu Val Lys Phe Asn
        35                  40                  45

Trp Tyr Lys Cys Lys Val Ser Asn Lys Ala Phe Pro Ala Pro Ile
    50                  55                  60

<210> SEQ ID NO 86
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 86

Lys Val Glu Pro Lys Ser Cys Asp Lys Thr His Thr Cys Pro Pro Cys

```
                1               5                   10                  15
            Pro Ala Pro Glu Leu Leu Gly Pro Ser Val Phe Leu Phe Pro Pro Thr
                            20                  25                  30

Cys Val Val Asp Val Glu His Glu Asp Pro Glu Val Lys Phe Asn
                        35                  40                  45

Trp Tyr Lys Cys Lys Val Ser Asn Lys Ala Phe Pro Ala Pro Ile
                        50                  55                  60

<210> SEQ ID NO 87
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 87

Lys Lys Val Glu Pro Lys Ser Cys Asp Lys Thr His Thr Cys Pro Pro
1               5                   10                  15

Cys Pro Ala Pro Glu Ala Ala Gly Gly Pro Ser Val Phe Leu Phe Pro
            20                  25                  30

Pro Thr Cys Val Val Val Asp Val Ser His Glu Asp Pro Glu Val Lys
        35                  40                  45

Phe Asn Trp Tyr Lys Cys Lys Val Ser Asn Lys Ala Leu Pro Ala Pro
    50                  55                  60

Ile
65

<210> SEQ ID NO 88
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 88

Lys Lys Val Glu Pro Lys Ser Cys Asp Lys Thr His Thr Cys Pro Pro
1               5                   10                  15

Cys Pro Ala Pro Glu Ala Ala Gly Gly Pro Ser Val Phe Leu Phe Pro
            20                  25                  30

Pro Thr Cys Val Val Val Asp Val Ser His Glu Asp Pro Glu Val Lys
        35                  40                  45

Phe Asn Trp Tyr Lys Cys Lys Val Ser Asn Lys Ala Leu Gly Ala Pro
    50                  55                  60

Ile
65

<210> SEQ ID NO 89
<211> LENGTH: 63
<212> TYPE: PRT
<213> ORGANISM: Homo sapiens

<400> SEQUENCE: 89

Val Asp Lys Thr Val Glu Arg Lys Cys Cys Val Glu Cys Pro Pro Cys
1               5                   10                  15

Pro Ala Pro Pro Val Ala Gly Pro Ser Val Phe Leu Phe Pro Pro Thr
            20                  25                  30

Cys Val Val Val Asp Val Ser His Glu Asp Pro Glu Val Gln Phe Asn
        35                  40                  45

Trp Tyr Lys Cys Lys Val Ser Asn Lys Gly Leu Pro Ala Pro Ile
```

<210> SEQ ID NO 90
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 90

Thr Val Glu Arg Lys Cys Cys Val Glu Cys Pro Pro Cys Pro Ala Pro
1               5                   10                  15
Pro Val Ala Ser Val Phe Leu Phe Pro Pro Thr Cys Val Val Val Asp
            20                  25                  30
Val Ser His Glu Asp Pro Glu Val Gln Phe Asn Trp Tyr Lys Cys Lys
        35                  40                  45
Val Ser Asn Lys Gly Leu Pro Ala Pro Ile
    50                  55

<210> SEQ ID NO 91
<211> LENGTH: 64
<212> TYPE: PRT
<213> ORGANISM: Artificial Sequence
<220> FEATURE:
<223> OTHER INFORMATION: Synthetic polypeptide

<400> SEQUENCE: 91

Lys Thr Val Glu Arg Lys Ser Cys Asp Lys Thr His Thr Cys Pro Pro
1               5                   10                  15
Cys Pro Ala Pro Pro Val Ala Gly Pro Ser Val Phe Leu Phe Pro Pro
            20                  25                  30
Thr Cys Val Val Val Asp Val Ser His Glu Asp Pro Glu Val Gln Phe
        35                  40                  45
Asn Trp Tyr Lys Cys Lys Val Ser Asn Lys Gly Leu Pro Ala Pro Ile
    50                  55                  60

<210> SEQ ID NO 92
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 92

Thr Val Glu Arg Lys Cys Cys Val Glu Cys Pro Pro Cys Pro Ala Pro
1               5                   10                  15
Pro Phe Leu Gly Gly Pro Ser Val Phe Leu Phe Pro Pro Thr Cys Val
            20                  25                  30
Val Val Asp Val Ser His Glu Asp Pro Glu Val Gln Phe Asn Trp Tyr
        35                  40                  45
Lys Cys Lys Val Ser Asn Lys Gly Leu Pro Ala Pro Ile
    50                  55                  60

<210> SEQ ID NO 93
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 93

Lys Thr Val Glu Arg Lys Tyr Gly Pro Pro Cys Pro Pro Cys Pro Ala

```
1               5                  10                 15
Pro Pro Val Ala Gly Pro Ser Val Phe Leu Phe Pro Thr Cys Val
                20                 25                 30
Val Val Asp Val Ser His Glu Asp Pro Glu Val Gln Phe Asn Trp Tyr
            35                 40                 45
Lys Cys Lys Val Ser Asn Lys Gly Leu Pro Ala Pro Ile
        50                 55                 60
```

<210> SEQ ID NO 94
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 94

```
Thr Val Glu Arg Lys Cys Cys Val Glu Cys Pro Pro Cys Pro Ala Pro
1               5                  10                 15
Pro Val Ala Gly Pro Ser Val Phe Leu Phe Pro Pro Thr Cys Val Val
                20                 25                 30
Val Asp Val Ser His Glu Asp Pro Glu Glu Gln Phe Asn Trp Tyr Lys
            35                 40                 45
Cys Lys Val Ser Asn Lys Gly Leu Pro Ala Pro Ile
        50                 55                 60
```

<210> SEQ ID NO 95
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 95

```
Thr Val Glu Arg Lys Cys Cys Val Glu Cys Pro Pro Cys Pro Ala Pro
1               5                  10                 15
Pro Val Ala Gly Pro Ser Val Phe Leu Phe Pro Pro Thr Cys Val Val
                20                 25                 30
Val Asp Val Glu His Glu Asp Pro Glu Val Gln Phe Asn Trp Tyr Lys
            35                 40                 45
Cys Lys Val Ser Asn Lys Gly Leu Pro Ala Pro Ile
        50                 55                 60
```

<210> SEQ ID NO 96
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 96

```
Thr Val Glu Arg Lys Cys Cys Val Glu Cys Pro Pro Cys Pro Ala Pro
1               5                  10                 15
Pro Val Ala Gly Pro Ser Val Phe Leu Phe Pro Pro Thr Cys Val Val
                20                 25                 30
Val Asp Val Ser His Glu Asp Pro Glu Val Gln Phe Asn Trp Tyr Lys
            35                 40                 45
Cys Lys Val Ser Asn Lys Gly Phe Pro Ala Pro Ile
        50                 55                 60
```

<210> SEQ ID NO 97

```
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 97

Thr Val Glu Arg Lys Cys Cys Val Glu Cys Pro Pro Cys Pro Ala Pro
1               5                   10                  15

Pro Val Ala Gly Pro Ser Val Phe Leu Phe Pro Pro Thr Cys Val Val
            20                  25                  30

Val Asp Val Glu His Glu Asp Pro Glu Val Gln Phe Asn Trp Tyr Lys
        35                  40                  45

Cys Lys Val Ser Asn Lys Gly Phe Pro Ala Pro Ile
    50                  55                  60

<210> SEQ ID NO 98
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 98

Thr Val Glu Arg Lys Cys Cys Val Glu Cys Pro Pro Cys Pro Ala Pro
1               5                   10                  15

Glu Val Ser Ser Val Phe Leu Phe Pro Pro Thr Cys Val Val Val Asp
            20                  25                  30

Val Ser His Glu Asp Pro Glu Val Gln Phe Asn Trp Tyr Lys Cys Lys
        35                  40                  45

Val Ser Asn Lys Gly Phe Pro Ala Pro Ile
    50                  55

<210> SEQ ID NO 99
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 99

Thr Val Glu Arg Lys Cys Cys Val Glu Cys Pro Pro Cys Pro Ala Pro
1               5                   10                  15

Pro Val Ala Ser Val Phe Leu Phe Pro Pro Thr Cys Val Val Val Asp
            20                  25                  30

Val Ser His Glu Asp Pro Glu Gln Phe Asn Trp Tyr Lys Cys Lys
        35                  40                  45

Val Ser Asn Lys Gly Leu Pro Ala Pro Ile
    50                  55

<210> SEQ ID NO 100
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 100

Thr Val Glu Arg Lys Cys Cys Val Glu Cys Pro Pro Cys Pro Ala Pro
1               5                   10                  15

Pro Val Ala Ser Val Phe Leu Phe Pro Pro Thr Cys Val Val Val Asp
            20                  25                  30
```

Val Glu His Glu Asp Pro Glu Val Gln Phe Asn Trp Tyr Lys Cys Lys
        35                  40                  45

Val Ser Asn Lys Gly Leu Pro Ala Pro Ile
    50                  55

<210> SEQ ID NO 101
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 101

Thr Val Glu Arg Lys Cys Cys Val Glu Cys Pro Pro Cys Pro Ala Pro
1               5                   10                  15

Pro Val Ala Ser Val Phe Leu Phe Pro Pro Thr Cys Val Val Val Asp
            20                  25                  30

Val Ser His Glu Asp Pro Glu Val Gln Phe Asn Trp Tyr Lys Cys Lys
        35                  40                  45

Val Ser Asn Lys Gly Phe Pro Ala Pro Ile
    50                  55

<210> SEQ ID NO 102
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 102

Thr Val Glu Arg Lys Cys Cys Val Glu Cys Pro Pro Cys Pro Ala Pro
1               5                   10                  15

Pro Val Ala Ser Val Phe Leu Phe Pro Pro Thr Cys Val Val Val Asp
            20                  25                  30

Val Glu His Glu Asp Pro Glu Val Gln Phe Asn Trp Tyr Lys Cys Lys
        35                  40                  45

Val Ser Asn Lys Gly Phe Pro Ala Pro Ile
    50                  55

<210> SEQ ID NO 103
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 103

Thr Val Glu Arg Lys Cys Cys Val Glu Cys Pro Pro Cys Pro Ala Pro
1               5                   10                  15

Pro Val Ala Pro Ser Val Phe Leu Phe Pro Pro Thr Cys Val Val Val
            20                  25                  30

Asp Val Ser His Glu Asp Pro Glu Val Gln Phe Asn Trp Tyr Lys Cys
        35                  40                  45

Lys Val Ser Asn Lys Gly Leu Pro Ala Pro Ile
    50                  55

<210> SEQ ID NO 104
<211> LENGTH: 59
<212> TYPE: PRT
<213> ORGANISM: Artificial Sequence
<220> FEATURE:

-continued

<223> OTHER INFORMATION: Synthetic polypeptide

<400> SEQUENCE: 104

Thr Val Glu Arg Lys Cys Cys Val Glu Cys Pro Pro Cys Pro Ala Pro
1               5                   10                  15

Pro Val Ala Pro Ser Val Phe Leu Phe Pro Pro Thr Cys Val Val Val
            20                  25                  30

Asp Val Glu His Glu Asp Pro Glu Val Gln Phe Asn Trp Tyr Lys Cys
        35                  40                  45

Lys Val Ser Asn Lys Gly Leu Pro Ala Pro Ile
    50                  55

<210> SEQ ID NO 105
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 105

Thr Val Glu Arg Lys Cys Cys Val Glu Cys Pro Pro Cys Pro Ala Pro
1               5                   10                  15

Pro Val Ala Pro Ser Val Phe Leu Phe Pro Pro Thr Cys Val Val Val
            20                  25                  30

Asp Val Ser His Glu Asp Pro Glu Val Gln Phe Asn Trp Tyr Lys Cys
        35                  40                  45

Lys Val Ser Asn Lys Gly Phe Pro Ala Pro Ile
    50                  55

<210> SEQ ID NO 106
<211> LENGTH: 64
<212> TYPE: PRT
<213> ORGANISM: Homo sapiens

<400> SEQUENCE: 106

Val Asp Lys Arg Val Glu Ser Lys Tyr Gly Pro Pro Cys Pro Ser Cys
1               5                   10                  15

Pro Ala Pro Glu Phe Leu Gly Gly Pro Ser Val Phe Leu Phe Pro Pro
            20                  25                  30

Thr Cys Val Val Val Asp Val Ser Gln Glu Asp Pro Glu Val Gln Phe
        35                  40                  45

Asn Trp Tyr Lys Cys Lys Val Ser Asn Lys Gly Leu Pro Ser Ser Ile
    50                  55                  60

<210> SEQ ID NO 107
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 107

Lys Arg Val Glu Ser Lys Tyr Gly Pro Pro Cys Pro Cys Pro Ala
1               5                   10                  15

Pro Glu Phe Leu Ser Val Phe Leu Phe Pro Pro Thr Cys Val Val Val
            20                  25                  30

Asp Val Ser Gln Glu Asp Pro Glu Val Gln Phe Asn Trp Tyr Lys Cys
        35                  40                  45

Lys Val Ser Asn Lys Gly Leu Pro Ser Ser Ile
    50                  55

<210> SEQ ID NO 108
<211> LENGTH: 65
<212> TYPE: PRT
<213> ORGANISM: Artificial Sequence
<220> FEATURE:
<223> OTHER INFORMATION: Synthetic polypeptide

<400> SEQUENCE: 108

Lys Arg Val Glu Ser Lys Ser Cys Asp Lys Thr His Thr Cys Pro Pro
1               5                   10                  15

Cys Pro Ala Pro Glu Phe Leu Gly Gly Pro Ser Val Phe Leu Phe Pro
            20                  25                  30

Pro Thr Cys Val Val Val Asp Val Ser Gln Glu Asp Pro Glu Val Gln
        35                  40                  45

Phe Asn Trp Tyr Lys Cys Lys Val Ser Asn Lys Gly Leu Pro Ser Ser
    50                  55                  60

Ile
65

<210> SEQ ID NO 109
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 109

Lys Arg Val Glu Ser Lys Tyr Gly Pro Pro Cys Pro Pro Cys Pro Ala
1               5                   10                  15

Pro Glu Phe Leu Gly Pro Ser Val Phe Leu Phe Pro Pro Thr Cys Val
            20                  25                  30

Val Val Asp Val Ser Gln Glu Asp Pro Glu Val Gln Phe Asn Trp Tyr
        35                  40                  45

Lys Cys Lys Val Ser Asn Lys Gly Leu Pro Ser Ser Ile
    50                  55                  60

<210> SEQ ID NO 110
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 110

Lys Arg Val Glu Ser Lys Cys Cys Val Glu Cys Pro Pro Cys Pro Ala
1               5                   10                  15

Pro Glu Phe Leu Gly Gly Pro Ser Val Phe Leu Phe Pro Pro Thr Cys
            20                  25                  30

Val Val Val Asp Val Ser Gln Glu Asp Pro Glu Val Gln Phe Asn Trp
        35                  40                  45

Tyr Lys Cys Lys Val Ser Asn Lys Gly Leu Pro Ser Ser Ile
    50                  55                  60

<210> SEQ ID NO 111
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 111

Lys Arg Val Glu Ser Lys Tyr Gly Pro Pro Cys Pro Pro Cys Pro Ala
1               5                   10                  15

Pro Glu Phe Leu Gly Gly Pro Ser Val Phe Leu Phe Pro Pro Thr Cys
            20                  25                  30

Val Val Val Asp Val Ser Gln Glu Asp Pro Glu Glu Gln Phe Asn Trp
        35                  40                  45

Tyr Lys Cys Lys Val Ser Asn Lys Gly Leu Pro Ser Ser Ile
50                  55                  60

<210> SEQ ID NO 112
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 112

Lys Arg Val Glu Ser Lys Tyr Gly Pro Pro Cys Pro Pro Cys Pro Ala
1               5                   10                  15

Pro Glu Phe Leu Ser Val Phe Leu Phe Pro Pro Thr Cys Val Val Val
            20                  25                  30

Asp Val Ser Gln Glu Asp Pro Glu Glu Gln Phe Asn Trp Tyr Lys Cys
        35                  40                  45

Lys Val Ser Asn Lys Gly Leu Pro Ser Ser Ile
50                  55

<210> SEQ ID NO 113
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 113

Lys Arg Val Glu Ser Lys Tyr Gly Pro Pro Cys Pro Pro Cys Pro Ala
1               5                   10                  15

Pro Glu Phe Leu Gly Pro Ser Val Phe Leu Phe Pro Pro Thr Cys Val
            20                  25                  30

Val Val Asp Val Ser Gln Glu Asp Pro Glu Glu Gln Phe Asn Trp Tyr
        35                  40                  45

Lys Cys Lys Val Ser Asn Lys Gly Leu Pro Ser Ser Ile
50                  55                  60

<210> SEQ ID NO 114
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 114

Lys Arg Val Glu Ser Lys Tyr Gly Pro Pro Cys Pro Pro Cys Pro Ala
1               5                   10                  15

Pro Glu Phe Leu Gly Gly Pro Ser Val Phe Leu Phe Pro Pro Thr Cys
            20                  25                  30

Val Val Val Asp Val Glu Gln Glu Asp Pro Glu Val Gln Phe Asn Trp
        35                  40                  45

Tyr Lys Cys Lys Val Ser Asn Lys Gly Leu Pro Ser Ser Ile
50                  55                  60

```
<210> SEQ ID NO 115
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 115

Lys Arg Val Glu Ser Lys Tyr Gly Pro Pro Cys Pro Pro Cys Pro Ala
1               5                   10                  15

Pro Glu Phe Leu Gly Gly Pro Ser Val Phe Leu Phe Pro Pro Thr Cys
            20                  25                  30

Val Val Val Asp Val Ser Gln Glu Asp Pro Glu Val Gln Phe Asn Trp
        35                  40                  45

Tyr Lys Cys Lys Val Ser Asn Lys Gly Phe Pro Ser Ser Ile
    50                  55                  60

<210> SEQ ID NO 116
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 116

Lys Arg Val Glu Ser Lys Tyr Gly Pro Pro Cys Pro Pro Cys Pro Ala
1               5                   10                  15

Pro Glu Phe Leu Gly Gly Pro Ser Val Phe Leu Phe Pro Pro Thr Cys
            20                  25                  30

Val Val Val Asp Val Glu Gln Glu Asp Pro Glu Val Gln Phe Asn Trp
        35                  40                  45

Tyr Lys Cys Lys Val Ser Asn Lys Gly Phe Pro Ser Ser Ile
    50                  55                  60

<210> SEQ ID NO 117
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 117

Lys Arg Val Glu Ser Lys Tyr Gly Pro Pro Cys Pro Pro Cys Pro Ala
1               5                   10                  15

Pro Glu Val Ser Ser Val Phe Leu Phe Pro Pro Thr Cys Val Val Val
            20                  25                  30

Asp Val Ser Gln Glu Asp Pro Glu Val Gln Phe Asn Trp Tyr Lys Cys
        35                  40                  45

Lys Val Ser Asn Lys Gly Phe Pro Ser Ser Ile
    50                  55

<210> SEQ ID NO 118
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 118

Lys Arg Val Glu Ser Lys Tyr Gly Pro Pro Cys Pro Pro Cys Pro Ala
1               5                   10                  15
```

```
Pro Glu Phe Leu Ser Val Phe Leu Phe Pro Pro Thr Cys Val Val
            20                  25                  30

Asp Val Glu Gln Glu Asp Pro Val Gln Phe Asn Trp Tyr Lys Cys
        35                  40                  45

Lys Val Ser Asn Lys Gly Leu Pro Ser Ser Ile
    50                  55
```

<210> SEQ ID NO 119
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 119

```
Lys Arg Val Glu Ser Lys Tyr Gly Pro Pro Cys Pro Pro Cys Pro Ala
1               5                   10                  15

Pro Glu Phe Leu Ser Val Phe Leu Phe Pro Pro Thr Cys Val Val Val
            20                  25                  30

Asp Val Ser Gln Glu Asp Pro Glu Val Gln Phe Asn Trp Tyr Lys Cys
        35                  40                  45

Lys Val Ser Asn Lys Gly Phe Pro Ser Ser Ile
    50                  55
```

<210> SEQ ID NO 120
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 120

```
Lys Arg Val Glu Ser Lys Tyr Gly Pro Pro Cys Pro Pro Cys Pro Ala
1               5                   10                  15

Pro Glu Phe Leu Ser Val Phe Leu Phe Pro Pro Thr Cys Val Val Val
            20                  25                  30

Asp Val Glu Gln Glu Asp Pro Glu Val Gln Phe Asn Trp Tyr Lys Cys
        35                  40                  45

Lys Val Ser Asn Lys Gly Phe Pro Ser Ser Ile
    50                  55
```

<210> SEQ ID NO 121
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 121

```
Lys Arg Val Glu Ser Lys Tyr Gly Pro Pro Cys Pro Pro Cys Pro Ala
1               5                   10                  15

Pro Glu Phe Leu Gly Ser Val Phe Leu Phe Pro Pro Thr Cys Val Val
            20                  25                  30

Val Asp Val Ser Gln Glu Asp Pro Glu Val Gln Phe Asn Trp Tyr Lys
        35                  40                  45

Cys Lys Val Ser Asn Lys Gly Leu Pro Ser Ser Ile
    50                  55                  60
```

<210> SEQ ID NO 122
<211> LENGTH: 61
<212> TYPE: PRT

<213> ORGANISM: Artificial Sequence
<220> FEATURE:
<223> OTHER INFORMATION: Synthetic polypeptide

<400> SEQUENCE: 122

```
Lys Arg Val Glu Ser Lys Tyr Gly Pro Pro Cys Pro Pro Cys Pro Ala
1               5                   10                  15
Pro Glu Phe Leu Gly Pro Ser Val Phe Leu Phe Pro Pro Thr Cys Val
            20                  25                  30
Val Val Asp Val Ser Gln Glu Asp Pro Glu Glu Gln Phe Asn Trp Tyr
        35                  40                  45
Lys Cys Lys Val Ser Asn Lys Gly Leu Pro Ser Ser Ile
50                  55                  60
```

<210> SEQ ID NO 123
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 123

```
Lys Arg Val Glu Ser Lys Tyr Gly Pro Pro Cys Pro Pro Cys Pro Ala
1               5                   10                  15
Pro Glu Phe Leu Gly Pro Ser Val Phe Leu Phe Pro Pro Thr Cys Val
            20                  25                  30
Val Asp Val Glu Gln Glu Asp Pro Glu Val Gln Phe Asn Trp Tyr
        35                  40                  45
Lys Cys Lys Val Ser Asn Lys Gly Leu Pro Ser Ser Ile
50                  55                  60
```

<210> SEQ ID NO 124
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 124

```
Lys Arg Val Glu Ser Lys Tyr Gly Pro Pro Cys Pro Pro Cys Pro Ala
1               5                   10                  15
Pro Glu Phe Leu Gly Pro Ser Val Phe Leu Phe Pro Pro Thr Cys Val
            20                  25                  30
Val Val Asp Val Ser Gln Glu Asp Pro Glu Val Gln Phe Asn Trp Tyr
        35                  40                  45
Lys Cys Lys Val Ser Asn Lys Gly Phe Pro Ser Ser Ile
50                  55                  60
```

<210> SEQ ID NO 125
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 125

```
Lys Arg Val Glu Ser Lys Tyr Gly Pro Pro Cys Pro Pro Cys Pro Ala
1               5                   10                  15
Pro Glu Phe Leu Gly Pro Ser Val Phe Leu Phe Pro Pro Thr Cys Val
            20                  25                  30
Val Val Asp Val Glu Gln Glu Asp Pro Glu Val Gln Phe Asn Trp Tyr
```

```
                35                  40                  45
Lys Cys Lys Val Ser Asn Lys Gly Phe Pro Ser Ser Ile
    50                  55                  60

<210> SEQ ID NO 126
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 126

Lys Arg Val Glu Ser Lys Tyr Gly Pro Pro Cys Pro Pro Cys Pro Ala
1               5                   10                  15

Pro Glu Phe Leu Pro Ser Val Phe Leu Phe Pro Pro Thr Cys Val Val
                20                  25                  30

Val Asp Val Ser Gln Glu Asp Pro Glu Val Gln Phe Asn Trp Tyr Lys
            35                  40                  45

Cys Lys Val Ser Asn Lys Gly Leu Pro Ser Ser Ile
    50                  55                  60

<210> SEQ ID NO 127
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 127

Lys Arg Val Glu Ser Lys Tyr Gly Pro Pro Cys Pro Pro Cys Pro Ala
1               5                   10                  15

Pro Glu Phe Glu Gly Gly Pro Ser Val Phe Leu Phe Pro Pro Thr Cys
                20                  25                  30

Val Val Val Asp Val Ser Gln Glu Asp Pro Glu Val Gln Phe Asn Trp
            35                  40                  45

Tyr Lys Cys Lys Val Ser Asn Lys Gly Leu Pro Ser Ser Ile
    50                  55                  60

<210> SEQ ID NO 128
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 128

Val Asp Lys Arg Val Glu Ser Lys Tyr Gly Pro Pro Cys Pro Pro Cys
1               5                   10                  15

Pro Ala Pro Glu Phe Leu Ser Val Phe Leu Phe Pro Pro Lys Pro Lys
                20                  25                  30

Asp Thr Leu Met Ile Ser Arg Thr Pro Glu Val Thr Cys Val Val Val
            35                  40                  45

Asp Val Ser Gln Glu Asp Pro Glu Glu Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Gly Leu
            100                 105                 110
```

-continued

```
Pro Ser Ser Ile Glu Lys Thr Ile Ser Lys Ala Lys Gly Gln Pro Arg
        115                 120                 125

Glu Pro Gln Val Tyr Thr Leu Pro Pro Ser Gln Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Leu Gly Lys
225                 230
```

THERAPEUTIC AGENTS AND METHODS FOR ENHANCING IMMUNE RESPONSES IN TUMOR MICROENVIRONMENT

RELATED APPLICATION

This application is a National Stage Application under 35 U.S.C. § 371 of International Application No. PCT/US2018/024872, filed Mar. 28, 2018, which claims the benefit under 35 U.S.C. § 119(e) of the filing date of U.S. provisional application No. 62/477,661, filed Mar. 28, 2017, the content of each of which is incorporated by reference herein in its entirety.

BACKGROUND OF THE INVENTION

Fc receptors (FcR) are a family of immune cell surface proteins capable of binding to the Fc portion of antibodies. There are several different types of Fc receptors, including Fcγ receptors, Fcα receptors, Fcε receptors, and neonatal Fc receptors (FcRn), which have different binding activities to IgG, IgA, IgE, and IgG antibodies, respectively. The Fcγ receptor subfamily includes FcγRI (CD64), FcγRIIA (CD32a), FcγRIIB (CD32b), FcγRIIC (CD32c), FcγRIIIA (CD16a), and FcγRIIIB (CD16b). FcγRI has high binding affinity to IgG1 and IgG3 antibodies, while the other FcγRs have low binding affinity to IgG antibodies.

Different types of Fc receptors play different roles in the immune system. For example, FcγRIII receptors, expressed on NK cells and macrophages, bind to antibodies that are attached to infected cells or invading pathogens and trigger antibody-mediated phagocytosis (ADCP) or antibody-dependent cell-mediated cytotoxicity (ADCC) of the immune cells, thereby leading to elimination of the infected cells or invading pathogens. On the other hand, FcγRII receptors, expressed on B cells and dendritic cells, can down regulate the activity of the immune cells when binding to IgG antibodies.

Therapies involving activated immune cells are promising approaches for eliminating diseased cells such as cancer cells. However, such therapeutic approaches often raise safety concerns. For example, overly activated immune cells would lead to undesired cytotoxicity, causing tissue damage. It is therefore of great interest to develop new immune therapies that are effective and safe.

SUMMARY OF THE INVENTION

The present disclosure is based, at least in part, on the development of various Fc region variants of IgG1, IgG2, or IgG4 molecules that exhibit desired Fc receptor binding activity and/or selectivity. Such Fc variants can be used in constructing Fc-containing proteins such as antibodies capable of selectively modulating immune responses.

Accordingly, one aspect of the present disclosure provides a protein (e.g., an antibody) comprising a variant Fc region, which comprises a mutation (e.g., an amino acid residue substitution, an insertion, a deletion, or a combination thereof) at any of positions 218-329 (e.g., 218-328) as compared to a wild-type parent Fc region. The Fc numbering system used herein is according to the EU index as known in the art.

In some embodiments, the mutation comprises one or more of the following: (a) mutation at one or more of positions 219-225; (b) an insertion between position 218 and position 219, or at position 236; (c) an amino acid residue substitution at one or more positions of 233-235; (d) an insertion at any of positions 220-223; (e) a deletion at one or more of positions 236-238; and (f) an amino acid substitution at one or more of positions 267, 273, 328, and 329 (e.g., S267E, V273E, L328F, P329G, or a combination thereof). In some instances, the mutation comprises an insertion and optionally a deletion. For example, the mutation in the variant Fc region may comprise (i) a mutation at one or more of positions 234-238, and optionally (ii) a mutation at one or more of positions 267, 273, 328, and 329. In some examples, the mutation of (i) can be a deletion, for example, a deletion of one or more of positions 234-238 (e.g., 236-238). Alternatively or in addition, the mutation of (ii) can be an amino acid residue substitution, for example, amino acid residue substitutions S267E, V273E, L328F, P329G, or a combination thereof.

In some embodiments, the wild-type parent Fc region is of an IgG1 molecule. A protein comprising an Fc variant derived from an IgG1 molecule (e.g., a human IgG1 molecule) may comprise a mutation comprising one or more of the following: (a) an insertion between position 228 and position 229; (b) a mutation at one or more of positions 220-225; (c) an amino acid substitution at positions 234 and 235; (d) a deletion at one or more of positions 236-238; and (e) an amino acid substitution at one or more positions 267, 273, 328, and 329 (e.g., S267E, V273E, L328F, and/or P329G). In one example, the mutation comprises (i) a deletion at one or more of positions 236-238 (e.g., 236, 237, 238, or a combination thereof), and optionally (ii) an amino acid residue substitution at one or more of positions 267, 273, and 328. For example, the mutation may comprise a deletion of position 236 or a deletion of positions 236-238. Optionally, the mutation may further comprise an amino acid residue substitution at one or more of positions 267, 273, and 268, which may be S267E, V273E, L328F, or a combination thereof. In one example, the mutation comprises a deletion at one or more of positions 236-238 and the amino acid substitution of S267E. Exemplary variant Fc regions derived from human IgG1 may be one of G1m1, G1m2, G1m-2, G1m-4, G1m5, G1m7, G1m8, G1m9, G1m15, G1m17, G1m18, G1m19, G1m25, G1m27, G1m28, G1m29, G1mAA, and G1mAG.

In other embodiments, the wild-type parent Fc region is of an IgG2 molecule (e.g., a human IgG2 molecule). A protein comprising an Fc variant derived from an IgG2 molecule (e.g., a human IgG2 molecule) may comprise a mutation comprising one or more of the following: (a) a mutation at one or more positions of 219-225; (b) an amino acid substitution at one or more of positions 233-235; (c) an insertion between position 218 and 219, or at position 236; (d) a deletion of one or more of positions 237 and 238; and (e) an amino acid residue substitution at one or more of positions 267, 273, and 328 (e.g., S267E, V273E, L328F, or a combination thereof). In some examples, the mutation is at one or more of positions 233-238, 267, 273, and 328. For example, the mutation may comprise (i) a deletion at one or more of positions 236, 237, and 238 (e.g., 237 and/or 238), and optionally (ii) an amino acid residue substitution at one or more of positions 267, 273, and 328 (e.g., S267E, L328F, or a combination thereof). In some examples, the mutation comprises an addition at position 236. In other examples, the mutation may comprise an amino acid residue substitution at one or more of positions 233-238, e.g., P233E, V234F or V234V, A235L, A235S, or a combination thereof. Alternatively or in addition, the mutation further comprises an amino acid residue substitution at one or more positions 267, 273, and 328, which may be S267E, V273E, and/or L328F. In some particularly examples, the variant Fc region derived from IgG2 can be one of G2m1, G2m-1, G2m2, G2m-4, G2m5, G2m7, G2m8, G2m9, G2m10, G2m15, G2m17, G2m18, G2m19, G2m20, G2m27, G2m27, and G2m28.

In yet other embodiments, the wild-type parent Fc is of an IgG4 molecule (e.g., a human IgG4 molecule). The Fc variant derived from an IgG4 molecule (e.g., a human IgG4) may comprise the S228P substitution. Alternatively or in addition, the Fc variant derived from an IgG4 molecule such as a human IgG4 molecule may have a mutation comprising one or more of the following: (a) a mutation at one or more of positions 219-225; (b) an amino acid residue substitution at one or more positions 234 and 235; (c) a deletion at one or more of positions 236-238; and (d) an amino acid residue substitution at one or more of positions 267, 273, and 328 (S267E, V273F, L328F, or a combination thereof). In some examples, the Fc variants of IgG4 may comprise the S228P amino acid residue substitution and a deletion at one or more of positions 236-238. Such an Fc variant may further comprise an amino acid substitution at one or more of positions 267, 273, and 328 (e.g., L328F). In some instances, the Fc variant may comprise the S228P substitution and a further mutation at one or more positions 234-238, 267, 273, and 328. For example, the mutation may comprise a deletion of one or more of position 235-237, or comprise an amino acid residue substitution at position 235, 236, or both (e.g., F234V, K235S, or a combination thereof). Alternatively or in addition, the mutation further comprises an amino acid residue substitution at one or more positions 267, 273, and 328. Examples include S267E, V273E, L328F, or a combination thereof. In some particular examples, the variant Fc region is one of G4m1, G4m-1, G4m2, G4m-2, G4m3, G4m4, G4m5, G4m7, G4m8, G4m9, G4m10, G4m17, G4m18, G4m19, G4m20, G4m25, G4m27, G4m28, G4m29, G4m30, and G4mPE.

Any of the variant Fc regions described herein may exhibit an enhanced binding activity and/or an enhanced selectivity to FcγRIIB as compared with the parent wild-type Fc region. Alternatively, the variant Fc regions described herein may have low or no binding activity to any of the FcγR receptors. Alternatively or in addition, the variant Fc region binds FcRn.

Also described herein is a protein that comprises a variant Fc region of an IgG2 or IgG4 molecule (e.g., human IgG2 or human IgG4 molecule). Such a variant Fc region may comprise a mutation at position 267, position 273, position 328, or a combination thereof as compared to a wild-type parent IgG2 or IgG4 Fc region. The numbering is according to the EU index.

In another aspect, provided herein is a pharmaceutical composition, comprising a protein that contains any of the variant Fc regions as described herein and a pharmaceutically acceptable carrier. Such a pharmaceutical composition may be used to selectively activate an immune response in a subject.

In yet another aspect, the present disclosure provides a method for selectively activating an immune response in a subject, the method comprising administering to a subject in need thereof an effective amount of a therapeutic agent, wherein the therapeutic agent comprises a first moiety that binds an immune cell receptor and a second moiety that binds FcγRIIB In some examples, the immune cell receptor is a tumor necrosis factor receptor superfamily (TNFSF) member. Examples include, but are not limited to, FAS, TNFRSF12A, 4-1BB/CD137, TNFRSF13B, TNFRSF13C, CD27/TNFRSF7, CD30/TNFRSF8, CD40/TNFRSF5, DR3/TNFRSF25, DR4/TNFRSF10A, DR5/TNFRSF10B, DR6/TNFRSF21, GITR/TNFRSF18, HVEM/TNFRSF14, LTβR, OX40/TNFRSF4, TROY/TNFRSF19, RELT/TNFRSF19L, TNFRSF12A, TNFRSF13B, TL1A/TNFSF15, TNFRSF17, TNFRSF1A, TNFRSF11B, RANK/TNFRSF11A, TNFRSF11B, NGFR, EDA2R, and TNFRSF1B.

In some embodiments the therapeutic agent can be an antibody (e.g., an agonist antibody), which may be an IgG1, IgG2, or IgG4 molecule (e.g., a human IgG1, human IgG2, or human IgG4 molecule).

In some embodiments, the therapeutic agent may selective bind FcγRIIB For example, the therapeutic agent may contain a variant Fc region having a selective binding affinity to FcγRIIB (e.g., any of the variant Fc regions described herein). Alternatively or in addition, the variant Fc region may have an enhanced binding activity to FcγRIIB as compared with a wild-type parent Fc region.

In other embodiments, the therapeutic agent may be a bispecific antibody comprising a first moiety, which is a first antigen-binding fragment specific to the immune cell receptor, and a second moiety, which is a second antigen-binding fragment specific to FcγRIIB In any of the methods described herein, the subject can be a human patient having or suspected of having a cancer. Exemplary cancers include lung cancer, stomach cancer, liver cancer, breast cancer, skin cancer, pancreatic cancer, brain cancer, prostate cancer, bladder cancer, colorectal cancer, sarcoma, bone cancer, lymphoma and a hematological cancer.

Also within the scope of the present disclosure are pharmaceutical compositions for use in enhancing immune responses, comprising a protein that contains any of the variant Fc regions as described herein and a pharmaceutically acceptable carrier, and uses of such proteins for manufacturing the medicament for use in achieving the intended therapeutic purposes, for example, cancer treatment.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

In FIGS. 2B and 2C, the groups, from left to right, correspond to 0.01 μg/ml, 0.03 μg/ml, and 0.1 μg/ml.

FIG. 5G shows the plasma concentrations of G2m19 after an IV dose of 3 mg/kg (top graph) and of G2m1 after an IV dose of 3 mg/kg (bottom graph). FIG. 5H shows the plasma concentrations of G2 (wild type) after an IV dose 3 mg/kg (top graph) and of G1Maa after an IV dose of 3 mg/kg (bottom graph).

DETAILED DESCRIPTION OF THE INVENTION

Figure 1A:
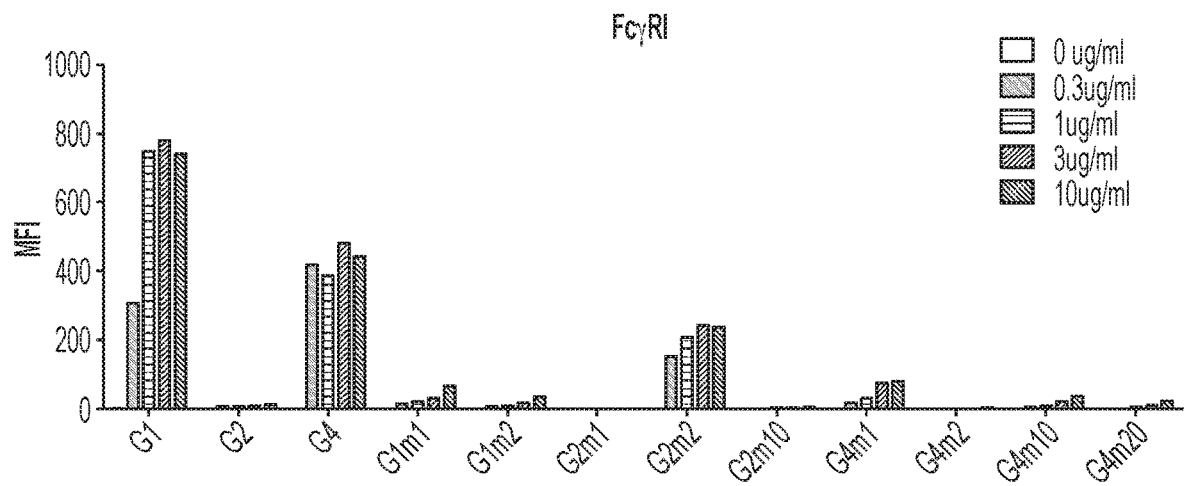
FIGS. 1A-1W are charts showing binding activity of various IgG variants as indicated to different types of Fcγ receptors expressed on CHO-K1 cells at the various concentrations as indicated. The concentrations of each IgG variant, from left to right, are 0 μg/ml, 0.3 μg/ml, 1 μg/ml, 3 μg/ml, and 10 μg/ml in FIGS. 1A-1C, 1E-J, 1L-1N, 1P-1R, and 1T-1V. For FIGS. 1D, 1K, 1O, 1S, and 1W the bars, from left to right, correspond to the following concentrations of IgG variant: 0.3 μg/ml, 1 μg/ml, 3 μg/ml, and 10 μg/ml.
Figure 1B:
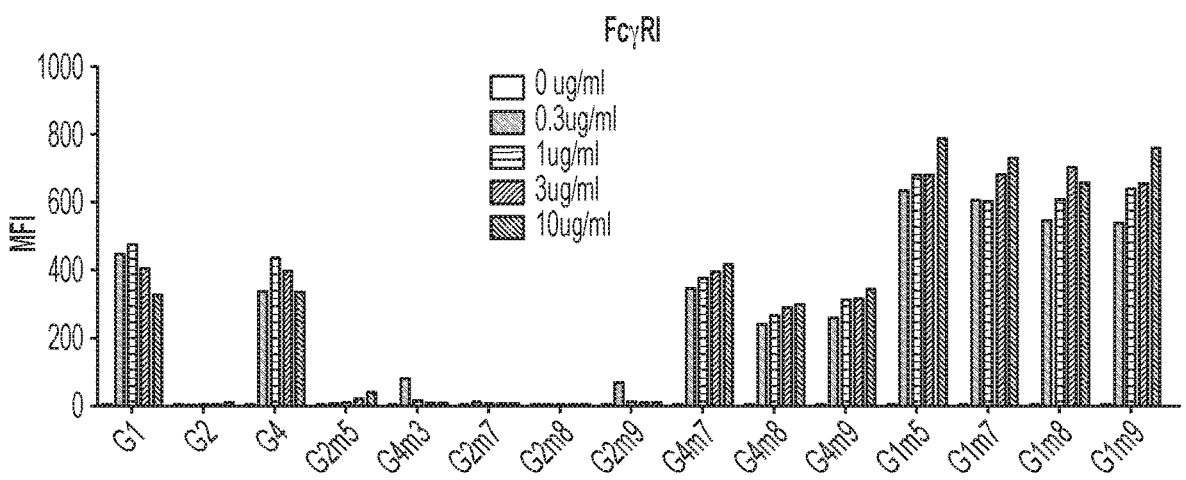
Figure 1C:
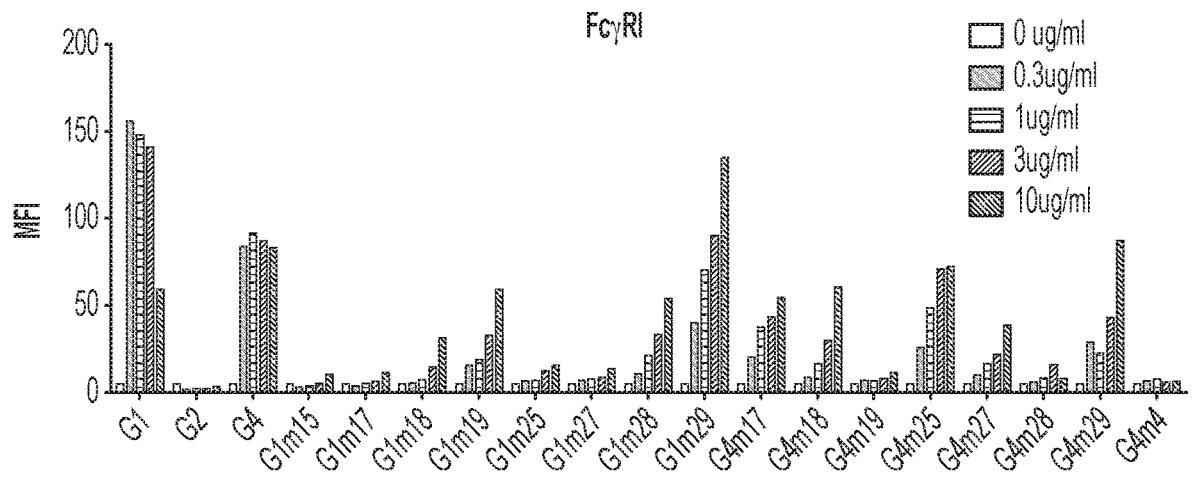
Figure 1D:
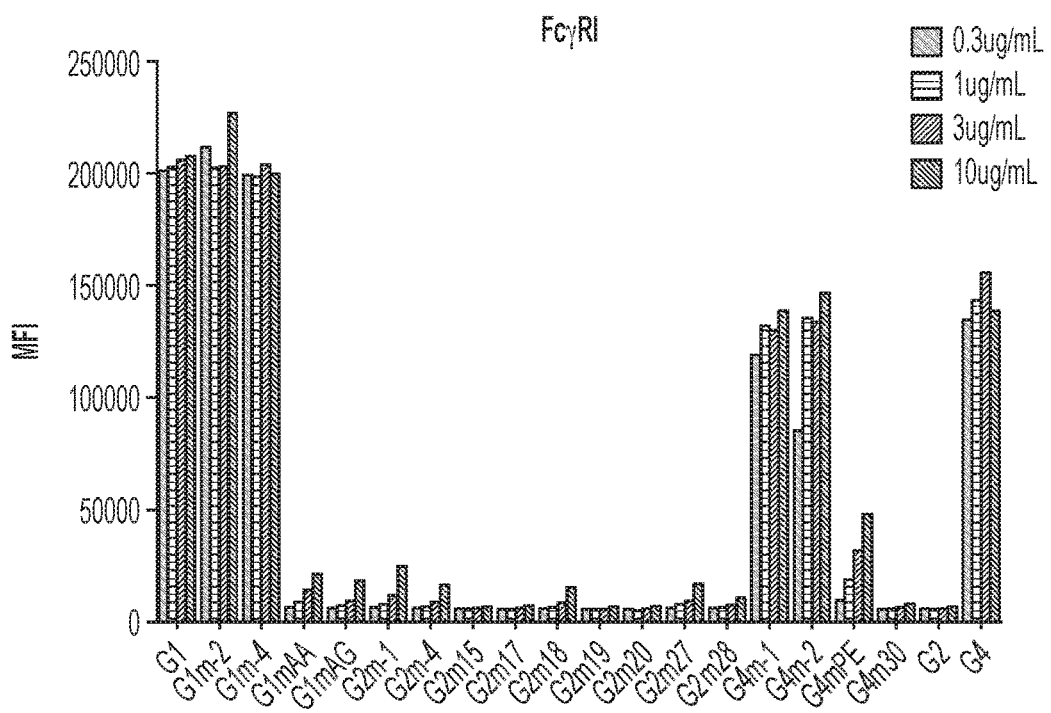
Figure 1E:
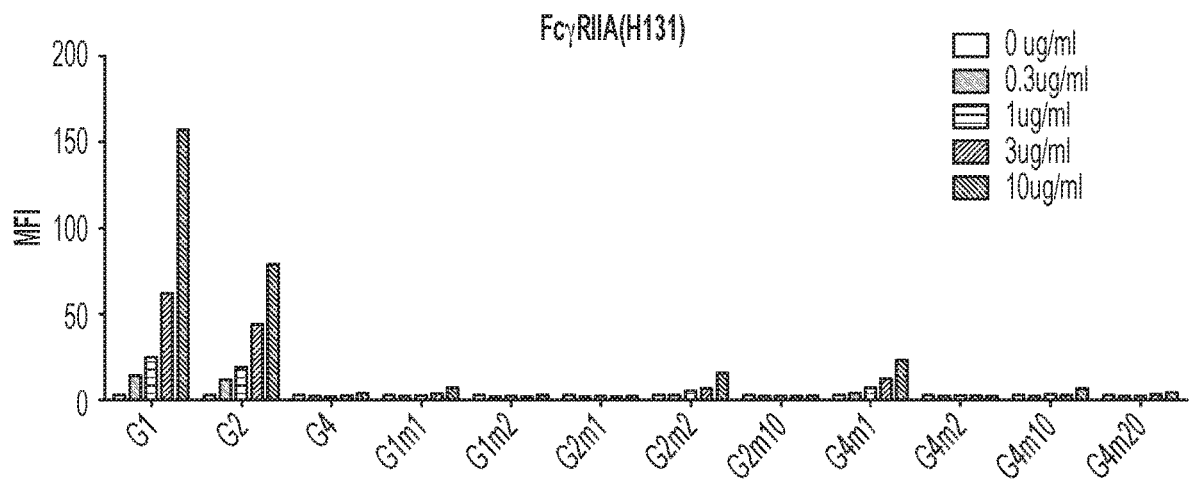
Figure 1F:
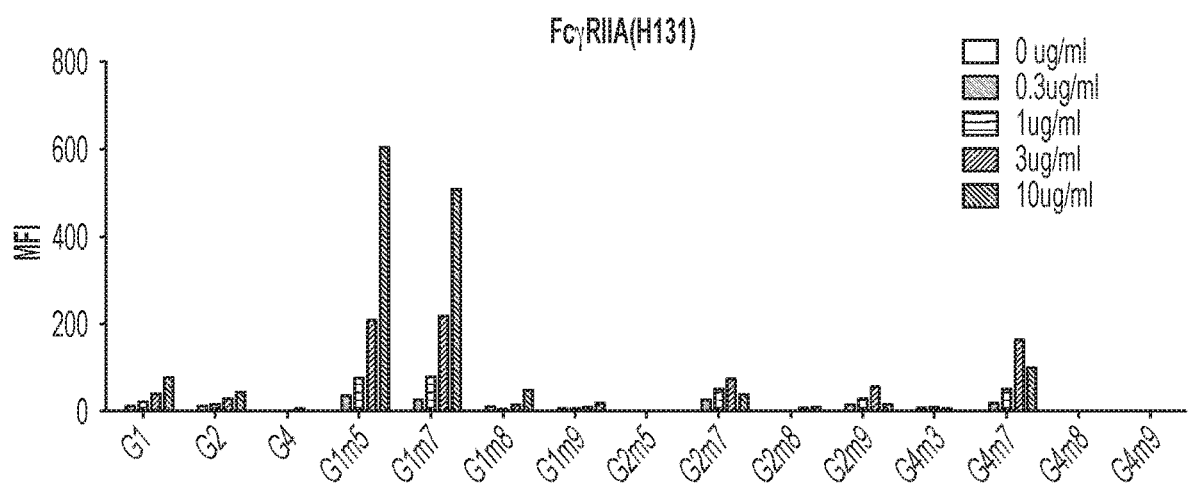
Figure 1G:
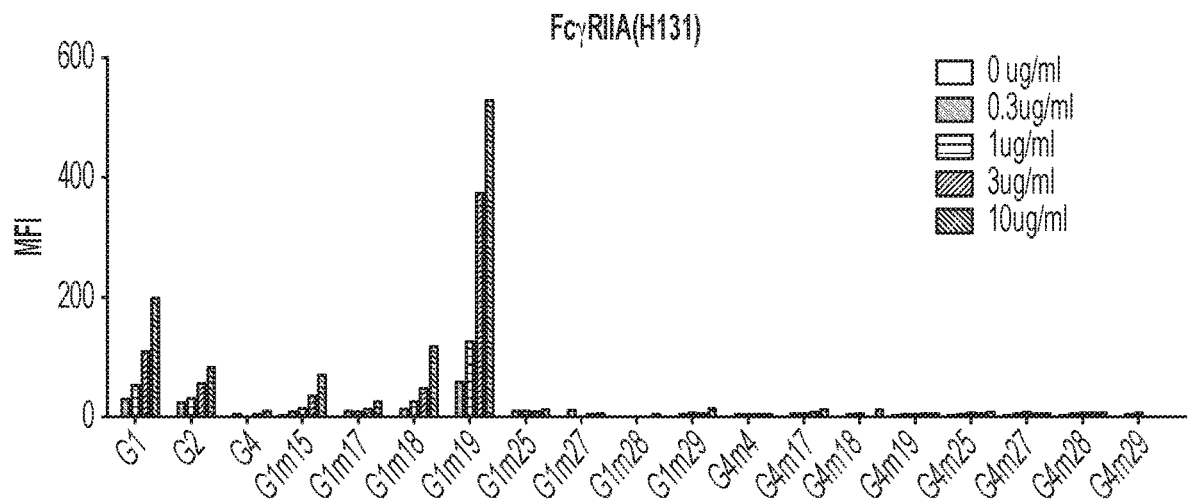
Figure 1H:
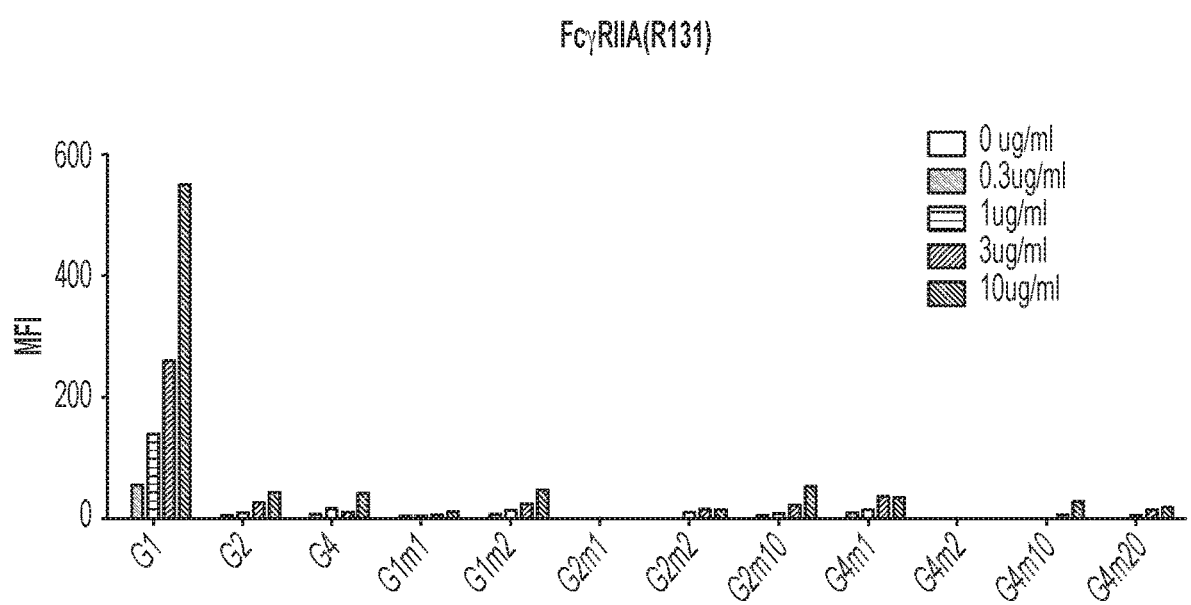
Figure 1I:
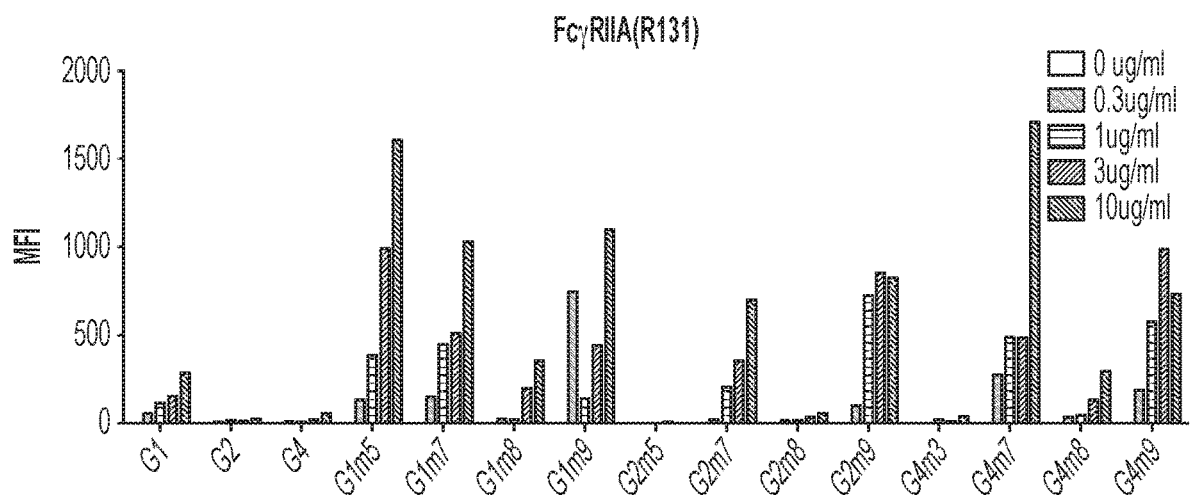
Figure 1J:
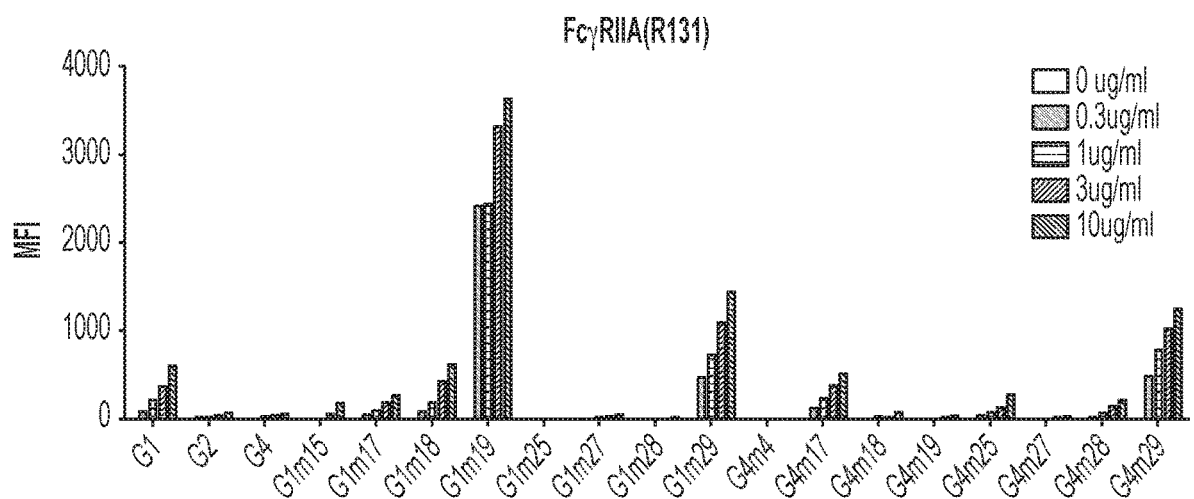
Figure 1K:
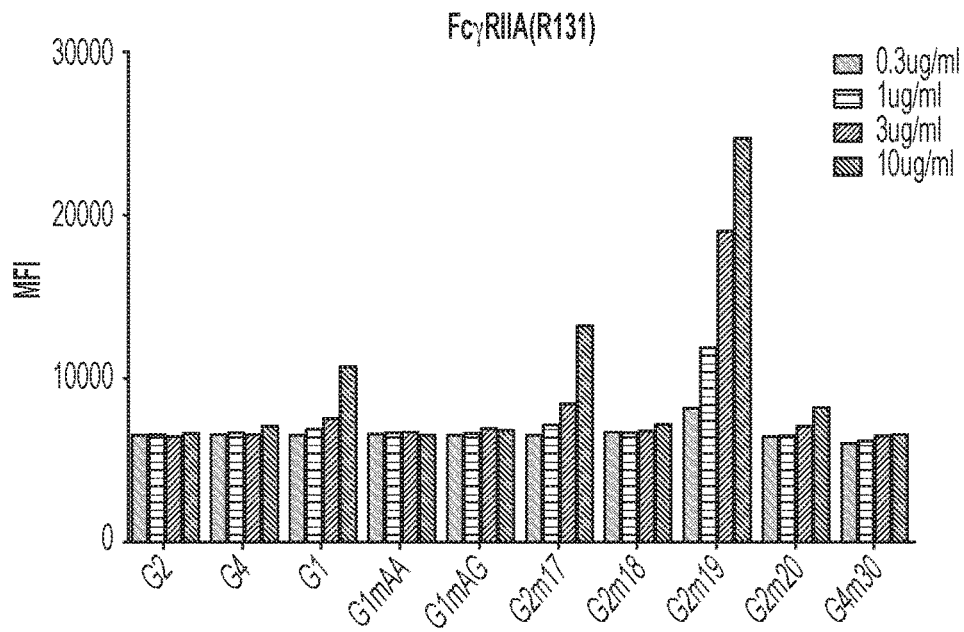
Figure 1L:
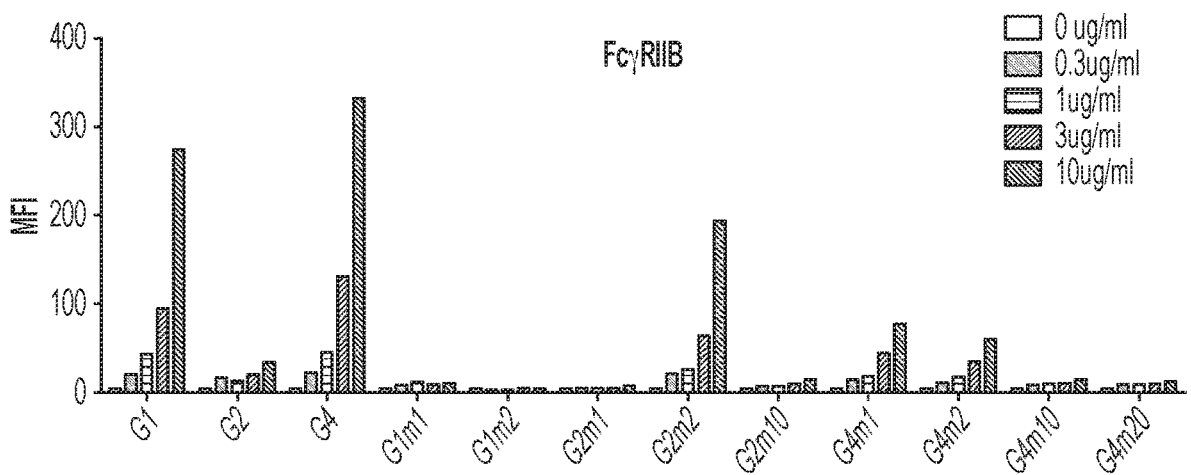
Figure 1M:
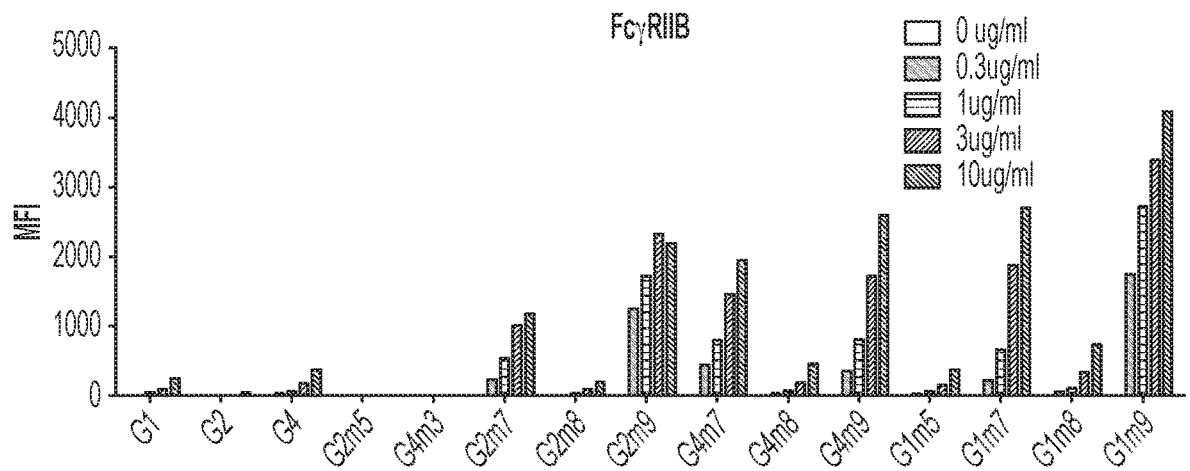
Figure 1N:
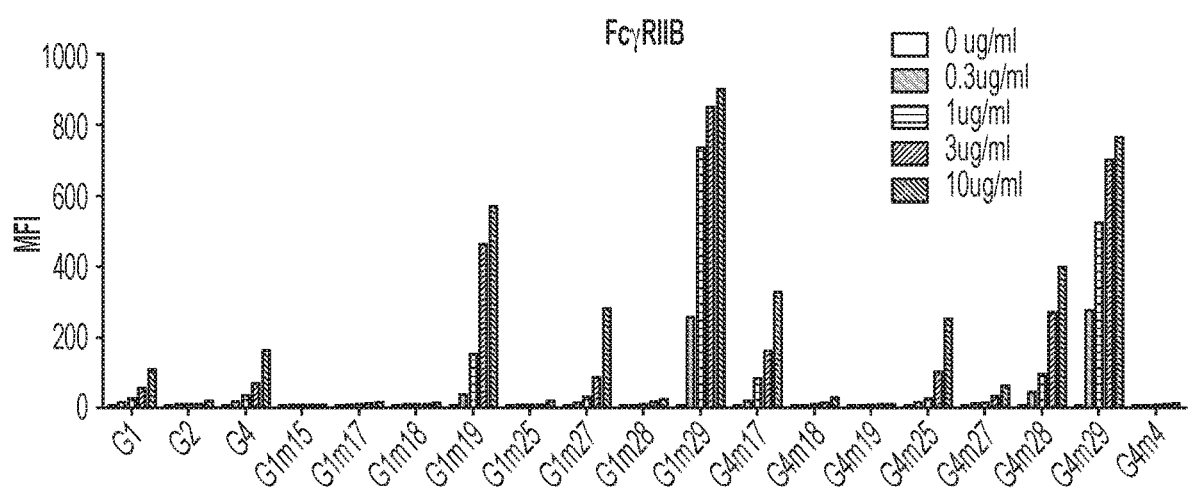
Figure 1O:
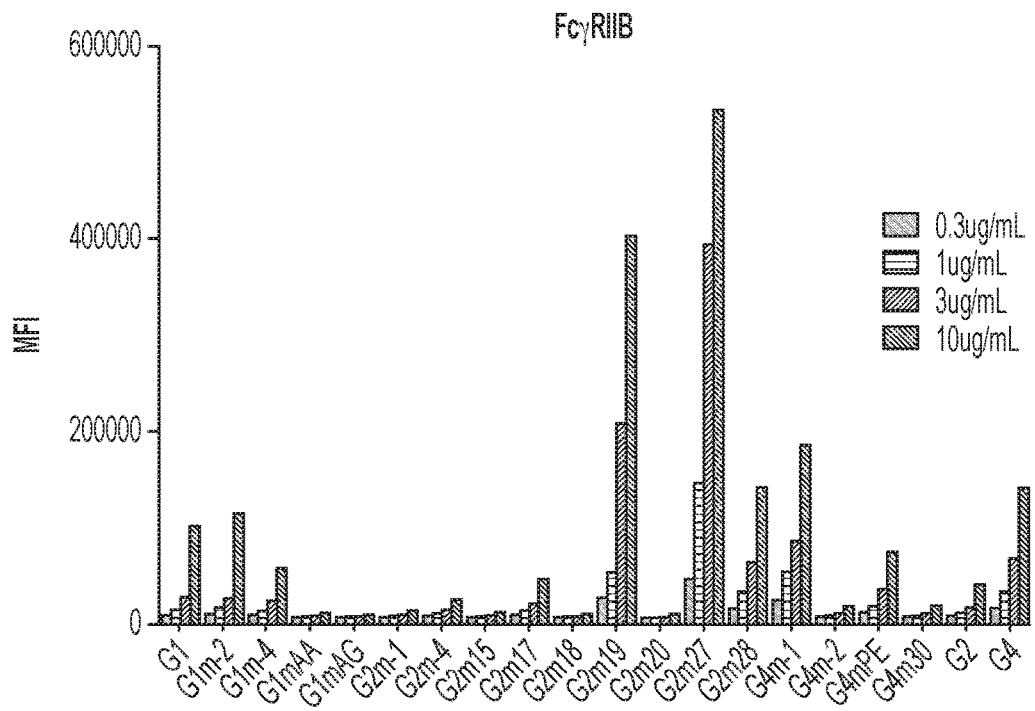
Figure 1P:
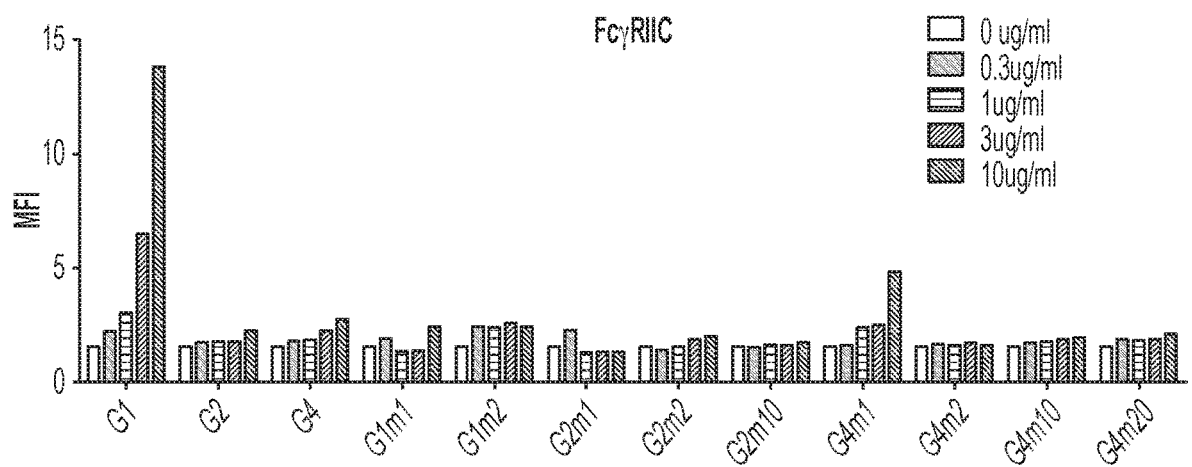
Figure 1Q:
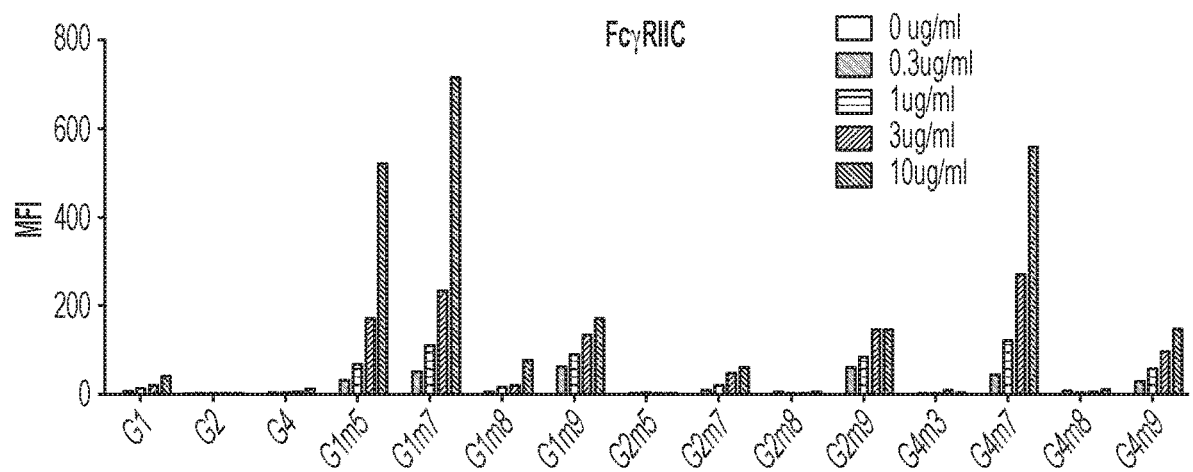
Figure 1R:
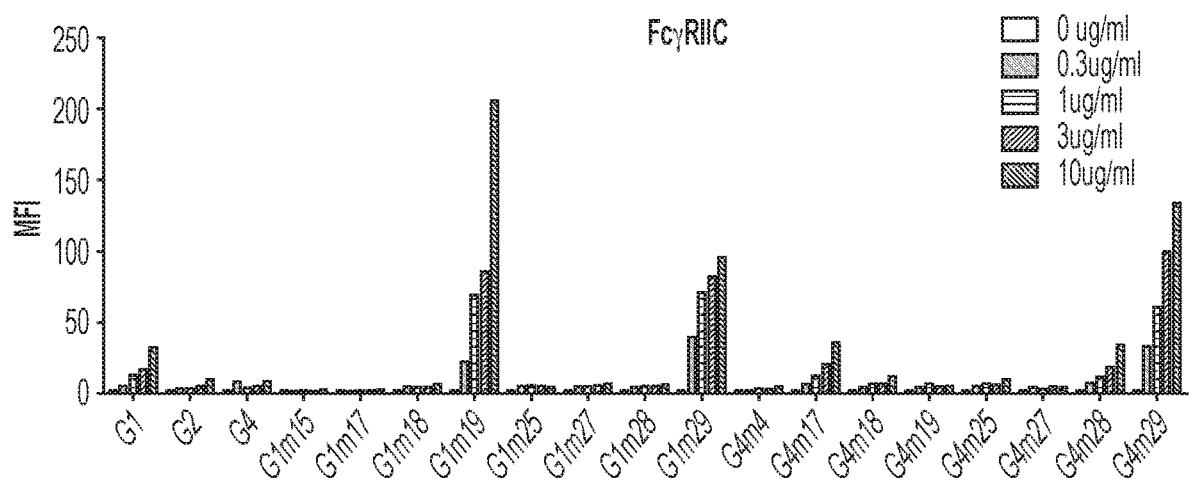
Figure 1S:
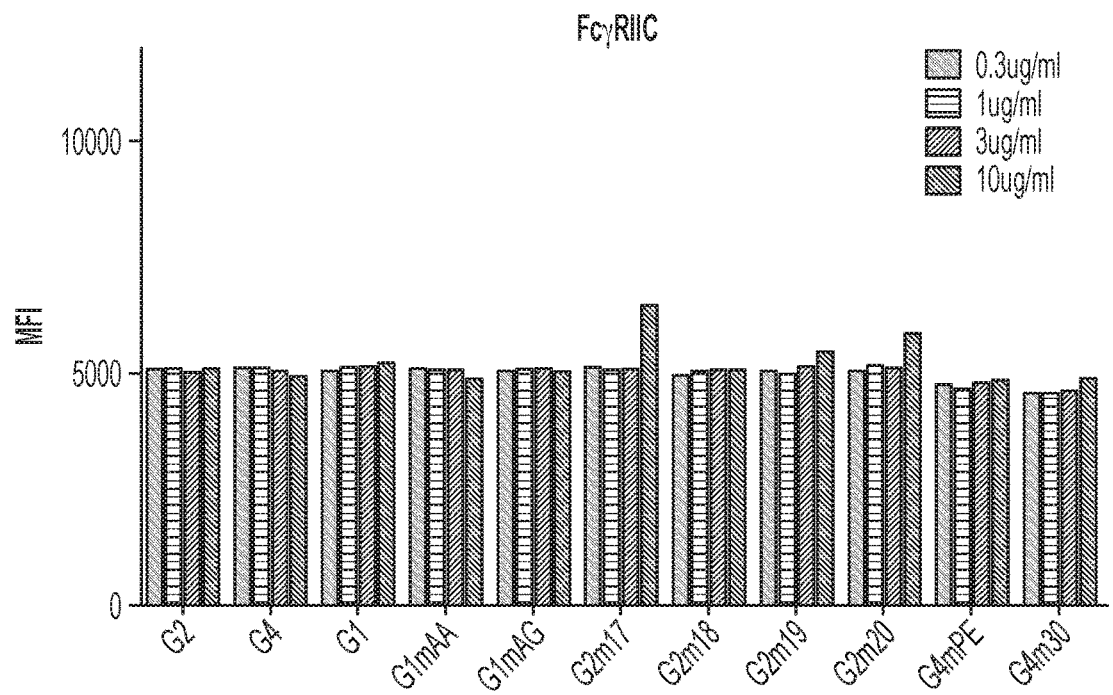
Figure 1T:
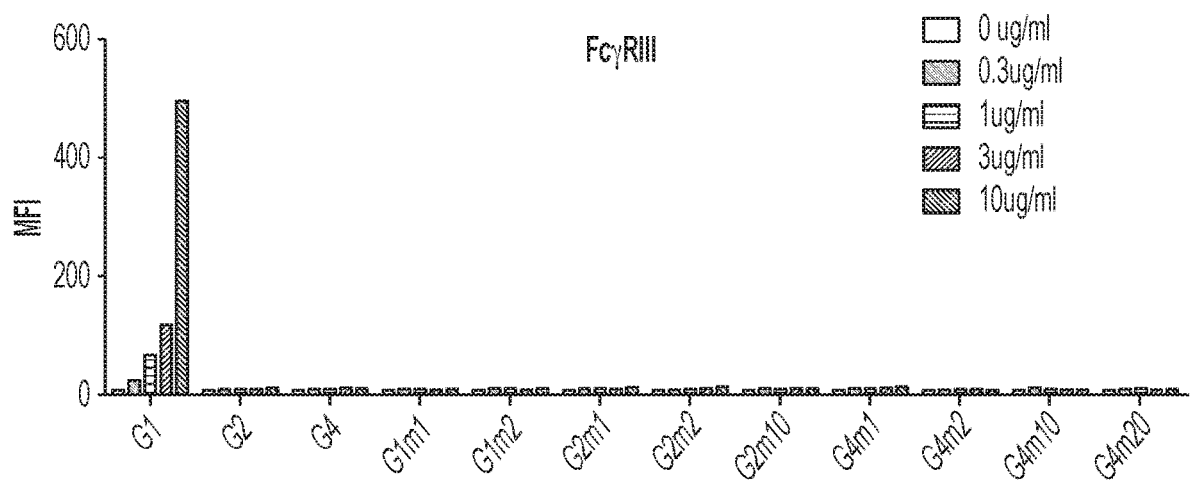
Figure 1U:
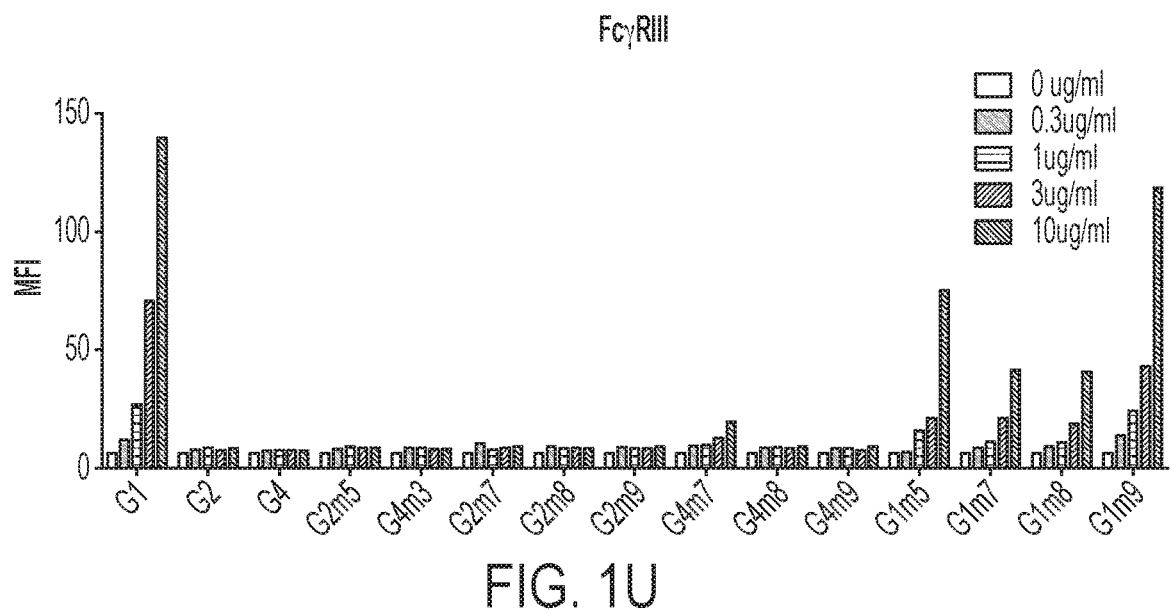
Figure 1V:
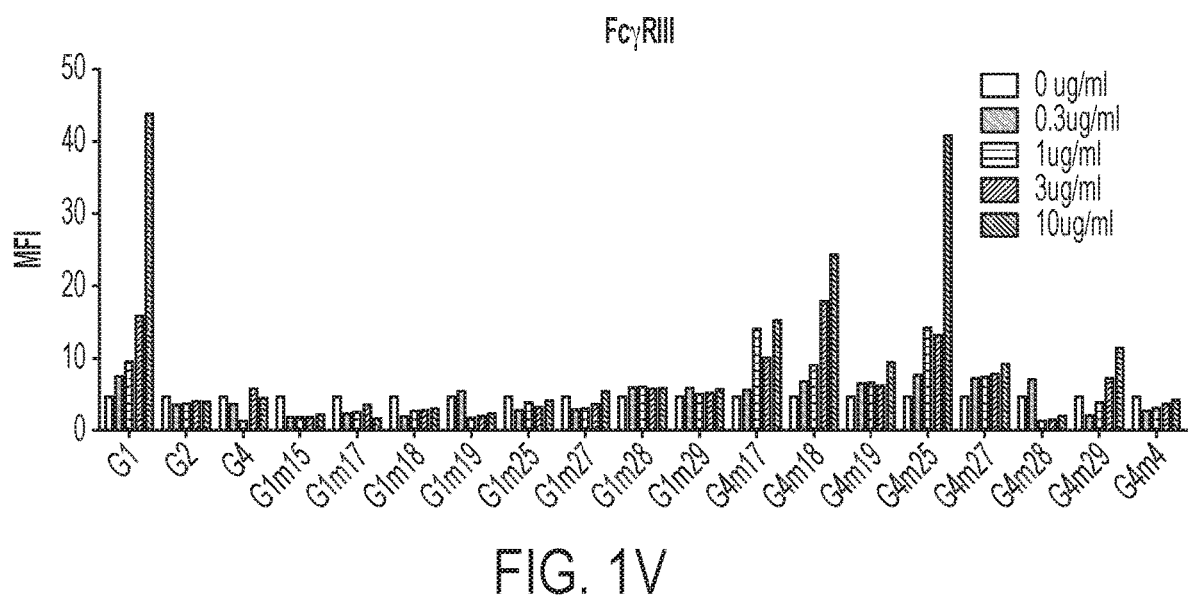

Agonistic anti-TNFR antibodies that are capable of binding to FcγRIIB (CD32B) showed enhanced activity in mouse models and mouse IgG1 isoform showed the best anti-tumor efficacy. These results indicate that agonistic antibodies having selective binding activity to the FcγRIIB (CD32B) would be expected to have better agonistic activity in stimulating immune responses. Further, it was observed that certain anti-tumor agonist antibodies showed differential liver toxicity, suggesting a novel approach for designing therapeutic agonist antibodies with enhanced therapeutic index (e.g., high treatment efficacy and low toxicity).

Accordingly, described herein are approaches for designing IgG molecules (e.g., IgG1, IgG2, and IgG4 molecules such as human IgG1, human IgG2, and human IgG4 molecules) containing an Fc variant having selective binding activity to FcγRIIB (CD32B) as relative to other Fc receptors such as FcγRIII (CD16), and cancer treatment methods, which involve the use of therapeutic agents capable of cross-linking an immune cell receptor such as a receptor of the tumor necrosis factor receptor superfamily (TNFSF) and FcγRIIB

I. Fc Variants

Described herein are Fc variants having enhanced selectivity to FcγRIIB relative to its wild-type counterpart. An Fc fragment having selectivity to FcγRIIB, selectively binding to FcγRIIB, or specifically binding to FcγRIIB is a term well understood in the art. A molecule is said to exhibit "selective binding" or "specific binding" if it reacts more frequently, more rapidly, with greater duration and/or with greater affinity with a particular target antigen (e.g., an FcγRIIB receptor) than it does with alternative targets (e.g., FcγRIII receptors). An Fc fragment "specifically binds" to an Fc receptor if it binds with greater affinity, avidity, more readily, and/or with greater duration than it binds to other Fc receptors. For example, an Fc fragment that specifically (or preferentially) binds to FcγRIIB is an Fc fragment that binds this Fc receptor with greater affinity, avidity, more readily, and/or with greater duration than it binds to other Fc receptors. It is also understood with this definition that, for example, an Fc fragment that selectively or specifically binds to a first Fc receptor may or may not specifically or preferentially bind to a second Fc receptor. As such, "selective binding," "specific binding" or "preferential binding" does not necessarily require (although it can include) exclusive binding. In some examples, an Fc fragment that "selectively binds," or "specifically binds" to a target Fc receptor (e.g., FcγRIIB) may not bind to other Fc receptors (i.e., binding not detectable by routine methods). Relative binding affinities of IgG1, IgG2, and IgG4 to different Fc receptors are given in Table 1 below.

TABLE 1

Relative Binding Affinities of Human and Mouse Immunoglobulins to Fc Receptors

| | Human | | | | Mouse | | |
| --- | --- | --- | --- | --- | --- | --- | --- |
| FcγR | IgG1 | IgG2 | IgG4 | FcγR | IgG1 | IgG2a | IgG2b |
| I | + + + + | − | + + + + | I | − | + + + + | + + + + |
| IIa (H131) | + + + | + + | + + | III | + + | + + | + + |
| IIa (R131) | + + + | + | + + | | | | |
| IIb | + + | +/− | + + | IIb | + + + | + + | + + + |
| IIIa (V158) | + + + | + | + + | IV | − | + + + | + + |
| IIIa (F158) | + + | +/− | + + | | | | |

The Fc variants described herein may have enhanced selectivity to FcγRIIB relative to their wild-type counterparts (the wild-type parent Fc region in which mutations are introduced to produce the Fc variants). The relative binding activity to FcγRIIB versus another Fc receptor (e.g., FcγRIII) of such an Fc variant is higher than the relative binding activity to FcγRIIB versus the other Fc receptor (e.g., FcγRIII) of the wild-type counterpart. The Fc variant may have enhanced binding activity to FcγRIIB and/or decreased binding activity to another Fc receptor, for example, FcγRIII In some embodiments, the Fc variants described herein may have decreased binding activity to both FcγRIIB and another Fc receptor (for example, FcγRIII); however, the level of decreased binding activity to the other Fc receptor (e.g., FcγRIII) is greater than the level of decreased binding activity to FcγRIIB In some embodiments, an Fc variant as described herein has a suitable binding affinity for FcγRIIB, e.g., enhanced as compared with the wild-type parent Fc from which the Fc variant is derived. As used herein, "binding affinity" refers to the apparent association constant or $K_A$. The $K_A$ is the reciprocal of the dissociation constant ($K_D$). The Fc variant described herein may have a binding affinity (K D) of at least $10^{-5}$, $10^{-6}$, $10^{-7}$, $10^{-8}$, $10^{-9}$, $10^{-10}$ M, or lower for FcγRIIB. An increased binding affinity corresponds to a decreased $K_D$. Higher affinity binding of an Fc fragment for a first Fc receptor relative to a second Fc receptor can be indicated by a higher $K_A$ (or a smaller numerical value $K_D$) for binding the first Fc receptor than the $K_A$ (or numerical value $K_D$) for binding the second Fc receptor. In such cases, the Fc variant has specificity for the first Fc receptor relative to the second Fc receptor. In some embodiments, the Fc variants described herein have a higher binding affinity (a higher $K_A$ or smaller $K_D$) to FcγRIIB as compared to the binding affinity to FcγRIII (either FcγRIIIA or FcγRIIIB) Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity (or binding specificity) can be determined by a variety of methods including equilibrium dialysis, equilibrium binding, gel filtration, ELISA, surface plasmon resonance, or spectroscopy (e.g., using a fluorescence assay). See also Examples below. Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

[Bound]=[Free]/(Kd+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay (an in vitro or in vivo assay).

In some embodiments, the Fc variants described herein may be designed by mutating one or more amino acid residues in the wild-type of human IgG1, IgG2, or IgG4 Fc fragments in light of the amino acid residues in the corresponding mouse IgG, for example, mouse IgG1. A sequence comparison of human and mouse IgGs is provided below (SEQ ID Nos: 67-69, 64, and 65, from top to bottom, each representing a combination of fragments 211-245, 260-278, and 320-332 of the corresponding Fc region):

portion, in the lower portion, or both of the hinge domain. For example, the Fc variant may comprise one or more amino acid substitutions at one or more of positions 233, 234, 235, and/or 236. Such an amino acid substitution may be in combination with the deletion of one or more of the GGP motif (236-238) noted herein. These mutations may be introduced into a human IgG2 or IgG4 Fc fragment to produce the Fc variants described herein. In some examples, the Fc variants described herein contains a deletion at one or more of the positions 236-238 (e.g., 236, 237, 238 or any combination thereof)

Any of the mutations in the hinge domain described herein may be in combination with a mutation (e.g., amino acid substitutions) at one or more positions that are involved in interaction with an Fc receptor. Such positions include, but are not limited to, positions 267, 273, 328, and/or 329. Exemplary amino acid substitutions at those positions include S261E, V271E, L328F, and P329G. Fc variants derived from IgG2 or IgG4 molecules that contain one or more mutations at positions 267, 273, 328, and/or 329 are also within the scope of the present disclosure. Such mutations may include amino acid substitutions at one or more of these positions, for example, S261E, V271E, L328F, and/or P329G.

In some embodiments, an Fc variant described herein may comprise an amino acid sequence at least 85% identical (e.g., 90%, 95%, 98%, 99%, or above) to that of its wild-type counterpart (e.g., the Fc fragment of wild-type human IgG1,

```
            21-        22-        23-        24-    ...26-         27-         ...32-         33-

12345678  9012345 6789 0123456789012345...0123456789012345678...0123456789012

Upper      Core Lower         CH2 hIgG1    VDKKVEPK-SCDKTHT CPPC PAPELLGGPSVFLFPP...TCVVVDVSHEDPEVKFNWY...KCKVSNKALPAPI hIgG2    VDKTVERK-CC-V-E- CPPC PAPPVA-GPSVFLFPP...TCVVVDVSHEDPEVQFNWY...KCKVSNKGLPAPI hIgG4    VDKRVESKYG----PP CPSC PAPEELGGPSVFLFPP...TCVVVDVSQEDPEVQFNWY...KCKVSNKGLPSSI mIgG1    VDKKIVPR-DC--G CKPCIC TVPEVS---SVFIFPP...TCVVVDISKDDPEVQFSWF...KCRVNSAAFPAPI mIgG2a   VDKKIEPRGPTIKP CPPCKC PAPNLLGGPSVFIFPP...TCVVVDVSEDDPDVQISWF...KCKVNNKDLPAPI
```

In some embodiments, the Fc variants described herein is a human IgG1, G2, or G4 Fc variants comprising one or more mutations (e.g., amino acid substitutions, deletions, or additions) in the hinge domain of an Fc fragment. Human IgGs contain a core motif of CPPC or CPSC in the hinge domain (positions 226-229 according to the EU index). Positions 216 to 225 are deemed as the upper portion of the hinge domain and positions 230-238 are deemed as the lower portion of the hinge domain. The numbering system used herein, unless explicitly indicated, is according to the EU index. In some examples, the one or more mutations can be located in the upper portion of the hinge domain. Alternatively or in addition, the one or more mutations can be located in the lower portion of the hinge domain.

The mutations to a human IgG Fc can be made according to the corresponding amino acid residues in the hinge domain of mouse IgG1. For example, mouse IgG1 does not contain the GGP motif at positions 236-238. Accordingly, one or more of the residues in this GGP motif can be deleted from a human IgG1, IgG2, or IgG4 Fc fragment to produce the Fc variants described herein.

Alternatively or in addition, the human Fc variants may contain one or more amino acid substitutions in the upper IgG2, or IgG4 described herein). The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In one example, the amino acid residue substitutions in an Fc variant described herein are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Provided below is a sequence alignment showing exemplary positions where mutations can be introduced into hIgG1, hIgG2, and IgG4 to produce various Fc variants for the present disclosure.

```
Sequence alignment of human IgG1 variants relative to wild-type human IgG1
(SEQ ID NOs: 70-88, from top to bottom):
            21-        22-         23-         24-    ...26-        27-        ...32-         33-
            12345678 901234567890123456789012345...0123456789012345678...0123456789012
            Upper      CoreLower   CH2 hIgG1     VDKKVEPK-SCDKTHTCPPCPAPELLGGPSVFLFPP...TCVVVDVSHEDPEVKFNWY...KCKVSNKALPAPI hIgG1m1     KVEPK-SCDKTHTCPPCPAPELL---SVFLFPP...TCVVVDVSHEDPEVKFNWY...KCKVSNKALPAPI hIgG1m2     KVEPK-SCDKTHTCPPCPAPELL-GPSVFLFPP...TCVVVDVSHEDPEVKFNWY...KCKVSNKALPAPI hIgG1m-2   KKVEPK-CC-V-E-CPPCPAPELLGGPSVFLFPP...TCVVVDVSHEDPEVKFNWY...KCKVSNKALPAPI hIgG1m-4   KKVEPKYG---PPCPPCPAPELLGGPSVFLFPP...TCVVVDVSHEDPEVKFNWY...KCKVSNKALPAPI hIgG1m5     KVEPK-SCDKTHTCPPCPAPELL-GPSVFLFPP...TCVVVDVSHEDPEEKFNWY...KCKVSNKALPAPI hIgG1m7     KVEPK-SCDKTHTCPPCPAPELLGGPSVFLFPP...TCVVVDVEHEDPEVKFNWY...KCKVSNKALPAPI hIgG1m8     KVEPK-SCDKTHTCPPCPAPELLGGPSVFLFPP...TCVVVDVSHEDPEVKFNWY...KCKVSNKAPPAPI hIgG1m9     KVEPK-SCDKTHTCPPCPAPELLGGPSVFLFPP...TCVVVDVEHEDPEVKFNWY...KCKVSNKAPPAPI hIgG1m15    KVEPK-SCDKTHTCPPCPAPELL---SVFLFPP...TCVVVDVSHEDPEEKFNWY...KCKVSNKALPAPI hIgG1m17    KVEPK-SCDKTHTCPPCPAPELL---SVFLFPP...TCVVVDVEHEDPEVKFNWY...KCKVSNKALPAPI hIgG1m18    KVEPK-SCDKTHTCPPCPAPELL---SVFLFPP...TCVVVDVSHEDPEVKFNWY...KCKVSNKAPPAPI hIgG1m19    KVEPK-SCDKTHTCPPCPAPELL---SVFLFPP...TCVVVDVEHEDPEVKFNWY...KCKVSNKAPPAPI hIgG1m25    KVEPK-SCDKTHTCPPCPAPELL-GPSVFLFPP...TCVVVDVSHEDPEEKFNWY...KCKVSNKALPAPI hIgG1m27    KVEPK-SCDKTHTCPPCPAPELL-GPSVFLFPP...TCVVVDVEHEDPEVKFNWY...KCKVSNKALPAPI hIgG1m28    KVEPK-SCDKTHTCPPCPAPELL-GPSVFLFPP...TCVVVDVSHEDPEVKFNWY...KCKVSNKAPPAPI hIgG1m29    KVEPK-SCDKTHTCPPCPAPELL-GPSVFLFPP...TCVVVDVEHEDPEVKFNWY...KCKVSNKAPPAPI hIgG1mAA  KKVEPK-SCDKTHTCPPCPAPEAAGGPSVFLFPP...TCVVVDVSHEDPEVKFNWY...KCKVSNKALPAPI hIgG1mAG  KKVEPK-SCDKTHTCPPCPAPEAAGGPSVFLFPP...TCVVVDVSHEDPEVKFNWY...KCKVSNKALGAPI

Sequence alignment of human IgG2 variants relative to wild-type human IgG2
(SEQ ID NOs: 89-105, from top to bottom):
            21-        22-         23-         24-    ...26-        27-        ...32-         33-
            12345678 901234567890123456789012345...0123456789012345678...0123456789012
            Upper      CoreLower   CH2 hIgG2     VDKTVERK-CC-V-E-CPPCPAPPVA-GPSVFLFPP...TCVVVDVSHEDPEVQFNWY...KCKVSNKGLPAPI hIgG2m1    TVERK-CC-V-E-CPPCPAPPVA---SVFLFPP...TCVVVDVSHEDPEVQFNWY...KCKVSNKGLPAPI hIgG2m-1  KTVERK-SCDKTHTCPPCPAPPVA-GPSVFLFPP...TCVVVDVSHEDPEVQFNWY...KCKVSNKGLPAPI
```

-continued

```
hIgG2m2    TVERK-CC-V-E-CPPCPAPPFLGGPSVFLFPP...TCVVVDVSHEDPEVQFNWY...KCKVSNKGLPAPI hIgG2m-4   KTVERKYG---PPCPPCPAPPVA-GPSVFLFPP...TCVVVDVSHEDPEVQFNWY...KCKVSNKGLPAPI hIgG2m5    TVERK-CC-V-E-CPPCPAPPVA-GPSVFLFPP...TCVVVDVSHEDPEEQFNWY...KCKVSNKGLPAPI hIgG2m7    TVERK-CC-V-E-CPPCPAPPVA-GPSVFLFPP...TCVVVDVEHEDPEVQFNWY...KCKVSNKGLPAPI hIgG2m8    TVERK-CC-V-E-CPPCPAPPVA-GPSVFLFPP...TCVVVDVSHEDPEVQFNWY...KCKVSNKGFPAPI hIgG2m9    TVERK-CC-V-E-CPPCPAPPVA-GPSVFLFPP...TCVVVDVEHEDPEVQFNWY...KCKVSNKGFPAPI hIgG2m10   TVERK-CC-V-E-CPPCPAPEVS--SVFLFPP...TCVVVDVSHEDPEVQFNWY...KCKVSNKGFPAPI hIgG2m15   TVERK-CC-V-E-CPPCPAPPVA--SVFLFPP...TCVVVDVSHEDPEEQFNWY...KCKVSNKGLPAPI hIgG2m17   TVERK-CC-V-E-CPPCPAPPVA--SVFLFPP...TCVVVDVEHEDPEVQFNWY...KCKVSNKGLPAPI hIgG2m18   TVERK-CC-V-E-CPPCPAPPVA--SVFLFPP...TCVVVDVSHEDPEVQFNWY...KCKVSNKGFPAPI hIgG2m19   TVERK-CC-V-E-CPPCPAPPVA--SVFLFPP...TCVVVDVEHEDPEVQFNWY...KCKVSNKGFPAPI hIgG2m20   TVERK-CC-V-E-CPPCPAPPVA--PSVFLFPP...TCVVVDVSHEDPEVQFNWY...KCKVSNKGLPAPI hIgG2m27   TVERK-CC-V-E-CPPCPAPPVA--PSVFLFPP...TCVVVDVEHEDPEVQFNWY...KCKVSNKGLPAPI hIgG2m28   TVERK-CC-V-E-CPPCPAPPVA--PSVFLFPP...TCVVVDVSHEDPEVQFNWY...KCKVSNKGFPAPI
```

Sequence alignment of human IgG4 variants relative to wild-type human IgG4
(SEQ ID NOs: 106-117, 66, and 118-127, from top to bottom)

```
         21-       22-       23-       24-    ...26-      27-    ...32-       33-
         12345678  90123456789012345678901245...0123456789012345678...0123456789012
         Upper     Core Lower     CH2 hIgG4    VDKRVESKYG----PPCPSCPAPEFLGGPSVFLFPP...TCVVVDVSQEDPEVQFNWY...KCKVSNKGLPSSI hIgG4m1  KRVESKYG----PPCPPCPAPEFL--SVFLFPP...TCVVVDVSQEDPEVQFNWY...KCKVSNKGLPSSI hIgG4m-1 KRVESK-SCDKTHTCPPCPAPEFLGGPSVFLFPP...TCVVVDVSQEDPEVQFNWY...KCKVSNKGLPSSI hIgG4m2  KRVESKYG----PPCPPCPAPEFL-GPSVFLFPP...TCVVVDVSQEDPEVQFNWY...KCKVSNKGLPSSI hIgG4m-2 KRVESK-CC-V-E-CPPCPAPEFLGGPSVFLFPP...TCVVVDVSQEDPEVQFNWY...KCKVSNKGLPSSI hIgG4m3  KRVESKYG----PPCPPCPAPEFLGGPSVFLFPP...TCVVVDVSQEDPEEQFNWY...KCKVSNKGLPSSI hIgG4m4  KRVESKYG----PPCPPCPAPEFL---SVFLFPP...TCVVVDVSQEDPEEQFNWY...KCKVSNKGLPSSI hIgG4m5  KRVESKYG----PPCPPCPAPEFL-GPSVFLFPP...TCVVVDVSQEDPEEQFNWY...KCKVSNKGLPSSI hIgG4m7  KRVESKYG----PPCPPCPAPEFLGGPSVFLFPP...TCVVVDVEQEDPEVQFNWY...KCKVSNKGLPSSI hIgG4m8  KRVESKYG----PPCPPCPAPEFLGGPSVFLFPP...TCVVVDVSQEDPEVQFNWY...KCKVSNKGFPSSI hIgG4m9  KRVESKYG----PPCPPCPAPEFLGGPSVFLFPP...TCVVVDVEQEDPEVQFNWY...KCKVSNKGFPSSI hIgG4m10 KRVESKYG----PPCPPCPAPEVS--SVFLFPP...TCVVVDVSQEDPEVQFNWY...KCKVSNKGFPSSI hIgG4m15 KRVESKYG----PPCPPCPAPEFL--SVFLFPP...TCVVVDVSQEDPEEQFNWY...KCKVSNKGLPSSI hIgG4m17 KRVESKYG----PPCPPCPAPEFL--SVFLFPP...TCVVVDVEQEDPEVQFNWY...KCKVSNKGLPSSI
```

-continued

```
hIgG4m18  KRVESKYG----PPCPPCPAPEFL...SVFLFPP...TCVVVDVSQEDPEVQFNWY...KCKVSNKGFPSSI hIgG4m19  KRVESKYG----PPCPPCPAPEFL...SVFLFPP...TCVVVDVEQEDPEVQFNWY...KCKVSNKGFPSSI hIgG4m20  KRVESKYG----PPCPPCPAPEFLG..SVFLFPP...TCVVVDVSQEDPEVQFNWY...KCKVSNKGLPSSI hIgG4m25  KRVESKYG----PPCPPCPAPEFL.GPSVFLFPP...TCVVVDVSQEDPEEQFNWY...KCKVSNKGLPSSI hIgG4m27  KRVESKYG----PPCPPCPAPEFL.GPSVFLFPP...TCVVVDVEQEDPEVQFNWY...KCKVSNKGLPSSI hIgG4m28  KRVESKYG----PPCPPCPAPEFL.GPSVFLFPP...TCVVVDVSQEDPEVQFNWY...KCKVSNKGFPSSI hIgG4m29  KRVESKYG----PPCPPCPAPEFL.GPSVFLFPP...TCVVVDVEQEDPEVQFNWY...KCKVSNKGFPSSI hIgG4m30  KRVESKYG----PPCPPCPAPEFL..PSVFLFPP...TCVVVDVSQEDPEVQFNWY...KCKVSNKGLPSSI hIgG4mPE  KRVESKYG----PPCPPCPAPEFEGGPSVFLFPP...TCVVVDVSQEDPEVQFNWY...KCKVSNKGLPSSI
```

The amino acid sequences of wild-type human IgG1, IgG2, and IgG4 Fc fragments, and a number of exemplary hIgG1, hIgG2, and hIgG4 Fc variants are provided below:

Amino acid sequence of wild-type human IgG1 Fc fragment:

(SEQ ID NO: 1)
VDKKVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMTK

NQVSLTCLVKGFYPSDIAVEWESNGQPENNYKTTPPVLDSDGSFFLYSKL

TVDKSRWQQGNVFSCSVMHEALHNHYTQKSLSLSPGK

Amino acid sequence of wild-type human IgG2 Fc fragment:

(SEQ ID NO: 2)
VDKTVERKCCVECPPCPAPPVAGPSVFLFPPKPKDTLMISRTPEVTCVVV

DVSHEDPEVQFNWYVDGVEVHNAKTKPREEQFNSTFRVVSVLTVVHQDWL

NGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDK

SRWQQGNVFSCSVMHEALHNHYTQKSLSLSPGK

Amino acid sequence of wild-type human IgG4 Fc fragment:

(SEQ ID NO: 3)
VDKRVESKYGPPCPSCPAPEFLGGPSVFLFPPKPKDTLMISRTPEVTCVV

VDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVD

KSRWQEGNVFSCSVMHEALHNHYTQKSLSLSLGK

Amino acid sequence of human IgG4 S228P Fc variant:

(SEQ ID NO: 4)
VDKRVESKYGPPCPPCPAPEFLGGPSVFLFPPKPKDTLMISRTPEVTCVV

VDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVD

KSRWQEGNVFSCSVMHEALHNHYTQKSLSLSLGK

Amino acid sequences of exemplary human IgG1 Fc variants:
G1m1:

(SEQ ID NO: 5)
VDKKVEPKSCDKTHTCPPCPAPELLSVFLFPPKPKDTLMISRTPEVTCVV

VDVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQV

SLTCLVKGFYPSDIAVEWESNGQPENNYKTTPPVLDSDGSFFLYSKLTVD

KSRWQQGNVFSCSVMHEALHNHYTQKSLSLSPGK

G1m2:

(SEQ ID NO: 6)
VDKKVEPKSCDKTHTCPPCPAPELLGPSVFLFPPKPKDTLMISRTPEVTC

VVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLT

VDKSRWQQGNVFSCSVMHEALHNHYTQKSLSLSPGK

G1m-2:

(SEQ ID NO: 7)
VDKKVEPKCCVECPPCPAPELLSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSR

WQQGNVFSCSVMHEALHNHYTQKSLSLSPGK

G1m-4:
(SEQ ID NO: 8)
VDKKVEPKYGPPCPPCPAPELLGPSVFLFPPKPKDTLMISRTPEVTCVVV
DVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDK
SRWQQGNVFSCSVMHEALHNHYTQKSLSLSPGK

G1m5:
(SEQ ID NO: 9)
VDKKVEPKSCDKTHTCPPCPAPELLGGPSVFLFPPKPKDTLMISRTPEVT
CVVVDVSHEDPEEKFNWYVDGVEVHNAKTKPREEQYNSTYRVVSVLTVLH
QDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKL
TVDKSRWQQGNVFSCSVMHEALHNHYTQKSLSLSPGK

G1m7:
(SEQ ID NO: 10)
VDKKVEPKSCDKTHTCPPCPAPELLGGPSVFLFPPKPKDTLMISRTPEVT
CVVVDVEHEDPEVKFNWYVDGVEVHNAKTKPREEQYNSTYRVVSVLTVLH
QDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKL
TVDKSRWQQGNVFSCSVMHEALHNHYTQKSLSLSPGK

G1m8:
(SEQ ID NO: 11)
VDKKVEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLH
QDWLNGKEYKCKVSNKAFPAPIEKTISKAKGQPREPQVYTLPPSREEMTK
NQVSLTCLVKGFYPSDIAVEWESNGQPENNYKTTPPVLDSDGSFFLYSKL
TVDKSRWQQGNVFSCSVMHEALHNHYTQKSLSLSPGK

G1m9:
(SEQ ID NO: 12)
VDKKVEPKSCDKTHTCPPCPAPELLGGPSVFLFPPKPKDTLMISRTPEVT
CVVVDVEHEDPEVKFNWYVDGVEVHNAKTKPREEQYNSTYRVVSVLTVLH
QDWLNGKEYKCKVSNKAFPAPIEKTISKAKGQPREPQVYTLPPSREEMTK
NQVSLTCLVKGFYPSDIAVEWESNGQPENNYKTTPPVLDSDGSFFLYSKL
TVDKSRWQQGNVFSCSVMHEALHNHYTQKSLSLSPGK

G1m15:
(SEQ ID NO: 13)
VDKKVEPKSCDKTHTCPPCPAPELLSVFLFPPKPKDTLMISRTPEVTCVV
VDVSHEDPEEKFNWYVDGVEVHNAKTKPREEQYNSTYRVVSVLTVLHQDW
LNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVD
KSRWQQGNVFSCSVMHEALHNHYTQKSLSLSPGK

G1m17:
(SEQ ID NO: 14)
VDKKVEPKSCDKTHTCPPCPAPELLSVFLFPPKPKDTLMISRTPEVTCVV
VDVEHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVD
KSRWQQGNVFSCSVMHEALHNHYTQKSLSLSPGK

G1m18:
(SEQ ID NO: 15)
VDKKVEPKSCDKTHTCPPCPAPELLSVFLFPPKPKDTLMISRTPEVTCVV
VDVSHEDPEVKFNWYVDGVEVHNAKTKPREEQYNSTYRVVSVLTVLHQDW
LNGKEYKCKVSNKAFPAPIEKTISKAKGQPREPQVYTLPPSREEMTKNQV
SLTCLVKGFYPSDIAVEWESNGQPENNYKTTPPVLDSDGSFFLYSKLTVD
KSRWQQGNVFSCSVMHEALHNHYTQKSLSLSPGK

G1m19:
(SEQ ID NO: 16)
VDKKVEPKSCDKTHTCPPCPAPELLSVFLFPPKPKDTLMISRTPEVTCVV
VDVEHEDPEVKFNWYVDGVEVHNAKTKPREEQYNSTYRVVSVLTVLHQDW
LNGKEYKCKVSNKAFPAPIEKTISKAKGQPREPQVYTLPPSREEMTKNQV
SLTCLVKGFYPSDIAVEWESNGQPENNYKTTPPVLDSDGSFFLYSKLTVD
KSRWQQGNVFSCSVMHEALHNHYTQKSLSLSPGK

G1m25:
(SEQ ID NO: 17)
VDKKVEPKSCDKTHTCPPCPAPELLGPSVFLFPPKPKDTLMISRTPEVTC
VVVDVSHEDPEEKFNWYVDGVEVHNAKTKPREEQYNSTYRVVSVLTVLHQ
DWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLT
VDKSRWQQGNVFSCSVMHEALHNHYTQKSLSLSPGK

G1m27:
(SEQ ID NO: 18)
VDKKVEPKSCDKTHTCPPCPAPELLGPSVFLFPPKPKDTLMISRTPEVTC
VVVDVEHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLT
VDKSRWQQGNVFSCSVMHEALHNHYTQKSLSLSPGK

G1m28:
(SEQ ID NO: 19)
VDKKVEPKSCDKTHTCPPCPAPELLGPSVFLFPPKPKDTLMISRTPEVTC
VVVDVSHEDPEVKFNWYVDGVEVHNAKTKPREEQYNSTYRVVSVLTVLHQ
DWLNGKEYKCKVSNKAFPAPIEKTISKAKGQPREPQVYTLPPSREEMTKN
QVSLTCLVKGFYPSDIAVEWESNGQPENNYKTTPPVLDSDGSFFLYSKLT
VDKSRWQQGNVFSCSVMHEALHNHYTQKSLSLSPGK

G1m29:
(SEQ ID NO: 20)
VDKKVEPKSCDKTHTCPPCPAPELLGPSVFLFPPKPKDTLMISRTPEVTC
VVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLT
VDKSRWQQGNVFSCSVMHEALHNHYTQKSLSLSPGK

G1mAA:
(SEQ ID NO: 21)
VDKKVEPKSCDKTHTCPPCPAPEAAGGPSVFLFPPKPKDTLMISRTPEVT
CVVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMTK

NQVSLTCLVKGFYPSDIAVEWESNGQPENNYKTTPPVLDSDGSFFLYSKL

TVDKSRWQQGNVFSCSVMHEALHNHYTQKSLSLSPGK

G1mAG:

(SEQ ID NO: 22)
VDKKVEPKSCDKTHTCPPCPAPEAAGGPSVFLFPPKPKDTLMISRTPEVT

CVVVDVSHEDPEVKFNWYVDGVEVHNAKTKPREEQYNSTYRVVSVLTVLH

QDWLNGKEYKCKVSNKALGAPIEKTISKAKGQPREPQVYTLPPSREEMTK

NQVSLTCLVKGFYPSDIAVEWESNGQPENNYKTTPPVLDSDGSFFLYSKL

TVDKSRWQQGNVFSCSVMHEALHNHYTQKSLSLSPGK

Amino acid sequences of exemplary human IgG2 Fc
variants:
G2m1:

(SEQ ID NO: 23)
VDKTVERKCCVECPPCPAPPVASVFLFPPKPKDTLMISRTPEVTCVVVDV

SHEDPEVQFNWYVDGVEVHNAKTKPREEQFNSTFRVVSVLTVVHQDWLNG

KEYKCKVSNKGLPAPIEKTISKTKGQPREPQVYTLPPSREEMTKNQVSLT

CLVKGFYPSDIAVEWESNGQPENNYKTTPPMLDSDGSFFLYSKLTVDKSR

WQQGNVFSCSVMHEALHNHYTQKSLSLSPGK

G2m-1:

(SEQ ID NO: 24)
VDKTVERKSCDKTHTCPPCPAPPVAGPSVFLFPPKPKDTLMISRTPEVTC

VVVDVSHEDPEVQFNWYVDGVEVHNAKTKPREEQFNSTFRVVSVLTVVHQ

DWLNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSKLT

VDKSRWQQGNVFSCSVMHEALHNHYTQKSLSLSPGK

G2m2:

(SEQ ID NO: 25)
VDKTVERKCCVECPPCPAPPFLGGPSVFLFPPKPKDTLMISRTPEVTCVV

VDVSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKNQV

SLTCLVKGFYPSDIAVEWESNGQPENNYKTTPPMLDSDGSFFLYSKLTVD

KSRWQQGNVFSCSVMHEALHNHYTQKSLSLSPGK

G2m-4:

(SEQ ID NO: 26)
VDKTVERKYGPPCPPCPAPPVAGPSVFLFPPKPKDTLMISRTPEVTCVVV

DVSHEDPEVQFNWYVDGVEVHNAKTKPREEQFNSTFRVVSVLTVVHQDWL

NGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDK

SRWQQGNVFSCSVMHEALHNHYTQKSLSLSPGK

G2m5:

(SEQ ID NO: 27)
VDKTVERKCCVECPPCPAPPVAGPSVFLFPPKPKDTLMISRTPEVTCVVV

DVSHEDPEEQFNWYVDGVEVHNAKTKPREEQFNSTFRVVSVLTVVHQDWL

NGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDK

SRWQQGNVFSCSVMHEALHNHYTQKSLSLSPGK

G2m7:

(SEQ ID NO: 28)
VDKTVERKCCVECPPCPAPPVAGPSVFLFPPKPKDTLMISRTPEVTCVVV

DVEHEDPEVQFNWYVDGVEVHNAKTKPREEQFNSTFRVVSVLTVVHQDWL

NGKEYKCKVSNKGLPAPIEKTISKTKGQPREPQVYTLPPSREEMTKNQVS

LTCLVKGFYPSDIAVEWESNGQPENNYKTTPPMLDSDGSFFLYSKLTVDK

SRWQQGNVFSCSVMHEALHNHYTQKSLSLSPGK

G2m8:

(SEQ ID NO: 29)
VDKTVERKCCVECPPCPAPPVAGPSVFLFPPKPKDTLMISRTPEVTCVVV

DVSHEDPEVQFNWYVDGVEVHNAKTKPREEQFNSTFRVVSVLTVVHQDWL

NGKEYKCKVSNKG:TAPIEKTISKTKGQPREPQVYTLPPSREEMTKNQVS

LTCLVKGFYPSDIAVEWESNGQPENNYKTTPPMLDSDGSFFLYSKLTVDK

SRWQQGNVFSCSVMHEALHNHYTQKSLSLSPGK

G2m9:

(SEQ ID NO: 30)
VDKTVERKCCVECPPCPAPPVAGPSVFLFPPKPKDTLMISRTPEVTCVVV

DVEHEDPEVQFNWYVDGVEVHNAKTKPREEQFNSTFRVVSVLTVVHQDWL

NGKEYKCKVSNKGFPAPIEKTISKTKGQPREPQVYTLPPSREEMTKNQVS

LTCLVKGFYPSDIAVEWESNGQPENNYKTTPPMLDSDGSFFLYSKLTVDK

SRWQQGNVFSCSVMHEALHNHYTQKSLSLSPGK

G2m10:

(SEQ ID NO: 31)
VDKTVERKCCVECPPCPAPEVSSVFLFPPKPKDTLMISRTPEVTCVVVDV

SHEDPEVQFNWYVDGVEVHNAKTKPREEQFNSTFRVVSVLTVVHQDWLNG

KEYKCKVSNKGFPAPIEKTISKTKGQPREPQVYTLPPSREEMTKNQVSLT

CLVKGFYPSDIAVEWESNGQPENNYKTTPPMLDSDGSFFLYSKLTVDKSR

WQQGNVFSCSVMHEALHNHYTQKSLSLSPGK

G2m15:

(SEQ ID NO: 32)
VDKTVERKCCVECPPCPAPPVASVFLFPPKPKDTLMISRTPEVTCVVVDV

SHEDPEEQFNWYVDGVEVHNAKTKPREEQFNSTFRVVSVLTVVHQDWLNG

KEYKCKVSNKGLPAPIEKTISKTKGQPREPQVYTLPPSREEMTKNQVSLT

CLVKGFYPSDIAVEWESNGQPENNYKTTPPMLDSDGSFFLYSKLTVDKSR

WQQGNVFSCSVMHEALHNHYTQKSLSLSPGK

G2m17:

(SEQ ID NO: 33)
VDKTVERKCCVECPPCPAPPVASVFLFPPKPKDTLMISRTPEVTCVVVDV

EHEDPEVQFNWYVDGVEVHNAKTKPREEQFNSTFRVVSVLTVVHQDWLNG

KEYKCKVSNKGLPAPIEKTISKTKGQPREPQVYTLPPSREEMTKNQVSLT

CLVKGFYPSDIAVEWESNGQPENNYKTTPPMLDSDGSFFLYSKLTVDKSR

WQQGNVFSCSVMHEALHNHYTQKSLSLSPGK

G2m18:
(SEQ ID NO: 34)
VDKTVERKCCVECPPCPAPPVASVFLFPPKPKDTLMISRTPEVTCVVVDV
SHEDPEVQFNWYVDGVEVHNAKTKPREEQFNSTFRVVSVLTVVHQDWLNG
KEYKCKVSNKGFPAPIEKTISKTKGQPREPQVYTLPPSREEMTKNQVSLT
CLVKGFYPSDIAVEWESNGQPENNYKTTPPMLDSDGSFFLYSKLTVDKSR
WQQGNVFSCSVMHEALHNHYTQKSLSLSPGK

G2m19:
(SEQ ID NO: 35)
VDKTVERKCCVECPPCPAPPVASVFLFPPKPKDTLMISRTPEVTCVVVDV
EHEDPEVQFNWYVDGVEVHNAKTKPREEQFNSTFRVVSVLTVVHQDWLNG
KEYKCKVSNKGFPAPIEKTISKTKGQPREPQVYTLPPSREEMTKNQVSLT
CLVKGFYPSDIAVEWESNGQPENNYKTTPPMLDSDGSFFLYSKLTVDKSR
WQQGNVFSCSVMHEALHNHYTQKSLSLSPGK

G2m20:
(SEQ ID NO: 36)
VDKTVERKCCVECPPCPAPPVAPSVFLFPPKPKDTLMISRTPEVTCVVVD
VSHEDPEVQFNWYVDGVEVHNAKTKPREEQFNSTFRVVSVLTVVHQDWLN
GKEYKCKVSNKGLPAPIEKTISKTKGQPREPQVYTLPPSREEMTKNQVSL
TCLVKGFYPSDIAVEWESNGQPENNYKTTPPMLDSDGSFFLYSKLTVDKS
RWQQGNVFSCSVMHEALHNHYTQKSLSLSPGK

G2m27:
(SEQ ID NO: 37)
VDKTVERKCCVECPPCPAPPVAPSVFLFPPKPKDTLMISRTPEVTCVVVD
VSHEDPEVQFNWYVDGVEVHNAKTKPREEQFNSTFRVVSVLTVVHQDWLN
GKEYKCKVSNKGLPAPIEKTISKTKGQPREPQVYTLPPSREEMTKNQVSL
TCLVKGFYPSDIAVEWESNGQPENNYKTTPPMLDSDGSFFLYSKLTVDKS
RWQQGNVFSCSVMHEALHNHYTQKSLSLSPGK

Gbn28:
(SEQ ID NO: 38)
VDKTVERKCCVECPPCPAPPVAPSVFLFPPKPKDTLMISRTPEVTCVVVD
VEHEDPEVQFNWYVDGVEVHNAKTKPREEQFNSTFRVVSVLTVVHQDWLN
GKEYKCKVSNKGLPAPIEKTISKTKGQPREPQVYTLPPSREEMTKNQVSL
TCLVKGFYPSDIAVEWESNGQPENNYKTTPPMLDSDGSFFLYSKLTVDKS
RWQQGNVFSCSVMHEALHNHYTQKSLSLSPGK

Amino acid sequences of exemplary human IgG4 Fc
variants:
G4m1:
(SEQ ID NO: 39)
VDKRVESKYGPPCPPCPAPEFLSVFLFPPKPKDTLMISRTPEVTCVVVDV
SQEDPEVQFNWYVDGVEVHNAKTKPREEQFNSTYRVVSVLTVLHQDWLNG
KEYKCKVSNKGLPSSIEKTISKAKGQPREPQVYTLPPSQEEMTKNQVSLT
CLVKGFYPSDIAVEWESNGQPENNYKTTPPVLDSDGSFFLYSRLTVDKSR
WQEGNVFSCSVMHEALHNHYTQKSLSLSLGK G4m-1:
(SEQ ID NO: 40)
VDKRVESKSCDKTHTPPCPPCPAPEFLGGPSVFLFPPKPKDTLMISRTPE
VTCVVVDVSQEDPEVQFNWYVDGVEVHNAKTKPREEQFNSTYRVVSVLTV
LHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYS
RLTVDKSRWQEGNVFSCSVMHEALHNHYTQKSLSLSLGK G4m2:
(SEQ ID NO: 41)
VDKRVESKYGPPCPPCPAPEFLGPSVFLFPPKPKDTLMISRTPEVTCVVV
DVSQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDK
SRWQEGNVFSCSVMHEALHNHYTQKSLSLSLGK G4m-2:
(SEQ ID NO: 42)
VDKRVESKCCVEPPCPPCPAPEFLGGPSVFLFPPKPKDTLMISRTPEVTC
VVVDVSQEDPEVQFNWYVDGVEVHNAKTKPREEQFNSTYRVVSVLTVLHQ
DWLNGKEYKCKVSNKGLPSSIEKTISKAKGQPREPQVYTLPPSQEEMTKN
QVSLTCLVKGFYPSDIAVEWESNGQPENNYKTTPPVLDSDGSFFLYSRLT
VDKSRWQEGNVFSCSVMHEALHNHYTQKSLSLSLGK G4m3:
(SEQ ID NO: 43)
VDKRVESKYGPPCPPCPAPEFLGGPSVFLFPPKPKDTLMISRTPEVTCVV
VDVSQEDPEEQFNWYVDGVEVHNAKTKPREEQFNSTYRVVSVLTVLHQDW
LNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVD
KSRWQEGNVFSCSVMHEALHNHYTQKSLSLSLGK G4m4:
(SEQ ID NO: 44)
VDKRVESKYGPPCPPCPAPEFLSVFLFPPKPKDTLMISRTPEVTCVVVDV
SQEDPEEQFNWYVDGVEVHNAKTKPREEQFNSTYRVVSVLTVLHQDWLNG
KEYKCKVSNKGLPSSIEKTISKAKGQPREPQVYTLPPSQEEMTKNQVSLT
CLVKGFYPSDIAVEWESNGQPENNYKTTPPVLDSDGSFFLYSRLTVDKSR
WQEGNVFSCSVMHEALHNHYTQKSLSLSLGK G4m5:
(SEQ ID NO: 45)
VDKRVESKYGPPCPPCPAPEFLGGPSVFLFPPKPKDTLMISRTPEVTCVV
VDVSQEDPEEQFNWYVDGVEVHNAKTKPREEQFNSTYRVVSVLTVLHQDW
LNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVD
KSRWQEGNVFSCSVMHEALHNHYTQKSLSLSLGK G4m7:
(SEQ ID NO: 46)
VDKRVESKYGPPCPPCPAPEFLGGPSVFLFPPKPKDTLMISRTPEVTCVV
VDVEQEDPEVQFNWYVDGVEVHNAKTKPREEQFNSTYRVVSVLTVLHQDW
LNGKEYKCKVSNKGLPSSIEKTISKAKGQPREPQVYTLPPSQEEMTKNQV -continued SLTCLVKGFYPSDIAVEWESNGQPENNYKTTPPVLDSDGSFFLYSRLTVD
KSRWQEGNVFSCSVMHEALHNHYTQKSLSLSLGK G4m8:
(SEQ ID NO: 47)
VDKRVESKYGPPCPPCPAPEFLGGPSVFLFPPKPKDTLMISRTPEVTCVV
VDVSQEDPEVQFNWYVDGVEVHNAKTKPREEQFNSTYRVVSVLTVLHQDW
LNGKEYKCKVSNKGFPSSIEKTISKAKGQPREPQVYTLPPSQEEMTKNQV
SLTCLVKGFYPSDIAVEWESNGQPENNYKTTPPVLDSDGSFFLYSRLTVD
KSRWQEGNVFSCSVMHEALHNHYTQKSLSLSLGK G4m9:
(SEQ ID NO: 48)
VDKRVESKYGPPCPPCPAPEFLGGPSVFLFPPKPKDTLMISRTPEVTCVV
VDVEQEDPEVQFNWYVDGVEVHNAKTKPREEQFNSTYRVVSVLTVLHQDW
LNGKEYKCKVSNKGFPSSIEKTISKAKGQPREPQVYTLPPSQEEMTKNQV
SLTCLVKGFYPSDIAVEWESNGQPENNYKTTPPVLDSDGSFFLYSRLTVD
KSRWQEGNVFSCSVMHEALHNHYTQKSLSLSLGK G4m10:
(SEQ ID NO: 49)
VDKRVESKYGPPCPPCPAPEVSSVFLFPPKPKDTLMISRTPEVTCVVVDV
SQEDPEVQFNWYVDGVEVHNAKTKPREEQFNSTYRVVSVLTVLHQDWLNG
KEYKCKVSNKGFPSSIEKTISKAKGQPREPQVYTLPPSQEEMTKNQVSLT
CLVKGFYPSDIAVEWESNGQPENNYKTTPPVLDSDGSFFLYSRLTVDKSR
WQEGNVFSCSVMHEALHNHYTQKSLSLSLGK G4m15
(SEQ ID NO: 128)
VDKRVESKYGPPCPPCPAPEFLSVFLFPPKPKDTLMISRTPEVTCVVVDV
SQEDPEEQFNWYVDGVEVHNAKTKPREEQFNSTYRVVSVLTVLHQDWLNG
KEYKCKVSNKGLPSSIEKTISKAKGQPREPQVYTLPPSQEEMTKNQVSLT
CLVKGFYPSDIAVEWESNGQPENNYKTTPPVLDSDGSFFLYSRLTVDKSR
WQEGNVFSCSVMHEALHNHYTQKSLSLSLGK G4m17:
(SEQ ID NO: 50)
VDKRVESKYGPPCPPCPAPEFLSVFLFPPKPKDTLMISRTPEVTCVVVDV
EQEDPEVQFNWYVDGVEVHNAKTKPREEQFNSTYRVVSVLTVLHQDWLNG
KEYKCKVSNKGFPSSIEKTISKAKGQPREPQVYTLPPSQEEMTKNQVSLT
CLVKGFYPSDIAVEWESNGQPENNYKTTPPVLDSDGSFFLYSRLTVDKSR
WQEGNVFSCSVMHEALHNHYTQKSLSLSLGK G4m18:
(SEQ ID NO: 51)
VDKRVESKYGPPCPPCPAPEFLSVFLFPPKPKDTLMISRTPEVTCVVVDV
SQEDPEVQFNWYVDGVEVHNAKTKPREEQFNSTYRVVSVLTVLHQDWLNG
KEYKCKVSNKGFPSSIEKTISKAKGQPREPQVYTLPPSQEEMTKNQVSLT
CLVKGFYPSDIAVEWESNGQPENNYKTTPPVLDSDGSFFLYSRLTVDKSR
WQEGNVFSCSVMHEALHNHYTQKSLSLSLGK G4m19:
(SEQ ID NO: 52)
VDKRVESKYGPPCPPCPAPEFLSVFLFPPKPKDTLMISRTPEVTCVVVDV
EQEDPEVQFNWYVDGVEVHNAKTKPREEQFNSTYRVVSVLTVLHQDWLNG
KEYKCKVSNKGFPSSIEKTISKAKGQPREPQVYTLPPSQEEMTKNQVSLT
CLVKGFYPSDIAVEWESNGQPENNYKTTPPVLDSDGSFFLYSRLTVDKSR
WQEGNVFSCSVMHEALHNHYTQKSLSLSLGK G4m20:
(SEQ ID NO: 53)
VDKRVESKYGPPCPPCPAPEFLGSVFLFPPKPKDTLMISRTPEVTCVVVD
VSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDKS
RWQEGNVFSCSVMHEALHNHYTQKSLSLSLGK G4m25:
(SEQ ID NO: 54)
VDKRVESKYGPPCPPCPAPEFLGPSVFLFPPKPKDTLMISRTPEVTCVVV
DVSQEDPEEQFNWYVDGVEVHNAKTKPREEQFNSTYRVVSVLTVLHQDWL
NGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDK
SRWQEGNVFSCSVMHEALHNHYTQKSLSLSLGK G4m27:
(SEQ ID NO: 55)
VDKRVESKYGPPCPPCPAPEFLGPSVFLFPPKPKDTLMISRTPEVTCVVV
DVEQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDK
SRWQEGNVFSCSVMHEALHNHYTQKSLSLSLGK G4m28:
(SEQ ID NO: 56)
VDKRVESKYGPPCPPCPAPEFLGPSVFLFPPKPKDTLMISRTPEVTCVVV
DVSQEDPEVQFNWYVDGVEVHNAKTKPREEQFNSTYRVVSVLTVLHQDWL
NGKEYKCKVSNKGFPSSIEKTISKAKGQPREPQVYTLPPSQEEMTKNQVS
LTCLVKGFYPSDIAVEWESNGQPENNYKTTPPVLDSDGSFFLYSRLTVDK
SRWQEGNVFSCSVMHEALHNHYTQKSLSLSLGK G4m29:
(SEQ ID NO: 57)
VDKRVESKYGPPCPPCPAPEFLGPSVFLFPPKPKDTLMISRTPEVTCVVV
DVEQEDPEVQFNWYVDGVEVHNAKTKPREEQFNSTYRVVSVLTVLHQDWL
NGKEYKCKVSNKGFPSSIEKTISKAKGQPREPQVYTLPPSQEEMTKNQVS
LTCLVKGFYPSDIAVEWESNGQPENNYKTTPPVLDSDGSFFLYSRLTVDK
SRWQEGNVFSCSVMHEALHNHYTQKSLSLSLGK G4m30:
(SEQ ID NO: 58)
VDKRVESKYGPPCPPCPAPEFLPSVFLFPPKPKDTLMISRTPEVTCVVVD
VSQEDPEVQFNWYVDGVEVHNAKTKPREEQFNSTYRVVSVLTVLHQDWLN
GKEYKCKVSNKGLPSSIEKTISKAKGQPREPQVYTLPPSQEEMTKNQVSL
TCLVKGFYPSDIAVEWESNGQPENNYKTTPPVLDSDGSFFLYSRLTVDKS
RWQEGNVFSCSVMHEALHNHYTQKSLSLSLGK -continued G4mPE:
(SEQ ID NO: 59)
VDKRVESKYGPPCPPCPAPEFEGGPSVFLFPPKPKDTLMISRTPEVTCVV

VDVSQEDPEVQFNWYVDGVEVHNAKTKPREEQFNSTYRVVSVLTVLHQDW

LNGKEYKCKVSNKGLPSSIEKTISKAKGQPREPQVYTLPPSQEEMTKNQV

SLTCLVKGFYPSDIAVEWESNGQPENNYKTTPPVLDSDGSFFLYSRLTVD

KSRWQEGNVFSCSVMHEALHNHYTQKSLSLSLGK

The Fc variants described herein may exhibit an enhanced binding activity to FcγRIIB as compared with the wild-type counterpart. Examples include G2m2, G2m5, G2m7, G2m8, G2m9, G1m7, G1m9, and G4m7. Alternatively or in addition, the Fc variants may have an enhanced selectivity to FcγRIIB as compared with their wild-type counterparts, for example, G1m15, G1m17, G1m18, G1m19, G1m27, G1m28, G1m29, G4m1, G4m2, G4m7, G4m8, G4m9, G4m25, G4m27, and G4m28. These Fc variants can be used for constructing therapeutic agents described herein capable of cross-linking immune receptors and FcγRIIB receptor.

Alternatively, certain Fc variants as described herein may have low or no binding activity to any FcγR. Examples include G1m2, G1m25, G4m5, G4m18, G4m19, and G4m20. Such Fc variants may retain the binding activity to FcRn. Therapeutic agents (e.g., antibodies) containing such Fc variants would have low or no activity to activate Fcγ receptors and may have reduced toxicity relative to their wild-type counterparts.

The changes of binding affinity/specificity of the exemplary Fc variants as compared with their wild-type counterparts are provided in Tables 2-4 below, where N/A indicates no data available. When the binding activity of an Fc variant is found to be "no change" as compared with the wild-type counterpart, it means that there is no significant variation of the binding activity between the Fc variant and the wild-type counterpart as indicated by the same assay under the same experimental conditions. When the binding activity of an Fc variant is "increased" or "decreased" as relative to its wild-type counterpart means that the binding activity of the Fc variant is higher or lower than that of the wild-type counterpart as determined by the same assay under the same experimental conditions and the variation is significant (e.g., biologically significant) as known to those skilled in the art. When the binding activity of an Fc variant is "slightly increased" or "slightly decreased" as relative to its wild-type counterpart means that the binding activity of the Fc variant is higher or lower than that of the wild-type counterpart as determined by the same assay under the same experimental conditions and the variation is statistically significant but to a limited level (e.g., up to 10%).

TABLE 2

FcγR Binding Activity of Human IgG1
Mutants As Relative to Wild-Type Human IgG1

| IgG1 Mutant | Changes of Binding Activity Relative to Wild-Type Counterparts | | | | | |
|---|---|---|---|---|---|---|
| | FcγRI | FcγRIIA(H131) | FcγRIIA(R131) | FcγRIIB | FcγRIIC | FcγRIII |
| G1m1 | Decreased | Decreased | Decreased | Decreased | Decreased | Decreased |
| G1m2 | Decreased | Decreased | Decreased | Decreased | Decreased | Decreased |
| G1m-2 | No change | N/A | N/A | No change | N/A | No change |
| G1m-4 | No change | N/A | N/A | No change | N/A | No change |
| G1m5 | Increased | Increased | Increased | No change | Increased | Slightly decreased |
| G1m7 | Increased | Increased | Increased | Increased | Increased | Slightly decreased |
| G1m8 | Increased | Slightly decreased | No change | Increased | Slightly increased | Slightly decreased |
| G1m9 | Increased | Decreased | Increased | Increased | Increased | No change |
| G1m15 | Decreased | Decreased | Decreased | Decreased | Decreased | Decreased |
| G1m17 | Decreased | Decreased | Decreased | Decreased | Decreased | Decreased |
| G1m18 | Decreased | Decreased | No change | Decreased | Decreased | Decreased |
| G1m19 | Decreased | Increased | Increased | Increased | Increased | Decreased |
| G1m25 | Decreased | Decreased | Decreased | Decreased | Decreased | Decreased |
| G1m27 | Decreased | Decreased | Decreased | Increased | Decreased | Decreased |
| G1m28 | Decreased | Decreased | Decreased | Decreased | Decreased | Decreased |
| G1m29 | Decreased | Decreased | Increased | Increased | Increased | Decreased |
| G1mAA | Decreased | N/A | Decreased | Decreased | Decreased | Decreased |
| G1mAG | Decreased | N/A | Decreased | Decreased | Decreased | Decreased |

TABLE 3

FcγR Binding Activity of Human IgG2
Mutants As Relative to Wild-Type Human IgG2

| IgG2 Mutant | Change of Binding Activity Relative to Wild-Type Counterpart | | | | | |
|---|---|---|---|---|---|---|
| | FcγRI | FcγRIIA(H131) | FcγRIIA(R131) | FcγRIIB | FcγRIIC | FcγRIII |
| G2m1 | No change | Decreased | Decreased | Decreased | No change | No change |
| G2m2 | Increased | Decreased | No change | Increased | No change | No change |
| G2m10 | No change | Decreased | No change | Slightly decreased | No change | No change |

TABLE 3-continued

FcγR Binding Activity of Human IgG2
Mutants As Relative to Wild-Type Human IgG2

| IgG2 Mutant | Change of Binding Activity Relative to Wild-Type Counterpart | | | | | |
|---|---|---|---|---|---|---|
| | FcγRI | FcγRIIA(H131) | FcγRIIA(R131) | FcγRIIB | FcγRIIC | FcγRIII |
| G2m5 | Slightly increased | Decreased | No change | Decreased | No change | No change |
| G2m7 | No change | Slightly increased | Increased | Increased | Slightly increased | No change |
| G2m8 | No change | Decreased | No change | No change | No change | No change |
| G2m9 | No change | No change | Increased | Increased | Increased | No change |
| G2m-1 | Increased | N/A | N/A | Decreased | N/A | No change |
| G2m-4 | Increased | N/A | N/A | Decreased | N/A | No change |
| G2m15 | No change | N/A | N/A | Decreased | N/A | No change |
| G2m17 | No change | N/A | Increased | No change | Increased | No change |
| G2m18 | Slightly increased | N/A | No change | Decreased | No change | No change |
| G2m19 | No change | N/A | Increased | Increased | No change | No change |
| G2m20 | No change | N/A | Increased | Decreased | No change | No change |
| G2m27 | Slightly increased | N/A | N/A | Increased | N/A | No change |
| G2m28 | No change | N/A | N/A | Increased | N/A | No change |

TABLE 4

FcγR Binding Activity of Human IgG4
Mutants As Relative to Wild-Type Human IgG4

| IgG4 Mutant | Change of Binding Activity Relative to Wild-Type Counterpart | | | | | |
|---|---|---|---|---|---|---|
| | FcγRI | FcγRIIA(H131) | FcγRIIA(R131) | FcγRIIB | FcγRIIC | FcγRIII |
| G4m1 | Decreased | Increased | No change | Slightly decreased | Slightly increased | No change |
| G4m2 | Decreased | No change | Decreased | Slightly decreased | No change | No change |
| G4m10 | Decreased | No change | Decreased | Decreased | No change | No change |
| G4m20 | Decreased | No change | Decreased | Decreased | No change | No change |
| G4m3 | Decreased | No change | No change | Decreased | No change | No change |
| G4m7 | No change | Increased | Increased | Increased | Increased | Slightly increased |
| G4m8 | No change | No change | Increased | Slightly increased | No change | No change |
| G4m9 | No change | No change | Increased | Increased | Increased | No change |
| G4m17 | Decreased | No change | Increased | Increased | Increased | Increased |
| G4m18 | Decreased | No change | No change | Decreased | No change | Increased |
| G4m19 | Decreased | No change | No change | Decreased | No change | Slightly increased |
| G4m25 | Decreased | No change | Increased | Slightly decreased | No change | Increased |
| G4m27 | Decreased | No change | No change | Decreased | No change | Slightly increased |
| G4m28 | Decreased | No change | Slightly increased | Increased | Increased | No change |
| G4m29 | Decreased | No change | Increased | Increased | Increased | Slightly increased |
| G4m4 | Decreased | No change | No change | Decreased | No change | No change |
| G4m-1 | No change | N/A | N/A | No change | N/A | No change |
| G4m-2 | No change | N/A | N/A | Decreased | N/A | No change |
| G4mPE | Decreased | N/A | N/A | Slightly decreased | No change | No change |
| G4m30 | Decreased | N/A | No change | Decreased | No change | No change |

An Fc variant as described herein can be designed following the guidance provided herein and produced via routine recombinant technology. Its binding affinity and specificity to various Fc receptors can be determined via routine methods. See also Examples below.

II. Therapeutic Agents Capable of Cross-Linking Immune Receptors and FcγRIIB

Also provided herein are therapeutic agents that can cross-link immune receptors and FcγRIIB receptor. Such therapeutic agents are expected to possess enhanced agonistic effects to activate immune cells such as T cells and NK cells in certain microenviroment such as cancer and tumor draining lymph nodes, so as to elicit or enhance immune responses against invading pathogens or diseases cells.

(i) Binding Moieties

The therapeutic agents described herein contain at least two binding moieties. One binding moiety is capable of binding to an immune cell receptor expressed on cell surface, for example, receptors of the TNF superfamily. Examples include Fas receptor/FAS, TWEAK receptor/TNFRSF12A, 4-1BB/TNFRSF9/CD137, TACI/TNFRSF13B, BAFF R/TNFRSF13C, CD27/TNFRSF7, CD30/TNFRSF8, CD40/TNFRSF5, DR3/TNFRSF25, DR4/TNFRSF10A, DR5/TNFRSF10B, DR6/TNFRSF21, GITR/TNFRSF18, HVEM/TNFRSF14, Lymphotoxin-beta receptor/LTβR, OX40/TNFRSF4, TROY/TNFRSF19, RELT/TNFRSF19L, TNFRSF12A, TACI/TNFRSF13B, TL1A/TNFSF15, TNFRSF17, TNFR1/TNFRSF1A, TNFRSF11B, RANK/TNFRSF11A, TR1/TNFRSF11B, NGFR, EDA2R and TNFRII/TNFRSF1B. In some instances, the binding moiety to the immune cell receptor is an antibody-binding fragment (e.g., a Fab fragment or a single-chain antibody fragment).

The other binding moiety in the therapeutic agent is capable of binding to FcγRIIB In some instances, this binding moiety has a selective binding activity to FcγRIIB relative to another Fc receptor. Such a binding moiety can be any of the Fc variants described herein, which selectively or specifically binds FcγRIIB In some embodiments, the therapeutic agent that cross-links an immune cell receptor and FcγRIIB can be an antibody specific to the immune cell receptor and comprises an Fc fragment that has selective binding activity to FcγRIIB, e.g., those described herein. For example, the therapeutic agent can be an antibody that binds any of the TNF superfamily members known in the art or listed here (e.g., CD137) and have a hIgG1, hIgG2, or hIgG4 Fc variant as described herein. In some examples, the antibody is an agonistic antibody.

In some embodiments, the therapeutic agent is a bi-specific antibody comprising one antigen-binding moiety specific to the immune cell receptor as described herein and another antigen-binding moiety specific to an Fcγ receptor such as FcγRIIB (ii) Preparation of Therapeutic Agents Antibodies capable of binding to both an immune cell receptor such as a TNF superfamily member and FcγRIIB as described herein can be made as follows. Antibodies binding to the immune cell receptor can be prepared by any method known in the art. See, for example, Harlow and Lane, (1998) Antibodies: A Laboratory Manual, Cold Spring Harbor Laboratory, New York.

In some embodiments, antibodies specific to a target receptor (e.g., CD137) or an extracellular domain thereof can be made by the conventional hybridoma technology. The full-length target receptor or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-immune cell receptor monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of modulating the activity of the target immune cell receptor. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting or activating the activity of the immune cell receptor. It will be apparent to one of skill in the art that one or more polynucleotide changes can be made to the antibody and still maintain its binding specificity to the target receptor.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are XENOMOUSE™ from Amgen, Inc. (Fremont, Calif.) and HUMAB-MOUSE™ and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455.

Alternatively, antibody library technology, such as the phage display technology (McCafferty et al., (1990) Nature 348:552-553), yeast display technology, or mammalian cell display technology, can be used to isolated antibodies such as human antibodies specific to a target immune receptor.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Methods for constructing humanized antibodies are also well known in the art. See, e.g., Queen et al., Proc. Natl. Acad. Sci. USA, 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

Once an antibody capable of binding to a target immune cell receptor is obtained, its antigen-binding fragment can be conjugated to a suitable Fc fragment of a suitable IgG isoform, which can selectively binds FcgRIIB, for example, any of the Fc variants described herein via routine recombinant technology. In some instances, the antibody is first investigated for its agonistic effect to activate the immune cell receptor to which it binds. Such an agonistic antibody can be selected for making therapeutic agent described herein to enhance the agonistic effects.

The resultant antibody molecules can be produced via routine recombinant technology as exemplified below. Nucleic acids encoding the heavy and light chain of an antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad.

Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., Human Gene Therapy). One particular advantage of this tetracycline inducible switch is that it does not require the use of a tetracycline repressor-mammalian cells transactivator or repressor fusion protein, which in some instances can be toxic to cells (Gossen et al., Natl. Acad. Sci. USA, 89:5547-5551 (1992); Shockett et al., Proc. Natl. Acad. Sci. USA, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an antibody as described herein. The recombinant expression vector can be introduced into a suitable host cell (e.g., a dhfr-CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-immune cell receptor antibody and the other encoding the light chain of the same antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into a suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

The bioactivity of the antibodies described herein can be verified using assays known in the art or described herein.

(iii) Pharmaceutical Compositions

The antibodies as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ (polyoxyethylene sorbitan monolaurate), PLURONICS™ (polyoxyethylene-polyoxypropylene-polyoxyethylene copolymer) or polyethylene glycol (PEG).

In some examples, the pharmaceutical composition described herein comprises liposomes containing the antibodies (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., TWEEN™ (polyoxyethylene sorbitan monolaurate) 20, 40, 60, 80 or 85) and other sorbitans (e.g., SPAN™ (sorbitan monolaurate) 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™ (10% intravenous fat emulsion), LIPOSYN™ (intravenous fat emulsion), INFONUTROL™ (intravenous fat emulsion), LIPOFUNDIN™ (20% fat emulsion for infusion) and LIPIPHYSAN™ (intravenous lipid emulsion). The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The emulsion compositions can be those prepared by mixing an antibody with INTRALIPID™ (10% intravenous fat emulsion) or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

III. Therapeutic Applications

Any of the therapeutic agents (e.g., antibodies) capable of cross-linking an immune cell receptor and FcγRIIB described herein are useful for enhancing immune responses against invading pathogens and/or diseased cells such as cancer cells.

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. In some instances, the subject is a human patient having or at risk for a cell-mediated disease or disorder, such as cancer including but not limited to lung cancer, stomach cancer, liver cancer, breast cancer, skin cancer, pancreatic cancer, brain cancer, prostate cancer, bladder cancer, or colorectal cancer.

As used herein, "an effective amount" refers to the amount of each active agent required to confer therapeutic effect on the subject, either alone or in combination with one or more other active agents. In some embodiments, the therapeutic effect is modulating (e.g., activating) the target immune receptor, thereby triggering or enhancing immune responses mediated by the receptor. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antagonist. To assess efficacy of the antagonist, an indicator of the disease/disorder can be followed.

Generally, for administration of any of the therapeutic agents such as antibodies described herein, an initial candidate dosage can be about 2 mg/kg. For the purpose of the present disclosure, a typical daily dosage might range from about any of 0.1 mg/kg to 3 mg/kg to 30 mg/kg to 300 mg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. In some examples, the dosage of the therapeutic agents such as antibodies described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the antagonist, and the discretion of the attending physician. Typically the clinician will administer an antibody, until a dosage is reached that achieves the desired result. In some embodiments, the desired result is a decrease in thrombosis. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the antibodies described herein are administered to a subject in need of the treatment at an amount sufficient to activate the activity of the target receptor by at least 20% (e.g., 30%, 40%, 50%, 60%, 70%, 80%, 90% or greater) in vivo.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

The particular dosage regimen, i.e., dose, timing and repetition, used in the method described herein will depend on the particular subject and that subject's medical history.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents.

Treatment efficacy for a target disease/disorder can be assessed by methods well-known in the art.

The therapeutic agent described herein may be utilized in conjunction with other types of therapy for the target disease such as cancer. Additional anti-cancer therapy includes chemotherapy, surgery, radiation, gene therapy, and so forth. When a second therapeutic agent is used, such an agent can be administered simultaneously or sequentially (in any order) with the therapeutic agent described herein that cross-links an immune cell receptor and FcγRIIB.

When co-administered with an additional therapeutic agent, suitable therapeutically effective dosages for each agent may be lowered due to the additive action or synergy.

The treatments of the disclosure can be combined with other immunomodulatory treatments such as, e.g., therapeutic vaccines (including but not limited to GVAX, DC-based vaccines, etc.), or checkpoint inhibitors (including but not limited to agents that block CTLA4, PD1, LAGS, TIM3, etc.). Alternatively, the treatment of the present disclosure can be combined with a chemotherapeutic agent, for example, pyrimidine analogs (5-fluorouracil, floxuridine, capecitabine, gemcitabine and cytarabine), purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

For examples of additional useful agents see also Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

IV. Kits

The present disclosure also provides kits for use in enhancing the desired immune responses using any of the therapeutic agents described herein, for example, anti-TNF antibodies containing an Fc variant described herein that selectively binds FcγRIIB In some embodiments, the kit can comprise instructions for use in accordance with any of the methods described herein. The included instructions can comprise a description of administration of the therapeutic agent to treat, delay the onset, or alleviate a target disease as those described herein. The kit may further comprise a description of selecting an individual suitable for treatment based on identifying whether that individual has the target disease. In still other embodiments, the instructions comprise a description of administering a therapeutic agent such as an antibody to an individual at risk of the target disease.

The instructions relating to the use of the therapeutic agent generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a target disease or disorder such as cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is the therapeutic agent as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1. Engineering Human IgG1, IgG2 and IgG4 for Selective FcγR2B/CD32B Binding To verify the impact of mutations in the hinge domain of human IgG1, IgG2, and IgG4 on binding activity to FcγR2b/CD32B, the human Fc variants G1m1, G1m2, G2m1, G2m2, G2m10, G4m1, G4m10, and G4m20 disclosed herein were linked to the VH fragment of an anti-CD137 antibody and the corresponding IgG1, G2, and G4 CH1 fragments to produce a full-length IgG heavy chain.

These mutant IgG heavy chains were cloned, co-expressed with the light chain of the anti-CD137 antibody, and purified using standard molecular biology and antibody protocols. The amino acid sequences of the VH-CH1 fragment (VH domain italicized) and the light chain are provided below:

VH-CH1 (IgG1):
(SEQ ID NO: 60)
*EVQLVQSGAEVKKPGESLRISCKGSGYSFSTYWISWVRQMPGKGLEWMGK*

*IYPGDSYTNYSPSFQGQVTISADKSISTAYLQWSSLKASDTAMYYCARGY*

*GIFDYWGQGTLVTVSS*ASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTK

VH-CH1 (IgG2):
(SEQ ID NO: 61)
*EVQLVQSGAEVKKPGESLRISCKGSGYSFSTYWISWVRQMPGKGLEWMGK*

*IYPGDSYTNYSPSFQGQVTISADKSISTAYLQWSSLKASDTAMYYCARGY*

*GIFDYWGQGTLVTVSS*ASTKGPSVFPLAPCSRSTSESTAALGCLVKDYFP

EPVTVSWNSGALTSGVHTFPAVLQSSGLYSLSSVVTVPSSNFGTQTYTCN

VDHKPSNTK

VH-CH1 (IgG4):
(SEQ ID NO: 62)
*EVQLVQSGAEVKKPGESLRISCKGSGYSFSTYWISWVRQMPGKGLEWMGK*

*IYPGDSYTNYSPSFQGQVTISADKSISTAYLQWSSLKASDTAMYYCARGY*

-continued
*GIFDYWGQGTLVTVSS*ASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTK

Light Chain:
(SEQ ID NO: 63)
SYELTQPPSVSVSPGQTASITCSGDNIGDQYAHWYQQKPGQSPVLVIYQD

KNRPSGIPERFSGSNSGNTATLTISGTQAMDEADYYCATYTGFGSLAVFG

GGTKLTVLGQPKAAPSVTLFPPSSEELQANKATLVCLISDFYPGAVTVAW

KADSSPVKAGVETTTPSKQSNNKYAASSYLSLTPEQWKSHRSYSCQVTHE

GSTVEKTVAPTECS

These IgG mutants were tested for binding to a panel of human Fc receptors (FcRs), including FcRn, using the Octet Red96 System (ForteBio, Model #Red96). Human FcR proteins were purchased commercially (FcRn, MednaBio, E1032; FcRI, MednaBio, E1031; FcRIIA, MednaBio, E1033; FcRIIB/C, MednaBio, E1034; FcRIIIA-F158, MednaBio, E1036; FcRIIIA-V158, MednaBio, E1035; FcRIIIB, MednaBio, E1037). All Fcγ receptor assays were performed at pH 7.2; all FcRn assays were performed at pH 6. The Fcγ receptors were loaded onto anti-penta-HIS1K (ForteBio, Cat #18-5122) biosensors at a concentration of 20 µg/mL. The loaded biosensors was then be dipped into an 8-point 1:3 dilution series of the test IgG molecules (including controls and the mutants described herein) in PBS with 0.1% BSA, 0.02% Tween-20 (pH 7.2) at a starting concentration of 300 nM. Kinetic analysis was performed using a 1:1 binding model and global fitting. The results are shown in Tables 5 and 6 below.

TABLE 5

FcgR Binding Activity of IgG1 and IgG2 Mutants to Various Fc Receptors

| | | IgG1 | IgG2 | IgG4 | G1m1 | G1m2 | G2m1 | G2m2 | G2m10 |
|---|---|---|---|---|---|---|---|---|---|
| FcγRI | KD (M) | 5.6E−9 | No | 4.8E−09 | 2.0E−07 | No | No | 2.0E−09 | No |
| | kon(1/Ms) | 2.2E+05 | No | 3.6E+05 | 6.5E+05 | No | No | 4.4E+05 | No |
| | kdis(1/s) | 1.2E−03 | No | 1.7E−03 | 1.3E−01 | No | No | 9.1E−04 | No |
| FcγRIIA | KD (M) | 5.6E−08 | 8.9E−08 | 4.0E−07 | 4.4E−07 | No | No | 6.8E−08 | 1.70E−05 |
| | kon(1/Ms) | 5.7E+05 | 4.4E+05 | 1.4E+05 | 2.5E+05 | No | No | 8.4E+05 | 2.10E+04 |
| | kdis(1/s) | 3.2E−02 | 3.9E−02 | 5.5E−02 | 1.1E−01 | No | No | 5.7E−02 | 3.50E−01 |
| FcγRIIB | KD (M) | 1.3E−07 | No | 4.0E−07 | No | No | No | 1.6E−07 | No |
| | kon(1/Ms) | 1.2E+05 | No | 1.4E+05 | No | No | No | 6.2E+05 | No |
| | kdis(1/s) | 1.6E−02 | No | 5.0E−02 | No | No | No | 9.9E−02 | No |
| FcγRIIIA(F) | KD (M) | 1.2E−07 | No | No | 3.0E−07 | No | No | 2.5E−07 | No |
| | kon(1/Ms) | 1.7E+05 | No | No | 3.5E+05 | No | No | 2.8E+05 | No |
| | kdis(1/s) | 2.0E−02 | No | No | 1.0E−01 | No | No | 7.0E−02 | No |
| FcγRIIIA(V) | KD (M) | 6.0E−08 | No | 5.5E−07 | No | No | No | 1.6E−07 | No |
| | kon(1/Ms) | 4.5E+05 | No | 1.7E+05 | No | No | No | 2.1E+05 | No |
| | kdis(1/s) | 2.7E−02 | No | 9.2E−02 | No | No | No | 3.3E−02 | No |
| FcγRIIIB | KD (M) | 1.3E−07 | No | No | No | No | Low | No | No |
| | kon(1/Ms) | 2.1E+05 | No | No | No | No | Low | No | No |
| | kdis(1/s) | 2.7E−02 | No | No | No | No | Low | No | No |
| FcRn | KD (M) | 1.6E−08 | 1.0E−08 | 1.8E−08 | 1.1E−08 | 1.3E−08 | 5.5E−09 | 1.0E−08 | 2.10E−08 |
| | kon(1/Ms) | 4.8E+05 | 9.9E+05 | 6.4E+05 | 7.0E+05 | 7.1E+05 | 1.7E+05 | 9.0E+05 | 4.20E+05 |
| | kdis(1/s) | 8.0E−03 | 9.9E−03 | 1.2E−02 | 7.8E−03 | 9.3E−03 | 9.6E−04 | 9.1E−03 | 8.80E−03 |

TABLE 6

FcγR Binding Activity of IgG4 Mutants

| | | IgG1 | IgG2 | IgG4 | G4m1 | G4m2 | G4m10 | G4m20 |
|---|---|---|---|---|---|---|---|---|
| FcγRI | KD (M) | 5.6E−9 | No | 4.8E−09 | 1.3E−07 | No | No | No |
| | kon(1/Ms) | 2.2E+05 | No | 3.6E+05 | 7.4E+05 | No | No | No |
| | kdis(1/s) | 1.2E−03 | No | 1.7E−03 | 9.7E−02 | No | No | No |

TABLE 6-continued

FcγR Binding Activity of IgG4 Mutants

|  |  | IgG1 | IgG2 | IgG4 | G4m1 | G4m2 | G4m10 | G4m20 |
|---|---|---|---|---|---|---|---|---|
| FcγRIIA | KD (M) | 5.6E−08 | 8.9E−08 | 4.0E−07 | 4.5E−07 | No | 8.30E−08 | No |
|  | kon(1/Ms) | 5.7E+05 | 4.4E+05 | 1.4E+05 | 2.4E+05 | No | 4.50E+05 | No |
|  | kdis(1/s) | 3.2E−02 | 3.9E−02 | 5.5E−02 | 1.1E−01 | No | 3.70E−02 | No |
| FcγRIIB | KD (M) | 1.3E−07 | No | 4.0E−07 | 2.5E−07 | 1.5E−07 | No | No |
|  | kon(1/Ms) | 1.2E+05 | No | 1.4E+05 | 4.2E+05 | 3.1E+05 | No | No |
|  | kdis(1/s) | 1.6E−02 | No | 5.0E−02 | 1.1E−01 | 4.6E−02 | No | No |
| FcγRIIIA(F) | KD (M) | 1.2E−07 | No | No | No | No | No | No |
|  | kon(1/Ms) | 1.7E+05 | No | No | No | No | No | No |
|  | kdis(1/s) | 2.0E−02 | No | No | No | No | No | No |
| FcgRIIIA(V) | KD (M) | 6.0E−08 | No | 5.5E−07 | No | No | No | No |
|  | kon(1/Ms) | 4.5E+05 | No | 1.7E+05 | No | No | No | No |
|  | kdis(1/s) | 2.7E−02 | No | 9.2E−02 | No | No | No | No |
| FcgRIIIB | KD (M) | 1.3E−07 | No | No | No | No | No | No |
|  | kon(1/Ms) | 2.1E+05 | No | No | No | No | No | No |
|  | kdis(1/s) | 2.7E−02 | No | No | No | No | No | No |
| FcRn | KD (M) | 1.6E−08 | 1.0E−08 | 1.8E−08 | 1.9E−08 | 9.8E−09 | 1.10E−08 | 1.9E−08 |
|  | kon(1/Ms) | 4.8E+05 | 9.9E+05 | 6.4E+05 | 6.9E+05 | 1.4E+06 | 5.10E+05 | 5.1E+05 |
|  | kdis(1/s) | 8.0E−03 | 9.9E−03 | 1.2E−02 | 1.3E−02 | 1.3E−02 | 5.50E−03 | 9.8E−03 |

Certain IgG mutants tested in this study, for example, G4m2, showed selective binding activity to FcγRIIB (CD32B), and also maintained binding activity to FcRn, which is important for the half-life of the IgG molecule in vivo. Others, such as G1m2, G2m1 or G4m20 lost binding to all FcγRs.

Example 2. Additional IgG1, IgG2, and IgG4 Mutants and Binding Activities to Various Fc Receptors The human Fc variants G1m5, G1m7, G1m8, G1m9, G2m5, G2m7, G2m8, G2m9, G4m5, G4m7, G4m8, and G4m9 disclosed herein were linked to the VH fragment of an anti-CD137 antibody and the corresponding IgG1, G2, and G4 CH1 fragments to produce a full-length IgG heavy chain. See Example 1 above. These mutant IgG heavy chains were cloned, co-expressed with the light chain of the anti-CD137 antibody (see Example 1 above), and purified using standard molecular biology and antibody protocols. The results are shown in Tables 7-9 below.

TABLE 7

FcR Binding Activity of IgG1 Mutants

|  |  | IgG1 | IgG2 | IgG4 | G1m5 | G1m7 | G1m8 | G1m9 | G1mAA |
|---|---|---|---|---|---|---|---|---|---|
| FcγRI | KD (M) | 5.6E−9 | No | 4.8E−09 | 1.6E−09 | 2.5E−09 | 2.5E−09 | 3.1E−09 | 2.35E−07 |
|  | kon(1/Ms) | 2.2E+05 | No | 3.6E+05 | 3.0E+05 | 6.3E+05 | 6.3E+05 | 5.1E+05 | 1.44E+05 |
|  | kdis(1/s) | 1.2E−03 | No | 1.7E−03 | 4.7E−04 | 1.6E−03 | 1.6E−03 | 1.6E−03 | 3.37E−02 |
| FcγRIIA | KD (M) | 5.6E−08 | 8.9E−08 | 4.0E−07 | 6.7E−07 | 2.9E−07 | 2.7E−07 | 6.8E−07 | 8.00E−07 |
|  | kon(1/Ms) | 5.7E+05 | 4.4E+05 | 1.4E+05 | 3.4E+05 | 3.8E+05 | 6.1E+05 | 1.8E+05 | 3.10E+05 |
|  | kdis(1/s) | 3.2E−02 | 3.9E−02 | 5.5E−02 | 2.3E−01 | 1.1E−01 | 1.7E−01 | 1.3E−01 | 2.47E−01 |
| FcγRIIB | KD (M) | 1.3E−07 | No | 4.0E−07 | 6.4E−07 | 1.1E−07 | 4.2E−07 | 2.5E−08 | 6.56E−07 |
|  | kon(1/Ms) | 1.2E+05 | No | 1.4E+05 | 2.8E+05 | 2.8E+05 | 2.7E+05 | 2.0E+05 | 2.38E+05 |
|  | kdis(1/s) | 1.6E−02 | No | 5.0E−02 | 1.8E−01 | 3.2E−02 | 1.1E−01 | 5.1E−03 | 1.56E−01 |
| FcγRIIIA(F) | KD (M) | 1.2E−07 | No | No | No | 1.4E−07 | 2.6E−07 | 1.8E−07 | 1.50E−06 |
|  | kon(1/Ms) | 1.7E+05 | No | No | No | 3.5E+05 | 2.2E+05 | 5.2E+05 | 1.16E+05 |
|  | kdis(1/s) | 2.0E−02 | No | No | No | 5.0E−02 | 5.7E−02 | 9.1E−02 | 1.75E−01 |
| FcγRIIIA(V) | KD (M) | 6.0E−08 | No | 5.5E−07 | 2.9E−07 | 8.7E−08 | 2.3E−07 | 8.6E−08 | 4.56E−07 |
|  | kon(1/Ms) | 4.5E+05 | No | 1.7E+05 | 2.5E+05 | 4.4E+05 | 3.2E+05 | 1.2E+06 | 9.23E+04 |
|  | kdis(1/s) | 2.7E−02 | No | 9.2E−02 | 7.3E−02 | 3.9E−02 | 7.4E−02 | 1.0E−01 | 4.20E−02 |
| FcγRIIIB | KD (M) | 1.3E−07 | No | No | No | No | No | No | 5.56E−07 |
|  | kon(1/Ms) | 2.1E+05 | No | No | No | No | No | No | 2.58E+05 |
|  | kdis(1/s) | 2.7E−02 | No | No | No | No | No | No | 1.44E−01 |
| FcRn | KD (M) | 1.6E−08 | 1.0E−08 | 1.8E−08 | 2.2E−08 | 1.5E−08 | 1.65E−08 | 1.91E−08 | 1.88E−08 |
|  | kon(1/Ms) | 4.8E+05 | 9.9E+05 | 6.4E+05 | 3.5E+05 | 6.7E+05 | 6.73E+05 | 6.07E+05 | 8.03E+05 |
|  | kdis(1/s) | 8.0E−03 | 9.9E−03 | 1.2E−02 | 7.7E−03 | 1.0E−02 | 1.11E−02 | 1.16E−02 | 1.50E−02 |

TABLE 8

FcR Binding Activity of IgG2 Mutants

| | | IgG1 | IgG2 | IgG4 | G2m5 | G2m7 | G2m8 | G2m9 |
|---|---|---|---|---|---|---|---|---|
| FcγRI | KD (M) | 5.6E−9 | No | 4.8E−09 | No | No | No | No |
| | kon(1/Ms) | 2.2E+05 | No | 3.6E+05 | No | No | No | No |
| | kdis(1/s) | 1.2E−03 | No | 1.7E−03 | No | No | No | No |
| FcγRIIA | KD (M) | 5.6E−08 | 8.9E−08 | 4.0E−07 | 2.30E−07 | 1.20E−07 | 9.30E−08 | 2.80E−07 |
| | kon(1/Ms) | 5.7E+05 | 4.4E+05 | 1.4E+05 | 6.00E+05 | 2.30E+05 | 9.90E+05 | 1.10E+05 |
| | kdis(1/s) | 3.2E−02 | 3.9E−02 | 5.5E−02 | 1.40E−01 | 2.80E−02 | 9.20E−02 | 3.00E−02 |
| FcγRIIB | KD (M) | 1.3E−07 | No | 4.0E−07 | 3.10E−07 | 1.70E−07 | 5.00E−07 | 5.20E−08 |
| | kon(1/Ms) | 1.2E+05 | No | 1.4E+05 | 3.90E+05 | 3.10E+05 | 5.10E+05 | 9.70E+04 |
| | kdis(1/s) | 1.6E−02 | No | 5.0E−02 | 1.20E−01 | 5.20E−02 | 2.60E−01 | 5.00E−03 |
| FcγRIIIA(F) | KD (M) | 1.2E−07 | No | No | No | No | No | No |
| | kon(1/Ms) | 1.7E+05 | No | No | No | No | No | No |
| | kdis(1/s) | 2.0E−02 | No | No | No | No | No | No |
| FcγRIIIA(V) | KD (M) | 6.0E−08 | No | 5.5E−07 | No | No | No | No |
| | kon(1/Ms) | 4.5E+05 | No | 1.7E+05 | No | No | No | No |
| | kdis(1/s) | 2.7E−02 | No | 9.2E−02 | No | No | No | No |
| FcγRIIIB | KD (M) | 1.3E−07 | No | No | No | No | No | No |
| | kon(1/Ms) | 2.1E+05 | No | No | No | No | No | No |
| | kdis(1/s) | 2.7E−02 | No | No | No | No | No | No |
| FcRn | KD (M) | 1.6E−08 | 1.0E−08 | 1.8E−08 | 1.40E−08 | 5.70E−09 | 6.30E−09 | 2.20E−08 |
| | kon(1/Ms) | 4.8E+05 | 9.9E+05 | 6.4E+05 | 8.00E+05 | 9.10E+05 | 8.50E+05 | 2.70E+05 |
| | kdis(1/s) | 8.0E−03 | 9.9E−03 | 1.2E−02 | 1.10E−02 | 5.20E−03 | 5.30E−03 | 5.80E−03 |

TABLE 9

FcR Binding Activity of IgG4 Mutants

| | | IgG1 | IgG2 | IgG4 | G4m5 | G4m7 | G4m8 | G4m9 | G4m30 | G4PE |
|---|---|---|---|---|---|---|---|---|---|---|
| FcγRI | KD (M) | 5.6E−9 | No | 4.8E−09 | N.D. | 2.10E−09 | 3.80E−09 | 1.70E−08 | 5.28E−07 | 6.05E−07 |
| | kon(1/Ms) | 2.2E+05 | No | 3.6E+05 | N.D. | 5.40E+05 | 7.20E+05 | 4.40E+05 | 3.65E+05 | 1.02E+05 |
| | kdis(1/s) | 1.2E−03 | No | 1.7E−03 | N.D. | 1.10E−03 | 2.80E−03 | 7.40E−03 | 1.93E−01 | 6.17E−02 |
| FcγRIIA | KD (M) | 5.6E−08 | 8.9E−08 | 4.0E−07 | N.D. | 2.10E−07 | 2.60E−07 | No | 9.77E−07 | 5.45E−08 |
| | kon(1/Ms) | 5.7E+05 | 4.4E+05 | 1.4E+05 | N.D. | 1.60E+05 | 3.90E+05 | No | 2.40E+05 | 4.69E+05 |
| | kdis(1/s) | 3.2E−02 | 3.9E−02 | 5.5E−02 | N.D. | 3.40E−02 | 1.00E−01 | No | 2.34E−01 | 2.56E−02 |
| FcγRIIB | KD (M) | 1.3E−07 | No | 4.0E−07 | N.D. | 4.50E−08 | 8.90E−08 | 1.40E−07 | 2.22E−06 | 3.07E−08 |
| | kon(1/Ms) | 1.2E+05 | No | 1.4E+05 | N.D. | 4.40E+05 | 5.30E+05 | 9.40E+04 | 5.36E+04 | 4.01E+05 |
| | kdis(1/s) | 1.6E−02 | No | 5.0E−02 | N.D. | 2.00E−02 | 4.80E−02 | 1.30E−02 | 1.18E−01 | 1.23E−02 |
| FcγRIIIA (F) | KD (M) | 1.2E−07 | No | No | N.D. | No | No | No | 2.84E−07 | 1.45E−07 |
| | kon(1/Ms) | 1.7E+05 | No | No | N.D. | No | No | No | 1.06E+06 | 4.68E+05 |
| | kdis(1/s) | 2.0E−02 | No | No | N.D. | No | No | No | 3.03E−01 | 6.78E−02 |
| FcγRIIIA (V) | KD (M) | 6.0E−08 | No | 5.5E−07 | N.D. | No | No | No | 2.17E−07 | 2.02E−07 |
| | kon(1/Ms) | 4.5E+05 | No | 1.7E+05 | N.D. | No | No | No | 1.42E+06 | 2.96E+05 |
| | kdis(1/s) | 2.7E−02 | No | 9.2E−02 | N.D. | No | No | No | 3.09E−01 | 5.96E−02 |
| FcγRIIIB | KD (M) | 1.3E−07 | No | No | N.D. | No | No | No | 2.16E−07 | 1.32E−07 |
| | kon(1/Ms) | 2.1E+05 | No | No | N.D. | No | No | No | 1.37E+06 | 4.37E+05 |
| | kdis(1/s) | 2.7E−02 | No | No | N.D. | No | No | No | 2.97E−01 | 5.79E−02 |
| FcRn | KD (M) | 1.6E−08 | 1.0E−08 | 1.8E−08 | N.D. | 2.30E−08 | 2.00E−08 | 7.50E−08 | 7.61E−09 | 2.19E−08 |
| | kon(1/Ms) | 4.8E+05 | 9.9E+05 | 6.4E+05 | N.D. | 5.20E+05 | 6.10E+05 | 2.30E+05 | 1.75E+06 | 6.98E+05 |
| | kdis(1/s) | 8.0E−03 | 9.9E−03 | 1.2E−02 | N.D. | 1.20E−02 | 1.20E−02 | 1.70E−02 | 1.33E−02 | 1.52E−02 |

Example 3. Exemplary IgG Mutants Having Combined Mutations to Enhance Selective Binding to FcγRIIB (CD32B)

The human Fc variants G1m15, G1m17, G1m18, G1m19, G2m25, G2m27, G2m28, G4m15, G4m17, G4m18, and G4m19, G4m25, G4m27, G4m28, and G4m29 disclosed herein were linked to the VH fragment of an anti-CD137 antibody and the corresponding IgG1, G2, and G4 CH1 fragments to produce a full-length IgG heavy chain. See Example 1 above. These Fc variants contain a combination of one or mutations in the hinge domain and one or more mutations in the CH2 and/or CH3 domains. These mutant IgG heavy chains were cloned, co-expressed with the light chain of the anti-CD137 antibody (see Example 1 above), and purified using standard molecular biology and antibody protocols. The results are shown in Tables 10-12 below.

Example 4. Determination of Human IgG Mutants Binding Activity to Cellular FcγR To determine the binding activity of human IgG mutants to cellular Fc receptors, CHO cells were genetically engineered to express human FcγRs (FcγRI, FcγRIIA (H131), FcγRIIA (R131), FcγRIIB, FcγRIIC, and FcγRIII) using a lentivirus delivery system as known in the art.

IgG Fc mutants, including G1m-2, G1m-4, G1mAA, G1mAG, G2m-1 G2m-4, G2m15, G2m17, G2m17, G2m18, G2m19, G2m20, G2m27, G2m28, G4m-1, G4m-2, G430, and G4PE (amino acid sequences provided above) were designed and constructed following the disclosures herein. These IgG mutants contain mutations in either the upper hinge domain or the lower hinge domain as indicated.

For FACS analysis of the IgG mutants' binding to different FcγRs, FcγR overexpressing CHO cells were harvested using trypsin-EDTA and were suspended in cold staining buffer (3% BSA in PBS). Test IgG mutants, which were diluted in staining buffer, were added into the cells. The mixture was incubated 4° C. for 2 hours, and then washed twice with cold staining buffer and re-suspended in PE-labeled anti-human IgG followed by incubation at 4° C. for 2 hours. The mixture was washed twice with staining buffer and resuspended in 2% PFA in PBS for FACS.

TABLE 10

FcR Binding Activity of Human IgG1 Mutants

| | | IgG1 | G1m15 | G1m17 | G1m18 | G1m19 | G1m25 | G1m27 | G1m28 | G1m29 |
|---|---|---|---|---|---|---|---|---|---|---|
| FcγRI | KD (M) | 5.6E-9 | 1.2E-07 | 8.8E-08 | 2.6E-07 | 1.2E-07 | No | No | 2.4E-07 | 3.7E-08 |
| | kon(1/Ms) | 2.2E+05 | 5.0E+05 | 4.6E+05 | 8.3E+05 | 7.1E+05 | No | No | 6.4E+05 | 2.6E+05 |
| | kdis(1/s) | 1.2E-03 | 6.0E-02 | 4.1E-02 | 2.1E-01 | 8.6E-02 | No | No | 1.6E-01 | 9.8E-03 |
| FcγRIIA | KD (M) | 5.6E-08 | 4.8E-07 | 2.5E-07 | 1.4E-07 | 8.1E-08 | No | No | No | 5.3E-07 |
| | kon(1/Ms) | 5.7E+05 | 2.3E+05 | 2.4E+05 | 2.0E+05 | 2.4E+05 | No | No | No | 2.6E+05 |
| | kdis(1/s) | 3.2E-02 | 1.1E-01 | 5.9E-02 | 2.9E-02 | 1.9E-02 | No | No | No | 1.4E-01 |
| FcγRIIB | KD (M) | 1.3E-07 | 7.0E-07 | 1.8E-07 | 6.7E-07 | 1.1E-07 | No | 4.1E-07 | 4.1E-07 | 4.6E-08 |
| | kon(1/Ms) | 1.2E+05 | 5.4E+05 | 2.4E+05 | 5.8E+05 | 2.6E+05 | No | 2.6E+05 | 4.8E+05 | 2.5E+05 |
| | kdis(1/s) | 1.6E-02 | 3.8E-01 | 4.3E-02 | 3.9E-01 | 2.8E-02 | No | 1.0E-01 | 2.0E-01 | 1.1E-02 |
| FcγRIIIA (F) | KD (M) | 1.2E-07 | No | No | No | No | No | No | No | No |
| | kon(1/Ms) | 1.7E+05 | No | No | No | No | No | No | No | No |
| | kdis(1/s) | 2.0E-02 | No | No | No | No | No | No | No | No |
| FcγRIIIA (V) | KD (M) | 6.0E-08 | No | No | No | No | No | No | No | No |
| | kon(1/Ms) | 4.5E+05 | No | No | No | No | No | No | No | No |
| | kdis(1/s) | 2.7E-02 | No | No | No | No | No | No | No | No |
| FcgRIIIB | KD (M) | 1.3E-07 | No | No | No | No | No | No | No | No |
| | kon(1/Ms) | 2.1E+05 | No | No | No | No | No | No | No | No |
| | kdis(1/s) | 2.7E-02 | No | No | No | No | No | No | No | No |
| FcRn | KD (M) | 1.6E-08 | 2.1E-08 | 1.07E-08 | 1.28E-08 | 1.34E-08 | 1.5E-08 | 1.6E-08 | 1.7E-08 | 1.7E-08 |
| | kon(1/Ms) | 4.8E+05 | 6.0E+05 | 7.15E+05 | 6.30E+05 | 7.70E+05 | 6.2E+05 | 6.5E+05 | 6.5E+05 | 7.6E+05 |
| | kdis(1/s) | 8.0E-03 | 1.3E-02 | 7.64E-03 | 8.03E-03 | 1.03E-02 | 9.3E-03 | 1.0E-02 | 1.1E-02 | 1.3E-02 |

TABLE 11

FcR Binding Activity of Human IgG2 Mutants

| | | IgG2 | G2m17 | G2m19 | G2m20 | G2m28 |
|---|---|---|---|---|---|---|
| FcγRI | KD (M) | No | 2.53E-07 | No | No | 6.61E-08 |
| | kon(1/Ms) | No | 1.09E+06 | No | No | 1.49E+06 |
| | kdis(1/s) | No | 2.77E-01 | No | No | 9.80E-02 |
| FcγRIIA | KD (M) | 8.9E-08 | 4.22E-07 | 3.36E-07 | 8.29E-07 | 1.91E-07 |
| | kon(1/Ms) | 4.4E+05 | 6.48E+05 | 2.49E+05 | 1.99E+04 | 4.70E+05 |
| | kdis(1/s) | 3.9E-02 | 2.74E-01 | 8.36E-02 | 1.65E-02 | 8.98E-02 |
| FcγRIIB | KD (M) | No | 2.36E-07 | 2.40E-07 | 5.17E-07 | 2.56E-07 |
| | kon(1/Ms) | No | 3.61E+05 | 1.62E+05 | 1.76E+05 | 1.81E+05 |
| | kdis(1/s) | No | 8.48E-02 | 3.87E-02 | 9.15E-02 | 4.64E-02 |
| FcγRIIIA (F) | KD (M) | No | 1.68E-07 | No | 9.17E-07 | 5.27E-07 |
| | kon(1/Ms) | No | 1.56E+06 | No | 1.43E+04 | 4.87E+05 |
| | kdis(1/s) | No | 2.62E-01 | No | 1.30E-02 | 2.57E-01 |
| FcγRIIIA (V) | KD (M) | No | 1.53E-07 | No | 1.26E-06 | No |
| | kon(1/Ms) | No | 1.34E+06 | No | 1.18E+04 | No |
| | kdis(1/s) | No | 2.05E-01 | No | 1.49E-02 | No |
| FcγRIIIB | KD (M) | No | 1.17E-07 | No | No | No |
| | kon(1/Ms) | No | 1.74E+06 | No | No | No |
| | kdis(1/s) | No | 2.04E-01 | No | No | No |
| FcRn | KD (M) | 1.0E-08 | 7.46E-09 | 3.54E-08 | 5.76E-08 | 2.64E-08 |
| | kon(1/Ms) | 19.9+E05 | 1.87E+06 | 2.65E+05 | 2.12E+05 | 7.37E+05 |
| | kdis(1/s) | 9.9E+03 | 1.39E-02 | 9.41E-03 | 1.22E-02 | 1.95E-02 |

TABLE 12

FcR Binding Activity of Human IgG4 Mutants

| | | IgG4 | G4m15 | G4m17 | G4m18 | G4m19 | G4m25 | G4m27 | G4m28 | G4m29 |
|---|---|---|---|---|---|---|---|---|---|---|
| FcγRI | KD (M) | 4.8E-09 | N.D. | No | Low | Low | 4.6E-08 | 6.6E-08 | 5.6E-08 | 4.4E-08 |
| | kon(1/Ms) | 3.6E+05 | N.D. | No | Low | Low | 3.8E+05 | 3.7E+05 | 4.9E+05 | 5.2E+05 |
| | kdis(1/s) | 1.7E-03 | N.D. | No | Low | Low | 1.7E-02 | 2.5E-02 | 2.7E-02 | 2.3E-02 |
| FcγRIIA | KD (M) | 4.0E-07 | N.D. | 6.0E-07 | Low | Low | 6.6E-07 | Low | 1.8E-06 | 2.6E-07 |
| | kon(1/Ms) | 1.4E+05 | N.D. | 4.0E+04 | Low | Low | 5.7E+04 | Low | 3.1E+04 | 1.0E+05 |
| | kdis(1/s) | 5.5E-02 | N.D. | 2.4E-02 | Low | Low | 3.8E-02 | Low | 5.5E-02 | 2.7E-02 |

TABLE 12-continued

FcR Binding Activity of Human IgG4 Mutants

|  |  | IgG4 | G4m15 | G4m17 | G4m18 | G4m19 | G4m25 | G4m27 | G4m28 | G4m29 |
|---|---|---|---|---|---|---|---|---|---|---|
| FcγRIIB | KD (M) | 4.0E−07 | N.D. | 2.8E−07 | No | Low | 2.4E−07 | 3.1E−07 | 1.8E−07 | 7.8E−08 |
|  | kon(1/Ms) | 1.4E+05 | N.D. | 6.8E+04 | No | Low | 1.3E+05 | 1.3E+05 | 1.9E+05 | 1.7E+05 |
|  | kdis(1/s) | 5.0E−02 | N.D. | 1.9E−02 | No | Low | 3.0E−02 | 3.9E−02 | 3.4E−02 | 1.3E−02 |
| FcγRIIIA (F) | KD (M) | No | N.D. | No | No | No | No | No | No | No |
|  | kon(1/Ms) | No | N.D. | No | No | No | No | No | No | No |
|  | kdis(1/s) | No | N.D. | No | No | No | No | No | No | No |
| FcγRIIIA (V) | KD (M) | 5.5E−07 | N.D. | No | No | No | No | No | No | No |
|  | kon(1/Ms) | 1.7E+05 | N.D. | No | No | No | No | No | No | No |
|  | kdis(1/s) | 9.2E−02 | N.D. | No | No | No | No | No | No | No |
| FcγRIIIB | KD (M) | No | N.D. | No | No | No | No | No | No | No |
|  | kon(1/Ms) | No | N.D. | No | No | No | No | No | No | No |
|  | kdis(1/s) | No | N.D. | No | No | No | No | No | No | No |
| FcRn | KD (M) | 1.8E−08 | N.D. | 5.2E−08 | 1.1E−08 | 1.3E−08 | 1.9E−08 | 2.3E−08 | 2.0E−08 | 2.3E−08 |
|  | kon(1/Ms) | 6.4E+05 | N.D. | 2.1E+05 | 6.1E+05 | 6.9E+05 | 4.8E+05 | 4.5E+05 | 5.8E+05 | 5.6E+05 |
|  | kdis(1/s) | 1.2E−02 | N.D. | 1.1E−02 | 6.8E−03 | 9.0E−03 | 9.0E−03 | 1.0E−02 | 1.2E−02 | 1.3E−02 |

Figure 1W:
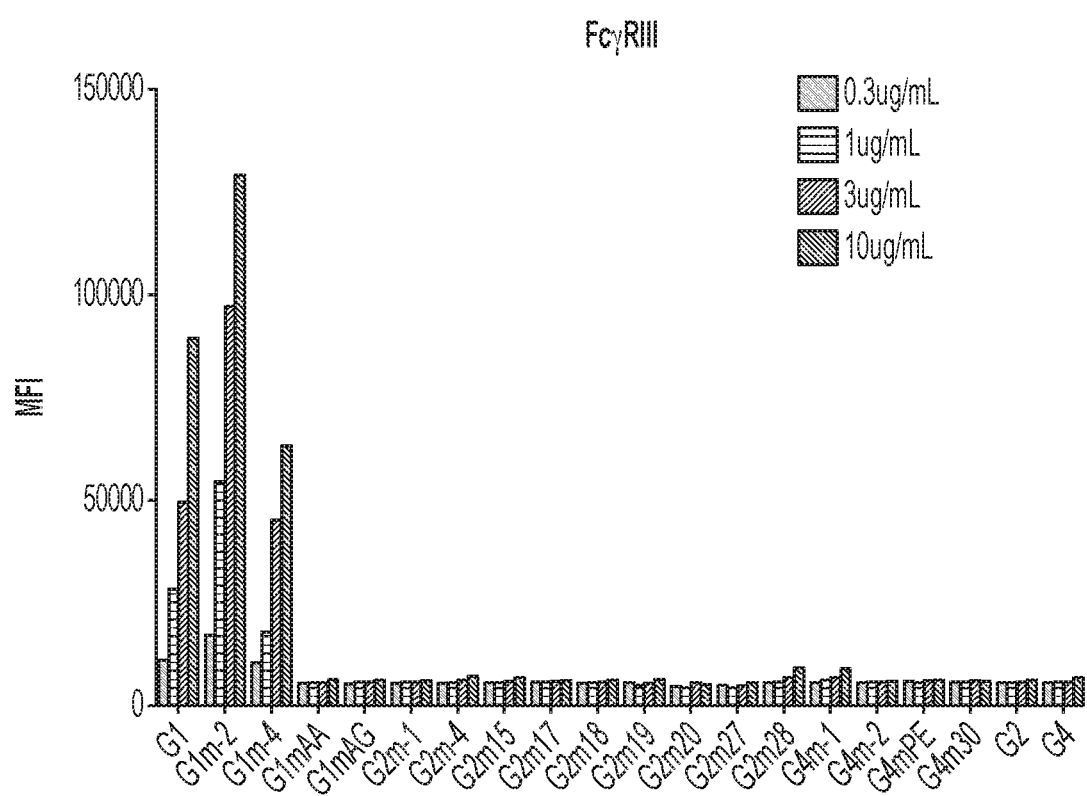

As shown in FIGS. 1A-1W, a number of human IgG1, IgG2, and IgG4 mutants showed binding activity to FCγRs expressed on the cell surface. Qualitative summaries of the changes of the mutants' Fcγ binding activity relative to the wild-type counterpart are provided in Tables 2-4 above.

Example 5. Human IgG Mutants Capable of Binding to Cellular FcγRIIB Showed Enhanced Agonist Activity To verify that binding to cellular FcγR2B would enhance agonist activity of the IgG mutants, a co-culture assay was developed, which involves CHO cells expressing FcγR2B and human CD8 positive T cells. CHO-FcγRIIB cells were plated at 2×10$^4$/well in 96-well cell culture plate and were incubated overnight. To isolate human CD8 positive T cells, fresh blood from healthy donors were mixed with equal volume of DPBS gently. The blood sample was then placed on top of Ficoll underlay and centrifuged 30 min at 1000 g at RT without brake. The buffy coat containing PBMC was harvested into a new tube and was washed with DPBS. CD8 positive T cells were isolated from the PBMC using EASY-SEP™ Human CD8+ T Cell Isolation Kit (Stemcell #17953) according to the kit manual. The isolated CD8+ T cells suspended in RPMI media were added to the plates with CHO-FcγRIIB cells. The anti-human CD3 antibody OKT3 was added to a final concentration of 0.1 ug/ml followed by addition of test antibodies diluted at desired concentrations. The plates were cultured for 3 days, and then the culture supernatants were harvested for measurement of IFNg concentration by ELISA using Human IFN-gamma ELISA Ready-SET-GO kit (EBIOSCIENCE, #88-7316-88).

Figure 2A:
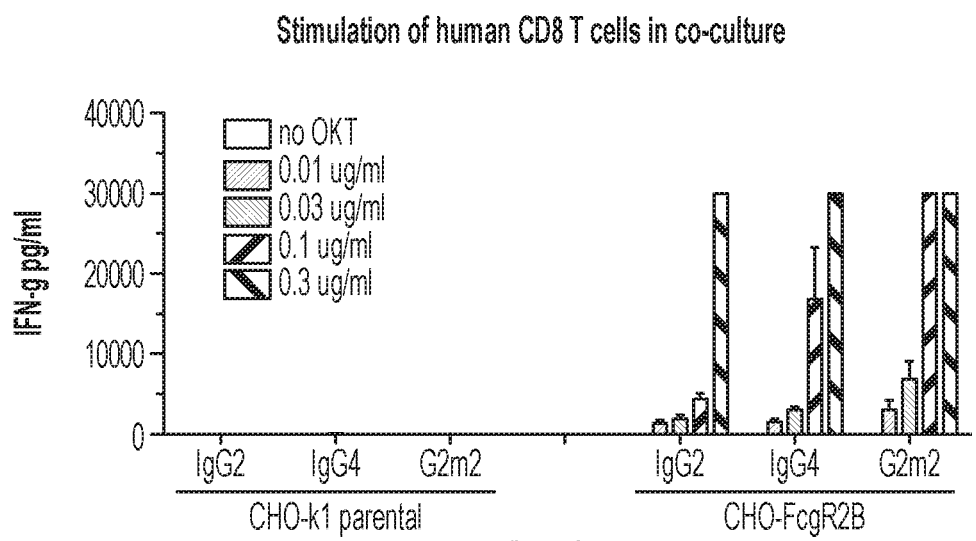
FIGS. 2A-2C are charts showing stimulation of human CD8+ T cells in co-culture with parental or FcγR expressing cells by a number of IgG variants as indicated by IFN-γ secretion. The groups, from left to right, correspond to: no OKT, 0.01 μg/ml, 0.03 μg/ml, 0.1 μg/ml, and 0.3 μg/ml, in FIG. 2A.
Figure 2B:
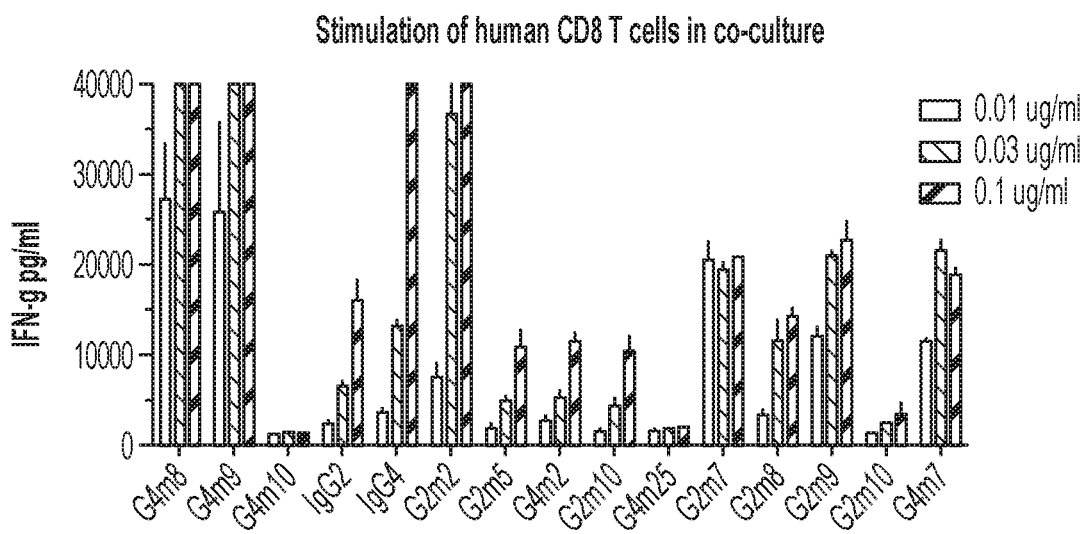
Figure 2C:
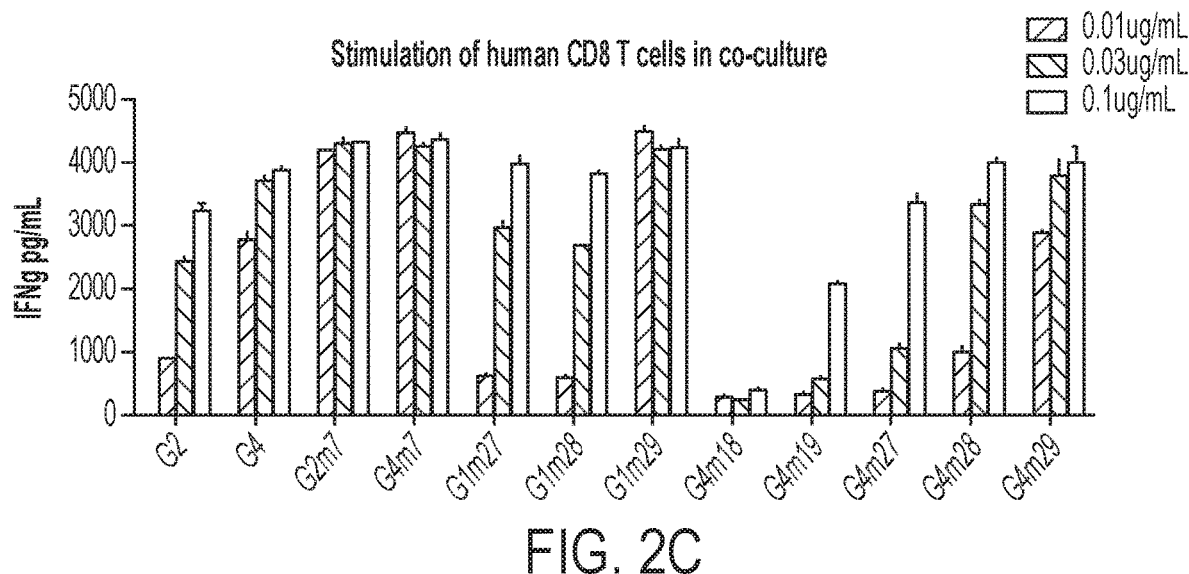

As shown in FIG. 2A-2C, a number of tested IgG mutants stimulated human CD8+ cells in the presence of CHO-FcγRIIB cells as evidenced by the secretion of IFN-γ.

Example 6. Effect of IgG Isotypes In Vitro and In Vivo in Mouse Models

Two different antibodies against mouse 4-1BB (CD137), LOB12.3 and 3H3, were examined in detail. These two antibodies were cloned and expressed as various mouse IgG isotypes including murine IgG1, a murine IgG1 N297A mutant known to have diminished ability to bind FcRs (as a negative control), and murine IgG2a.

Figure 3:
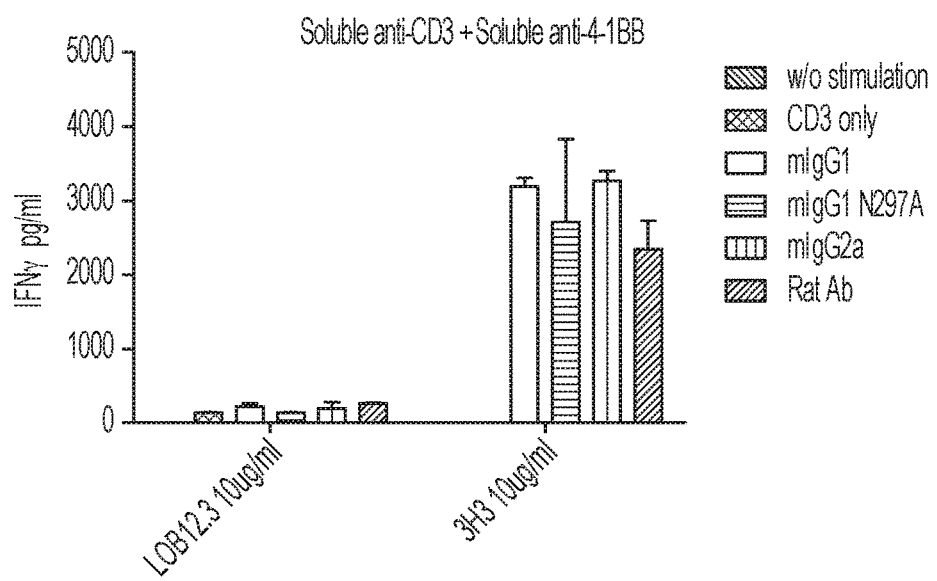
FIG. 3 is a chart showing murine T cell activation by a number of IgG molecules in the presence of anti-CD3 and/or anti-4-1BB antibodies.

Murine CD8 positive T cells were stimulated by the antibodies in a solution. In a typical in vitro co-stimulation assay of murine CD8 T cells, antibody LOB12.3 was not able to stimulate the T cells as measure by interferon gamma secretion, whereas 3H3 antibody exhibited agonistic activity regardless of the antibody isotype, as shown in FIG. 3.

Figure 4A:
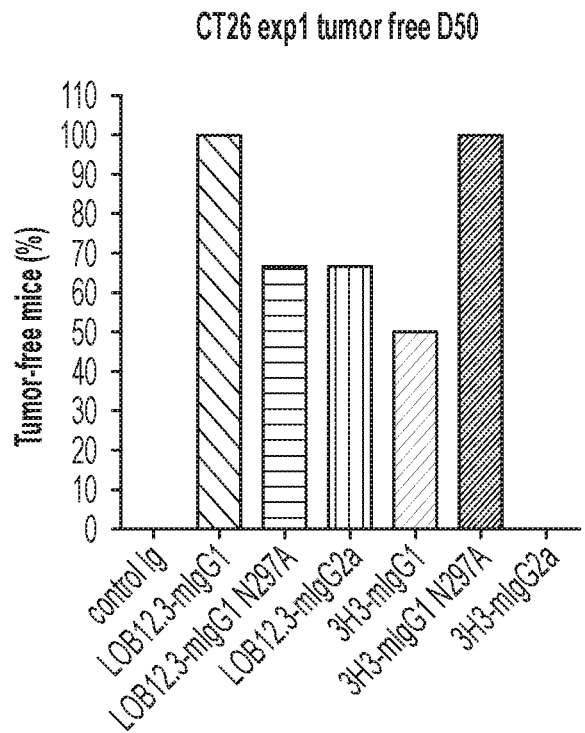
FIGS. 4A-4B are charts showing in vivo anti-tumor effects and the induction of serum ALT levels by anti-murine CD137 antibodies of different IgG isoforms.
Figure 4B:
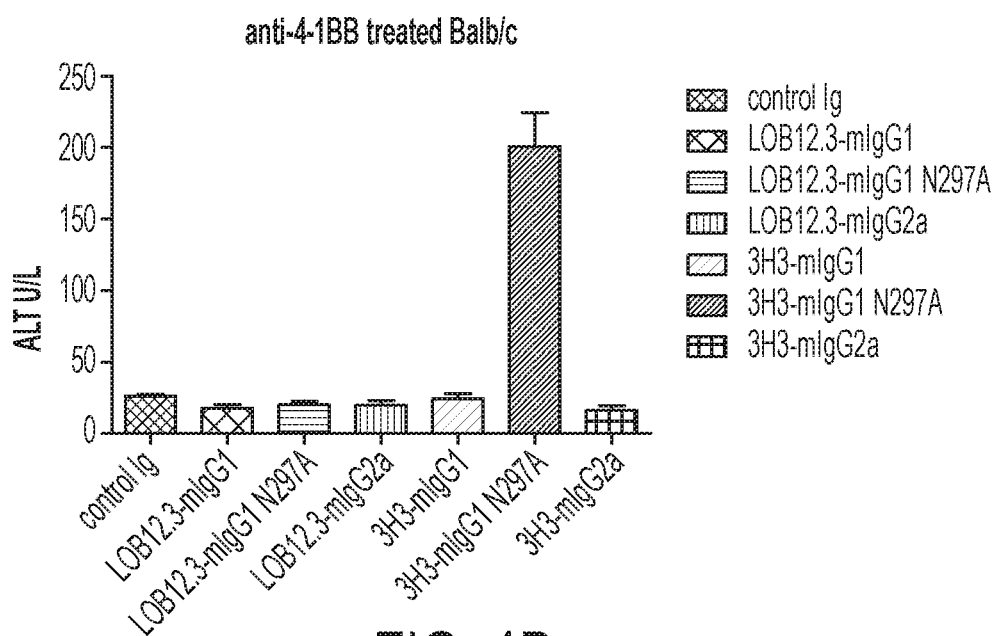
Figure 5A:
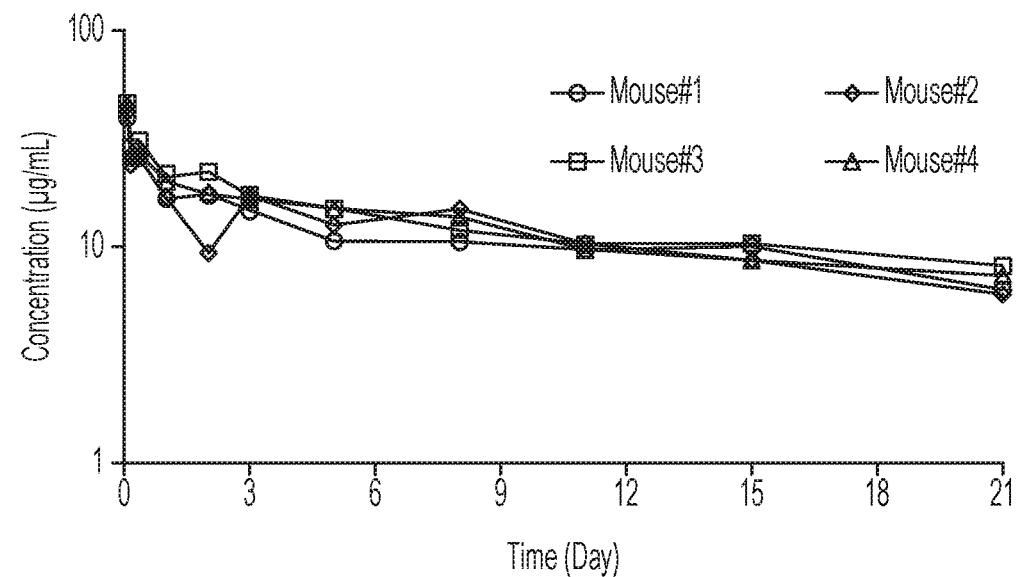
FIGS. 5A-5H are charts showing the antibody concentration of IgG variants in plasma after a single intravenous injection of 1-3 mg/kg. Male C57BL/6 mice were used, and four mice were assayed per time point. The charts of FIG. 5A show the plasma concentrations G1m27 after an IV dose of 3 mg/kg (top graph) and of G4m10 after an IV dose of 1.45 mg/kg (bottom graph). The charts of FIG. 5B show the plasma concentrations of G1m2 after an IV dose of 3 mg/kg (top graph) and of G4m2 after an IV dose of 3 mg/kg (bottom graph). The charts of FIG. 5C show the plasma concentrations of G1m29 after an IV dose of 3 mg/kg (top graph) and of G4m7 after an IV dose of 3 mg/kg (bottom graph). The charts of FIG. 5D show the plasma concentrations of G1m28 after an IV dose of 3 mg/kg (top graph) and of G4 after an IV dose of 3 mg/kg. The charts of FIG. 5E show the plasma concentrations of G4m28 after an IV dose of 1.45 mg/kg (top graph) and of G4m29 after an IV dose of 1.5 mg/kg (bottom graph). The charts of FIG. 5F show the plasma concentrations of G4m1 after an IV dose of 3 mg/kg (top graph) and of G4m27 after an IV dose of 1.45 mg/kg (bottom graph).
Figure 5A:
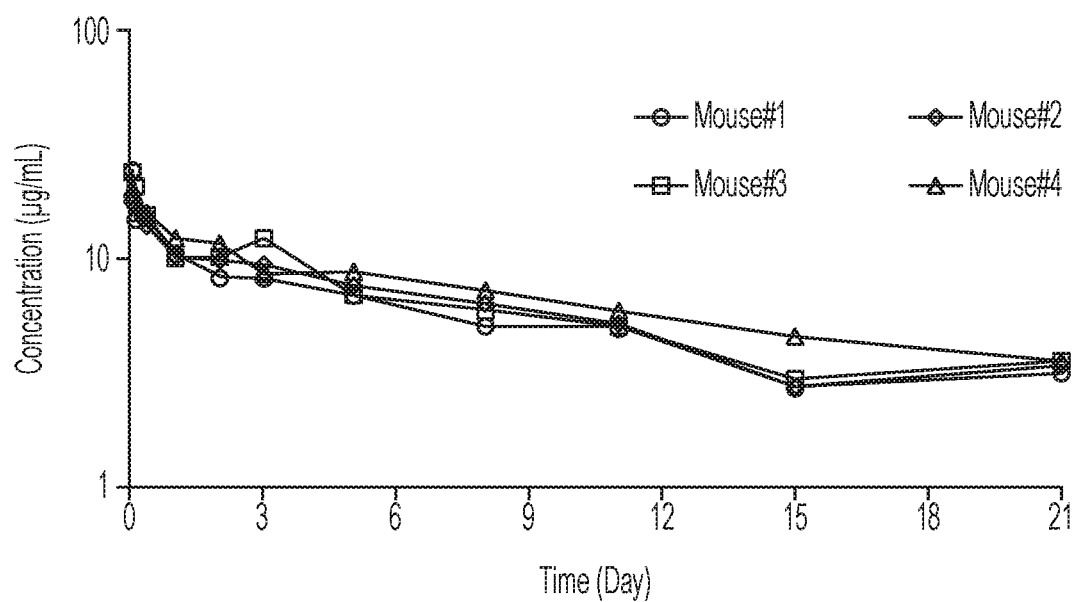
Figure 5B:
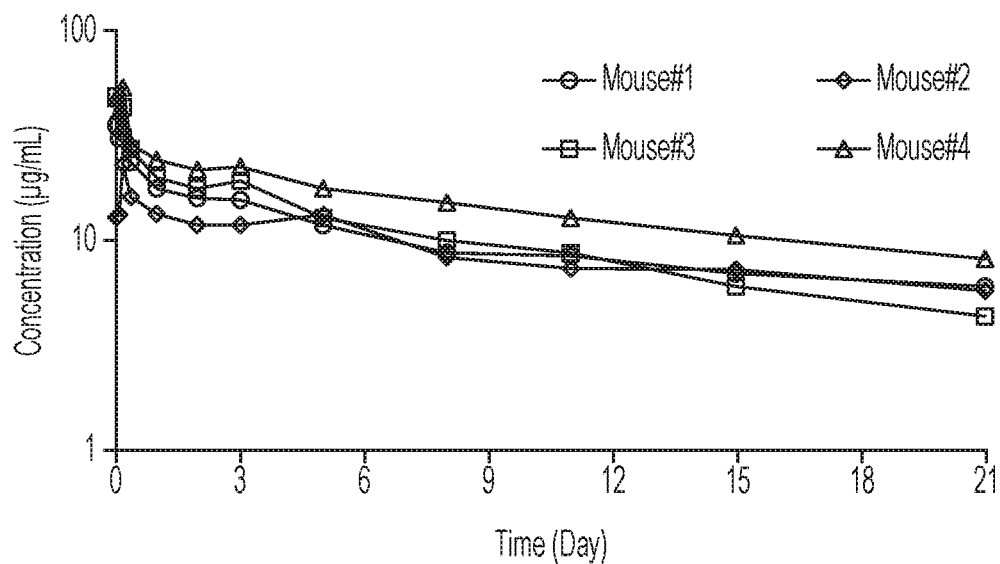
Figure 5B:
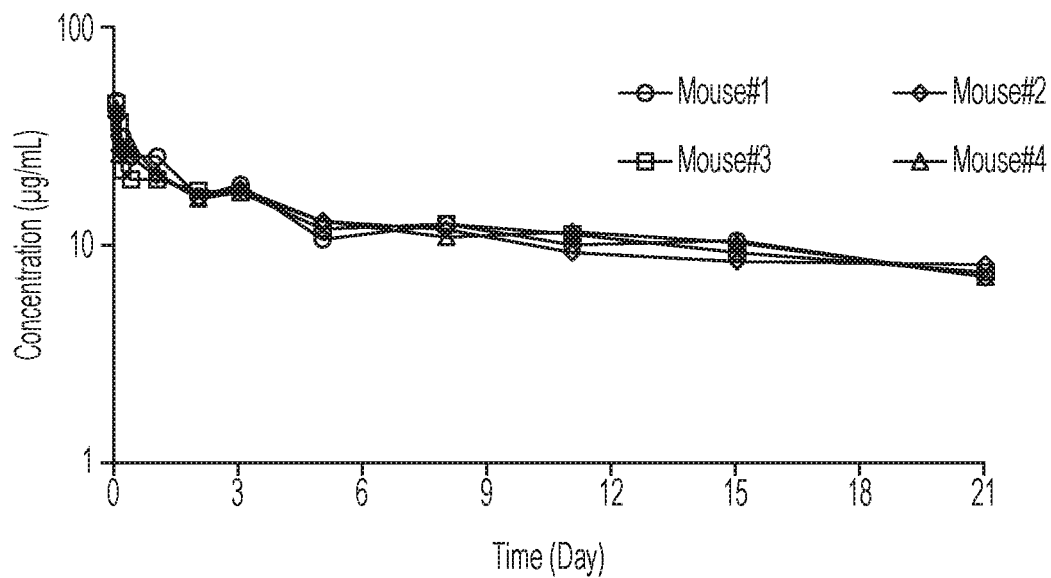
Figure 5C:
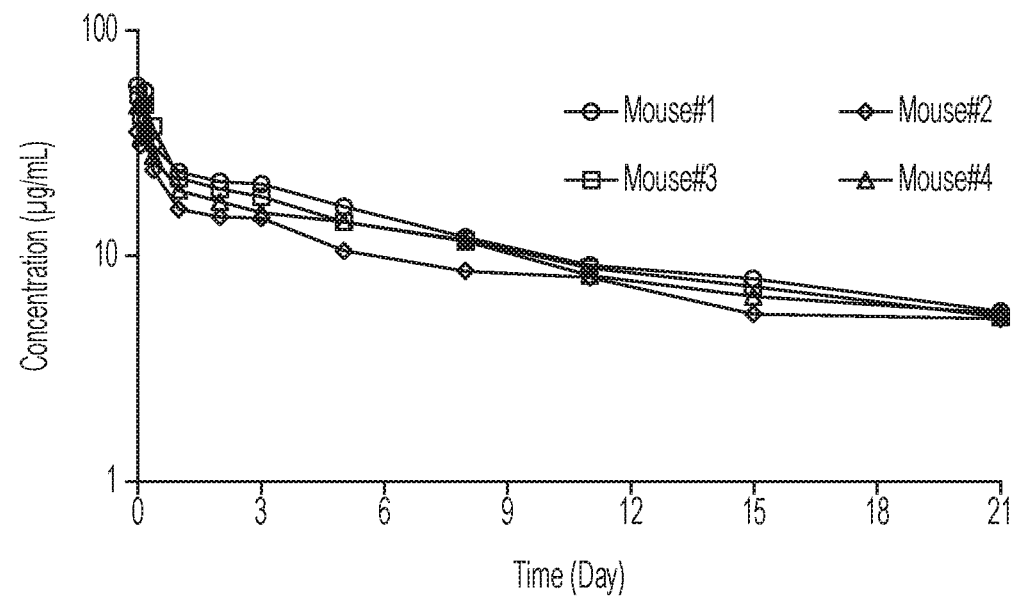
Figure 5C:
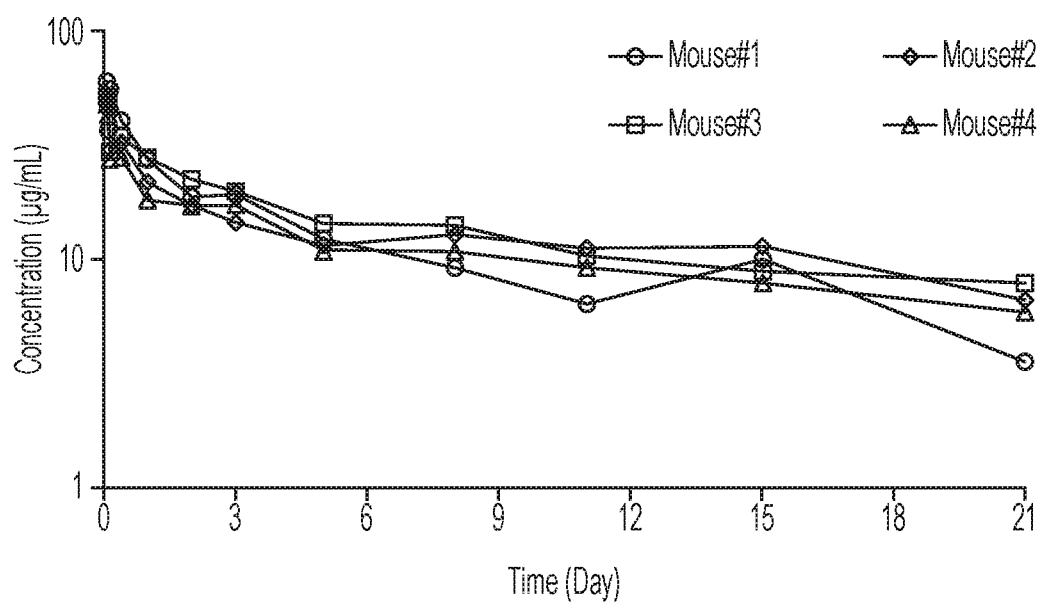
Figure 5D:
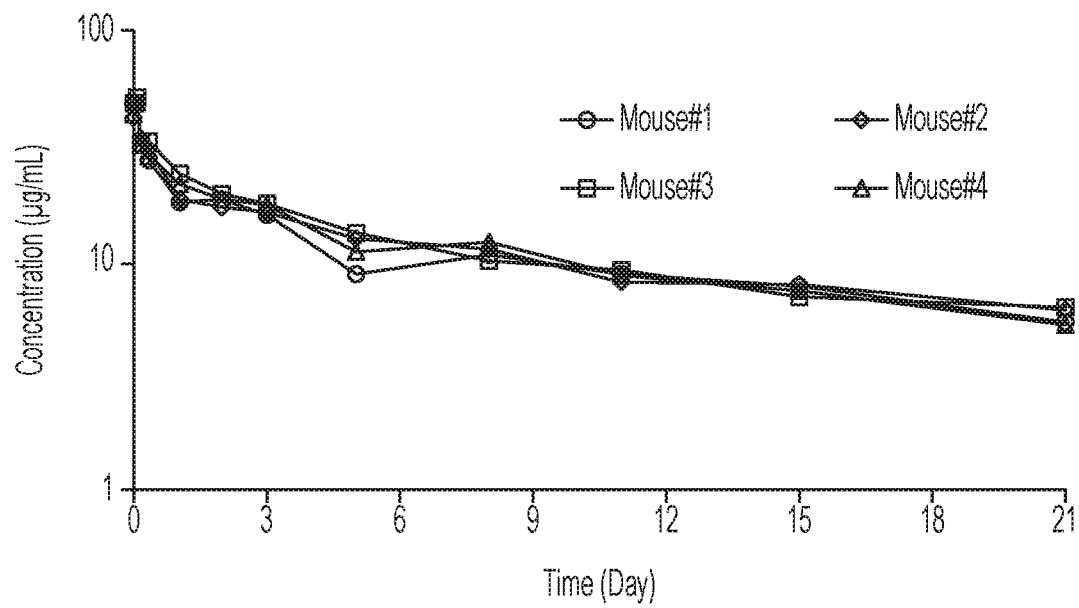
Figure 5D:
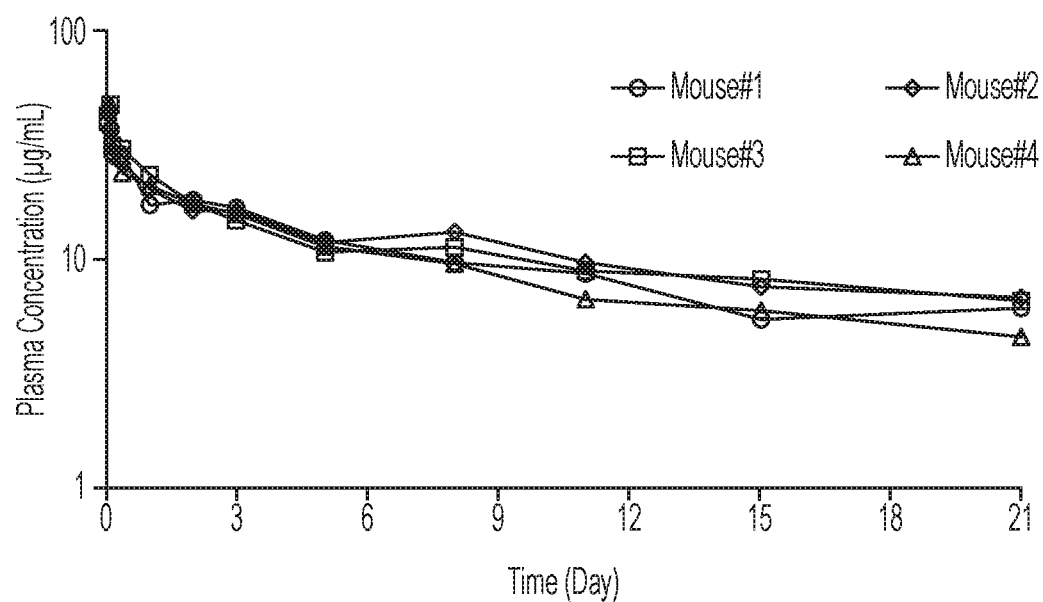
Figure 5E:
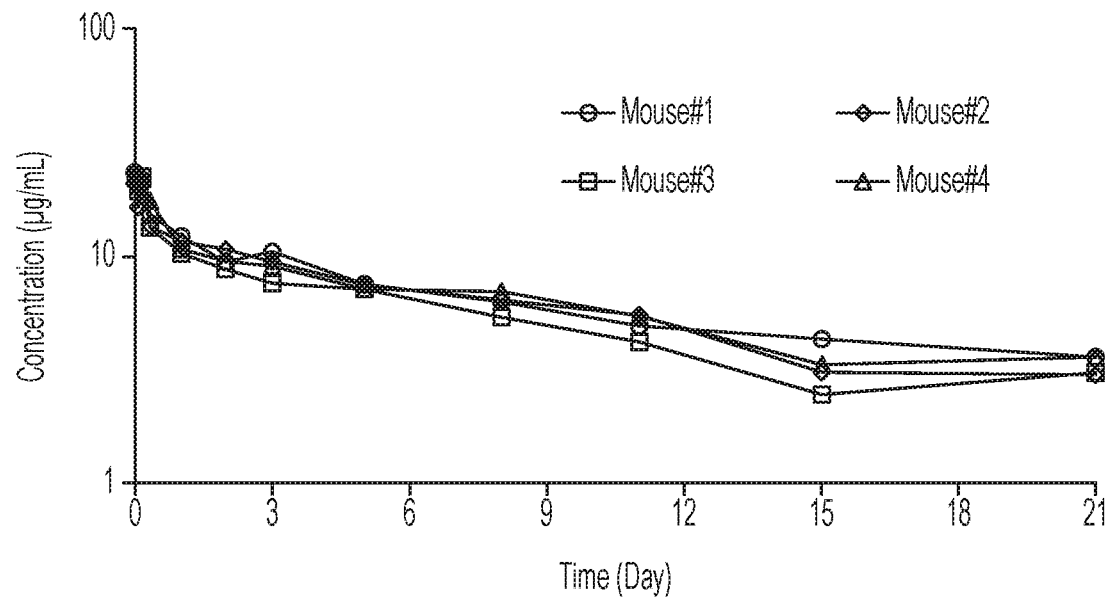
Figure 5E:
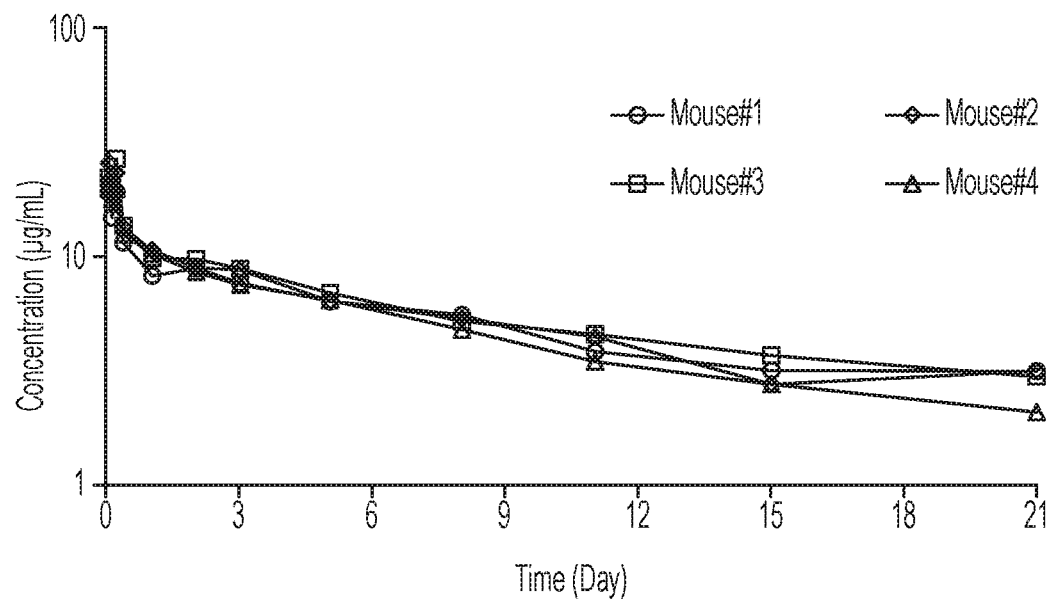
Figure 5F:
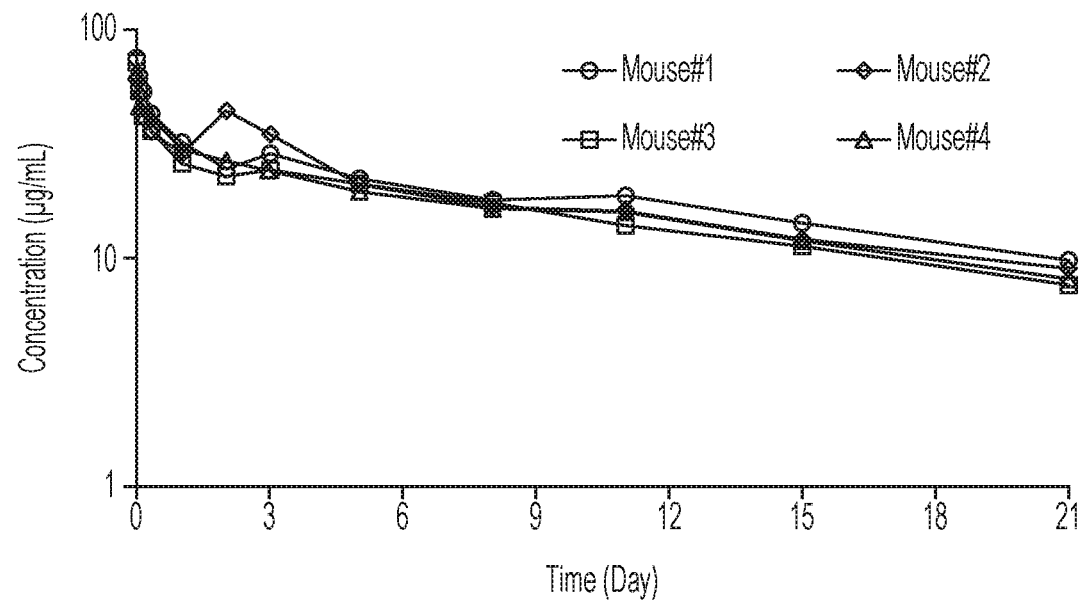
Figure 5F:
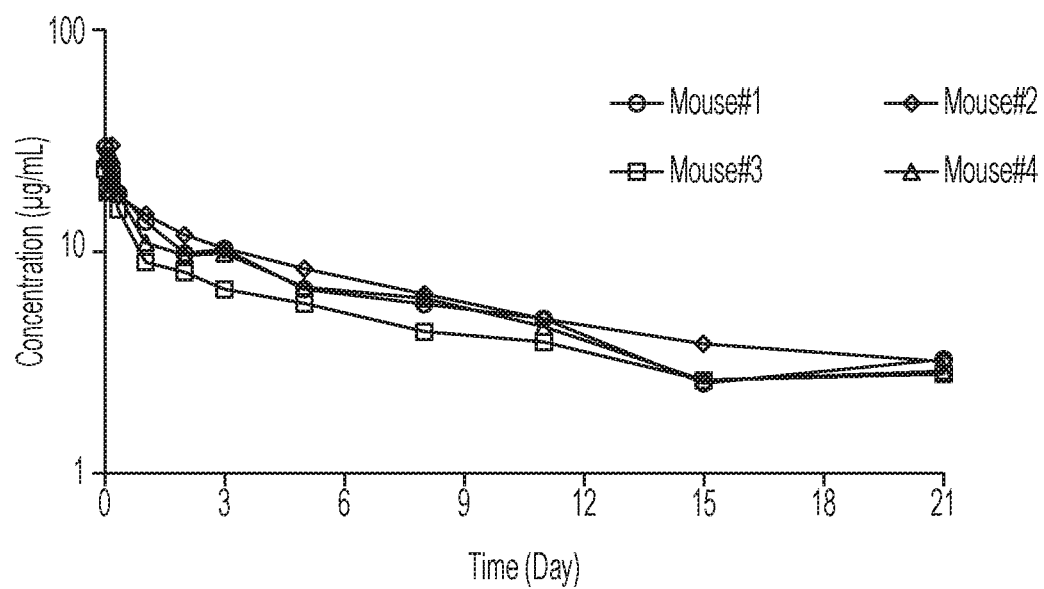
Figure 5G:
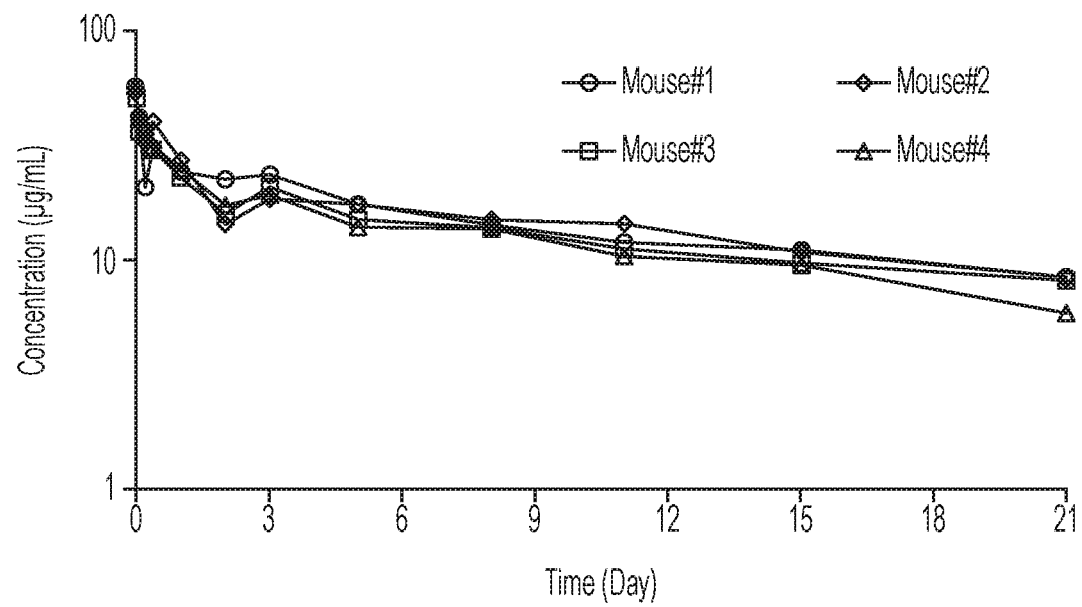
Figure 5G:
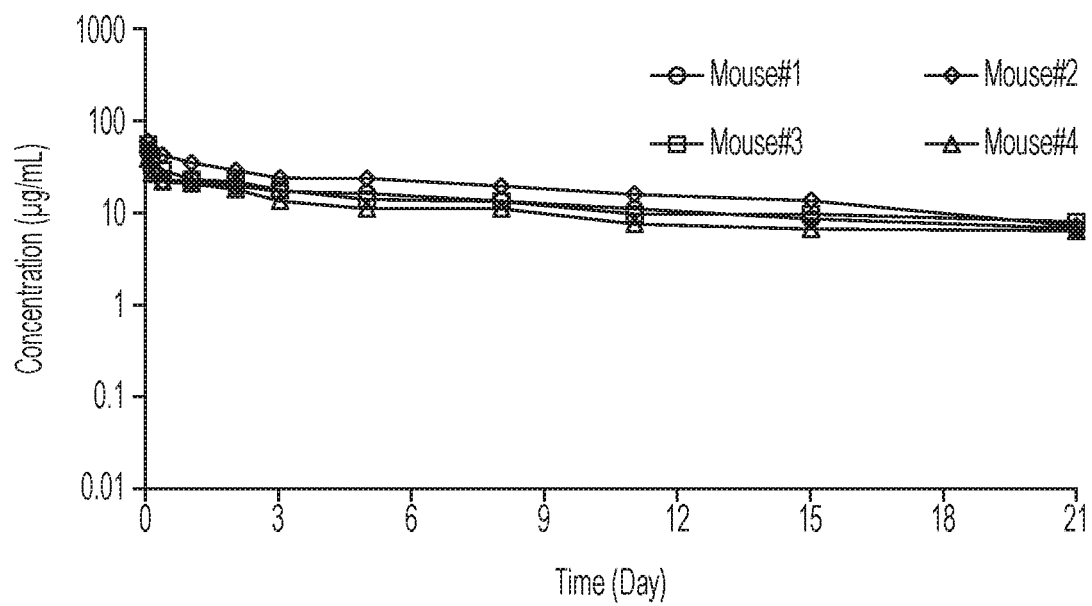
Figure 5H:
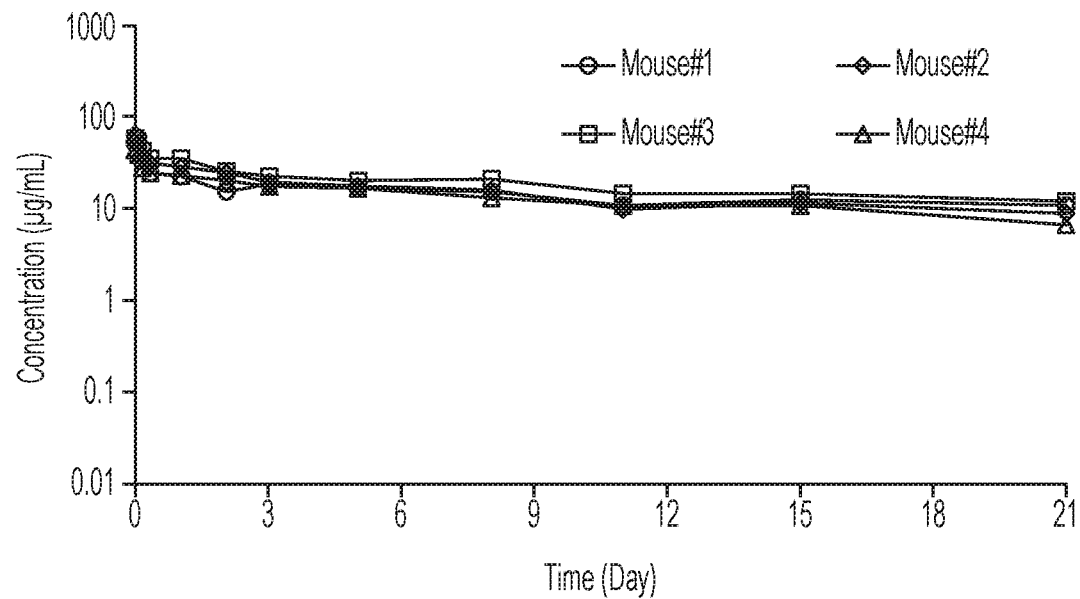
Figure 5H:
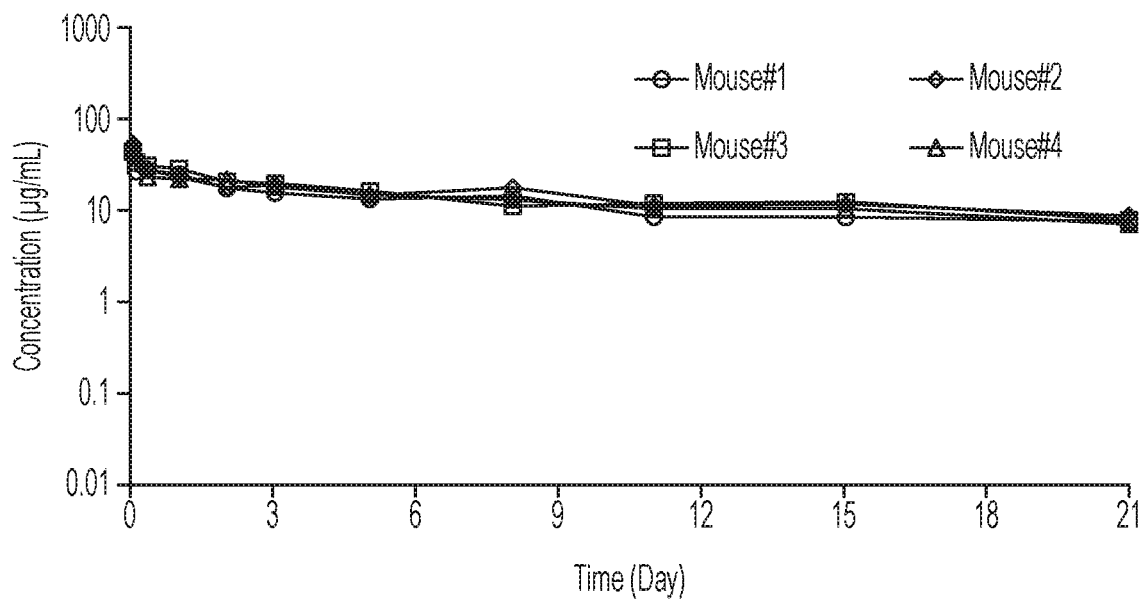

In vivo antitumor activity and liver toxicity were examined. The activity profile of these two antibodies and their isotypes were vastly different. In a murine syngeneic CT26 colorectal cancer model, both LOB12.3 and 3H3 showed robust antitumor activity including complete rejection of tumors, although the optimal isotype for each antibody is distinct. FIG. 4A-4B. LOB12.3 showed no obvious co-stimulatory activity in vitro but was efficacious in vivo when it was in murine IgG1 isotype, supporting that FcγR2B mediated cross-linking would result in efficient agonistic activity. 3H3 is intrinsically agonistic and its activity was not dependent on Fc-mediated cross-linking. In fact, 3H3 in Fc-null mutant was most efficacious.

An unexpected observation was the differential effect on liver toxicity of these antibodies. Both LOB12.3 and 3H3 were efficacious in inducing tumor rejection but only 3H3 showed liver toxicity as determined by increased liver enzyme ALT in serum samples of the treated animals (FIG. 4B).

These experimental data, for the first time, suggested a potential utility of selecting and engineering agonistic antibodies for increased therapeutic index of co-stimulation agonist antibodies.

Example 7. Pharmacokinetic Study of Chimeric Antibodies

In vivo studies were performed to study the pharmacokinetics of selected chimeric antibodies. Antibodies formulated in PBS were administered to C57BL/6 mice (6-7 weeks old, 19-20 g, male) via tail vein injection. Doses were 1-3 mg/kg (n=4 mice per group).

Blood samples were taken prior to administration of the antibodies, and 1 h, 2 h, 4 h, 8 h, 1 d, 2 d, 3 d, 5 d, 8 d, 11 d, 15 d and 21 d following administration. 10 uL blood of per time point was extracted and added to 40 uL of a PBS-BSA solution. The sample was then mixed well and centrifuged at 2000 g for 5 minutes at 4° C. The supernatant was put on dry ice immediately after collection and stored at approximately −70° C. until analysis. Antibody concentrations in the blood samples were determined by ELISA as described below briefly.

CD137 protein (human CD137-His tag protein (Sino Biological Inc. Cat #10377-H08H-100) or rhesus monkey CD137-His (Sino Biological Inc. Cat #90305-K08H-100)) was diluted in PBS to 1 μg/ml and used to coat an ELISA plate (Corning, Cat #9018, high binding) at a concentration of 500/well. The plate was incubated overnight at 4° C. The plate was then decanted and washed with PBS-T, and 2000/well assay diluent (1×PBS/1% BSA/0.05% Tween-20/0.05% proclin 300) was added. After a three hour incubation at room temperature, the plate was washed with PBS-T three times. The samples, at appropriate dilutions, along with known concentrations of antibody standards diluted in assay diluent to 0, 0.000003, 0.00003, 0.0003, 0.003, 0.03, and 0.3 μg/ml (or approximately 0, 0.00002, 0.0002, 0.002, 0.02, 0.2 and 2 nM), were then added to the plate (50 μl/well). The plate was incubated for one hour at 37° C. and then washed three times with PBS-T. Anti-human IgG-HRP conjugate (Bethyl Cat #A80-319P) at a 1:10,000 dilution was added to the plate (100 μl/well). The plate was incubated for 0.5 hour at 37° C., followed by washing with PBS-T three times. The TMB substrate solution was added (100 μl/well). The color was allowed to develop for 8 minutes before it was stopped with 1000/well 2N H2504. Absorbance at 450 nm was determined with an ELISA reader, and antibody concentrations were calculated from the standard curve dose responses.

FIGS. 5A-5G show the plasma antibody concentration of the chimeric antibodies after a single intravenous injection of 1-3 mg/kg. The pharmacokinetics parameters of these antibodies examined are listed in Table 13 below, which indicates that most, if not all, of the mutations examined did not alter the normal IgG PK parameters.

TABLE 13

Summary of Pharmacokinetics of IgG Variants Examined in Mice

| PK parameters | Unit | G4 | G4m2 | G4m7 | G1m27 | G1m28 | G1m29 | G4m27 | G4m28 |
|---|---|---|---|---|---|---|---|---|---|
| CL | mL/day/kg | 10.70 | 8.39 | 9.62 | 8.06 | 10.7 | 10.30 | 9.98 | 8.95 |
| $V_{ss}$ | mL/kg | 144 | 146 | 130 | 152 | 142 | 142 | 122 | 126 |
| V1 | mL/kg | 58.9 | 58.7 | 53.6 | 56.8 | 58.4 | 63.7 | 53.3 | 61.1 |
| Alpha $t_{1/2}$ | day | 0.1760 | 0.119 | 0.161 | 0.116 | 0.184 | 0.2850 | 0.306 | 0.295 |
| Beta $t_{1/2}$ | day | 9.9 | 12.3 | 10.2 | 13.40 | 9.54 | 9.9 | 8.9 | 10.3 |
| AUC | day*μg/mL | 287 | 359 | 324 | 374 | 282 | 294 | 146 | 164 |
| MRT | day | 13.8 | 17.5 | 14.4 | 19.0 | 13.4 | 13.8 | 12.2 | 14.3 |

| PK parameters | Unit | G4m29 | G1m2 | G4m10 | G2m19 | G4m1 | G1mAA | G2 | G2m1 |
|---|---|---|---|---|---|---|---|---|---|
| CL | mL/day/kg | 10.70 | 8.58 | 9.47 | 7.19 | 6.24 | 7.71 | 6.28 | 8.41 |
| $V_{ss}$ | mL/kg | 147 | 173 | 116 | 127 | 91 | 125 | 118 | 122 |
| V1 | mL/kg | 66.1 |  | 56.6 | 49.7 | 39.2 | 52.6 | 49.2 | 53.4 |
| Alpha $t_{1/2}$ | day | 0.256 |  | 0.151 | 0.182 | 0.099 | 0.0919 | 0.108 | 0.123 |
| Beta $t_{1/2}$ | day | 9.99 | 14.8 | 8.9 | 13.1 | 10.40 | 11.5 | 13.7 | 10.3 |
| AUC | day*μg/mL | 142 | 365.0 | 158 | 431 | 487 | 394 | 497 | 374 |
| MRT | day | 13.9 | 21 | 12.7 | 18.5 | 14.7 | 16.4 | 19.6 | 14.6 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A protein comprising a variant Fc region, wherein the variant Fc region comprises the amino acid sequence of SEQ ID NO: 6 or SEQ ID NO: 18.

2. The protein of claim 1, wherein the variant Fc region comprises the amino acid sequence of SEQ ID NO:6.

3. The protein of claim 1, wherein the variant Fc region comprises the amino acid sequence of SEQ ID NO: 18.

4. The protein of claim 1, wherein the protein is an antibody.

5. A pharmaceutical composition, comprising the protein of claim 1 and a pharmaceutically acceptable carrier.

* * * * *